(12) United States Patent
Gimbel et al.

(10) Patent No.: US 8,523,912 B2
(45) Date of Patent: Sep. 3, 2013

(54) POSTERIOR STABILIZATION SYSTEMS WITH SHARED, DUAL DAMPENER SYSTEMS

(75) Inventors: Jonathan A. Gimbel, Murrysville, PA (US); Michael S. Schular, Pittsburgh, PA (US); Erik J. Wagner, Austin, TX (US)

(73) Assignee: Flexuspine, Inc., Pittsburgh, PA (US)

( * ) Notice: Subject to any disclaimer, the term of this patent is extended or adjusted under 35 U.S.C. 154(b) by 1149 days.

(21) Appl. No.: 11/975,916

(22) Filed: Oct. 22, 2007

(65) Prior Publication Data
US 2009/0105757 A1    Apr. 23, 2009

(51) Int. Cl.
*A61B 17/70* (2006.01)

(52) U.S. Cl.
USPC .......... 606/253; 606/246; 606/257; 623/17.15

(58) Field of Classification Search
USPC .......... 623/17.12–17.15, 17.11; 606/246–279
See application file for complete search history.

(56) References Cited

U.S. PATENT DOCUMENTS

| | | | |
|---|---|---|---|
| 3,848,601 A | 11/1974 | Ma et al. | |
| 3,867,728 A | 2/1975 | Stubstad et al. | |
| 4,309,777 A | 1/1982 | Patil | |
| 4,349,921 A | 9/1982 | Kuntz | |
| 4,611,581 A | 9/1986 | Steffee | |
| 4,657,550 A | 4/1987 | Daher | |
| 4,696,290 A | 9/1987 | Steffee | |
| 4,743,260 A | 5/1988 | Burton | |
| 4,759,766 A | 7/1988 | Buettner-Janz et al. | |
| 4,759,769 A | 7/1988 | Hedman et al. | |
| 4,772,287 A | 9/1988 | Ray et al. | |
| 4,854,311 A | 8/1989 | Steffee | |
| 4,863,476 A | 9/1989 | Shepperd | |
| 4,863,477 A | 9/1989 | Monson | |
| 4,907,577 A | 3/1990 | Wu | |
| 4,911,718 A | 3/1990 | Lee et al. | |

(Continued)

FOREIGN PATENT DOCUMENTS

| | | |
|---|---|---|
| EP | 2117473 | 11/2009 |
| FR | 2716616 | 9/1995 |

(Continued)

OTHER PUBLICATIONS

U.S. Patent and Trademark Office "Communication" for U.S. Appl. No. 11/371,328, mailed Dec. 30, 2009.

(Continued)

*Primary Examiner* — Ellen C Hammond
*Assistant Examiner* — Stuart S Bray
(74) *Attorney, Agent, or Firm* — Meyertons, Hood, Kivlin, Kowert & Goetzel, P.C.; Eric B. Meyertons

(57) ABSTRACT

Dynamic posterior stabilization systems and methods of stabilizing vertebrae are described. A dynamic posterior stabilization system may include a first bone fastener configured to couple to a first vertebra, a second bone fastener configured to couple to a second vertebra, and a dampener system attached to the first bone fastener and the second bone fastener. The dampener system may include a first dampener set and a second dampener set. Compression of the first dampener set provides resistance to movement of the first bone fastener towards the second bone fastener. Compression of the first dampener set and the second dampener set provides resistance to movement of the first bone fastener away from the second bone fastener.

56 Claims, 39 Drawing Sheets

(56) References Cited

U.S. PATENT DOCUMENTS

| | | | |
|---|---|---|---|
| 4,932,975 | A | 6/1990 | Main et al. |
| 4,946,378 | A | 8/1990 | Hirayama et al. |
| 4,946,458 | A | 8/1990 | Harms et al. |
| 5,042,982 | A | 8/1991 | Harms et al. |
| 5,047,055 | A | 9/1991 | Bao et al. |
| 5,059,194 | A | 10/1991 | Michelson |
| 5,071,437 | A | 12/1991 | Steffee |
| 5,092,867 | A | 3/1992 | Harms et al. |
| 5,108,438 | A | 4/1992 | Stone |
| 5,123,926 | A | 6/1992 | Pisharodi |
| 5,171,278 | A | 12/1992 | Pisharodi |
| 5,171,281 | A | 12/1992 | Parsons et al. |
| 5,180,393 | A | 1/1993 | Commarmond |
| 5,192,326 | A | 3/1993 | Bao et al. |
| 5,196,013 | A | 3/1993 | Harms et al. |
| 5,207,678 | A | 5/1993 | Harms et al. |
| 5,246,458 | A | 9/1993 | Graham |
| 5,258,031 | A | 11/1993 | Salib et al. |
| 5,261,909 | A | 11/1993 | Sutterlin et al. |
| 5,306,307 | A | 4/1994 | Senter et al. |
| 5,306,309 | A | 4/1994 | Wagner et al. |
| 5,314,477 | A | 5/1994 | Marnay |
| 5,320,644 | A | 6/1994 | Baumgartner |
| 5,336,223 | A | 8/1994 | Rogers |
| 5,370,697 | A | 12/1994 | Baumgartner |
| 5,375,823 | A | 12/1994 | Navas |
| 5,397,364 | A | 3/1995 | Kozak et al. |
| 5,401,269 | A | 3/1995 | Buettner-Janz et al. |
| 5,403,315 | A | 4/1995 | Ashman |
| 5,415,661 | A | 5/1995 | Holmes |
| 5,423,816 | A | 6/1995 | Lin |
| 5,425,773 | A | 6/1995 | Boyd et al. |
| 5,443,467 | A | 8/1995 | Biedermann et al. |
| 5,458,642 | A | 10/1995 | Beer et al. |
| 5,458,643 | A | 10/1995 | Oka et al. |
| 5,480,401 | A | 1/1996 | Navas |
| 5,496,321 | A | 3/1996 | Puno et al. |
| 5,498,263 | A | 3/1996 | DiNello et al. |
| 5,514,132 | A | 5/1996 | Csernatony et al. |
| 5,514,180 | A | 5/1996 | Heggeness et al. |
| 5,522,899 | A | 6/1996 | Michelson |
| 5,534,028 | A | 7/1996 | Bao et al. |
| 5,534,029 | A | 7/1996 | Shima |
| 5,534,030 | A | 7/1996 | Navarro et al. |
| 5,545,165 | A | 8/1996 | Biedermann et al. |
| 5,556,431 | A | 9/1996 | Buettner-Janz |
| 5,562,663 | A | 10/1996 | Wisnewski et al. |
| 5,562,737 | A | 10/1996 | Graf |
| 5,562,738 | A | 10/1996 | Boyd et al. |
| 5,571,109 | A | 11/1996 | Bertagnoli |
| 5,609,635 | A | 3/1997 | Michelson |
| 5,645,599 | A | 7/1997 | Samani |
| 5,653,763 | A | 8/1997 | Errico et al. |
| 5,665,122 | A | 9/1997 | Kambin |
| 5,672,175 | A | 9/1997 | Martin |
| 5,672,176 | A | 9/1997 | Biedermann et al. |
| 5,674,294 | A | 10/1997 | Bainville et al. |
| 5,674,296 | A | 10/1997 | Bryan et al. |
| 5,676,701 | A | 10/1997 | Yuan et al. |
| 5,676,702 | A | 10/1997 | Ratron |
| 5,683,391 | A | 11/1997 | Boyd |
| 5,683,464 | A | 11/1997 | Wagner et al. |
| 5,863,465 | A | 11/1997 | Shinn et al. |
| 5,702,450 | A | 12/1997 | Bisserie |
| 5,725,527 | A | 3/1998 | Biedermann et al. |
| 5,733,284 | A | 3/1998 | Martin |
| 5,741,253 | A | 4/1998 | Michelson |
| 5,755,797 | A | 5/1998 | Baumgartner |
| 5,776,199 | A | 7/1998 | Michelson |
| 5,782,832 | A | 7/1998 | Larsen et al. |
| 5,785,647 | A | 7/1998 | Tompkins et al. |
| 5,797,909 | A | 8/1998 | Michelson |
| 5,800,549 | A | 9/1998 | Bao et al. |
| 5,800,550 | A | 9/1998 | Sertich |
| 5,810,819 | A | 9/1998 | Errico et al. |
| 5,824,093 | A | 10/1998 | Ray et al. |
| 5,824,094 | A | 10/1998 | Serhan et al. |
| 5,827,328 | A | 10/1998 | Buttermann |
| 5,861,041 | A | 1/1999 | Tienboon |
| 5,863,293 | A | 1/1999 | Richelsoph |
| 5,865,846 | A | 2/1999 | Bryan et al. |
| 5,865,848 | A | 2/1999 | Baker |
| 5,888,220 | A | 3/1999 | Felt et al. |
| 5,888,226 | A | 3/1999 | Rogozinski |
| 5,893,889 | A | 4/1999 | Harrington |
| 5,895,427 | A | 4/1999 | Kuslich et al. |
| 5,895,428 | A | 4/1999 | Berry |
| 5,899,941 | A | 5/1999 | Nishijima et al. |
| 5,928,243 | A | 7/1999 | Guyer |
| 5,935,133 | A | 8/1999 | Wagner et al. |
| 5,938,663 | A | 8/1999 | Petreto |
| 5,951,555 | A | 9/1999 | Rehak et al. |
| 5,961,518 | A | 10/1999 | Errico et al. |
| 5,961,554 | A | 10/1999 | Janson et al. |
| 5,964,769 | A | 10/1999 | Wagner et al. |
| 5,976,186 | A | 11/1999 | Bao et al. |
| 5,980,522 | A | 11/1999 | Koros et al. |
| 5,984,967 | A | 11/1999 | Zdeblick et al. |
| 5,989,250 | A | 11/1999 | Wagner et al. |
| 5,989,290 | A | 11/1999 | Biedermann et al. |
| 5,997,539 | A | 12/1999 | Errico et al. |
| 6,001,130 | A | 12/1999 | Bryan et al. |
| 6,017,344 | A | 1/2000 | Errico et al. |
| 6,019,792 | A | 2/2000 | Cauthen |
| 6,022,376 | A | 2/2000 | Assell et al. |
| 6,030,389 | A | 2/2000 | Wagner et al. |
| 6,039,763 | A | 3/2000 | Shelokov |
| 6,045,579 | A | 4/2000 | Hochschuler et al. |
| 6,053,921 | A | 4/2000 | Wagner et al. |
| 6,063,089 | A | 5/2000 | Errico et al. |
| RE36,758 | E | 6/2000 | Fitz |
| 6,080,193 | A | 6/2000 | Hochschuler et al. |
| 6,093,205 | A | 7/2000 | McLeod et al. |
| 6,096,038 | A | 8/2000 | Michelson |
| 6,102,950 | A | 8/2000 | Vaccaro |
| 6,106,526 | A | 8/2000 | Harms et al. |
| 6,110,210 | A | 8/2000 | Norton et al. |
| 6,113,637 | A | 9/2000 | Gill et al. |
| 6,123,707 | A | 9/2000 | Wagner et al. |
| 6,126,689 | A | 10/2000 | Brett |
| 6,132,430 | A | 10/2000 | Wagner et al. |
| 6,132,464 | A | 10/2000 | Martin |
| 6,132,465 | A | 10/2000 | Ray et al. |
| 6,136,031 | A | 10/2000 | Middleton |
| 6,139,579 | A | 10/2000 | Steffee et al. |
| 6,146,421 | A | 11/2000 | Gordon et al. |
| 6,146,422 | A | 11/2000 | Lawson |
| 6,156,067 | A | 12/2000 | Bryan et al. |
| 6,162,252 | A | 12/2000 | Kuras et al. |
| 6,165,218 | A | 12/2000 | Husson et al. |
| 6,176,882 | B1 | 1/2001 | Biedermann et al. |
| 6,179,874 | B1 | 1/2001 | Cauthen |
| 6,187,048 | B1 | 2/2001 | Milner et al. |
| 6,200,348 | B1 | 3/2001 | Biedermann et al. |
| 6,206,924 | B1 | 3/2001 | Timm |
| 6,214,049 | B1 | 4/2001 | Gayer et al. |
| 6,214,050 | B1 | 4/2001 | Huene |
| 6,217,579 | B1 | 4/2001 | Koros |
| 6,228,118 | B1 | 5/2001 | Gordon |
| 6,231,609 | B1 | 5/2001 | Mehdizadeh |
| 6,241,730 | B1 | 6/2001 | Alby |
| 6,264,656 | B1 | 7/2001 | Michelson |
| 6,290,724 | B1 | 9/2001 | Marino |
| 6,296,664 | B1 | 10/2001 | Middleton |
| 6,315,797 | B1 | 11/2001 | Middleton |
| 6,331,179 | B1 | 12/2001 | Freid et al. |
| 6,348,071 | B1 | 2/2002 | Steffee et al. |
| RE37,665 | E | 4/2002 | Ralph et al. |
| 6,368,350 | B1 | 4/2002 | Erickson |
| 6,368,351 | B1 | 4/2002 | Glenn et al. |
| 6,371,990 | B1 | 4/2002 | Ferree |
| 6,375,682 | B1 | 4/2002 | Fleischmann et al. |
| 6,375,683 | B1 | 4/2002 | Crozet et al. |
| 6,391,190 | B1 | 5/2002 | Wagner et al. |

| | | | | | | |
|---|---|---|---|---|---|---|
| 6,395,032 | B1 | 5/2002 | Gauchet | 6,953,477 | B2 | 10/2005 | Berry |
| 6,395,034 | B1 | 5/2002 | Suddaby | 6,962,606 | B2 | 11/2005 | Michelson |
| 6,402,784 | B1 | 6/2002 | Wardlaw | 6,964,664 | B2 | 11/2005 | Freid et al. |
| 6,402,785 | B1 | 6/2002 | Zdeblick et al. | 6,966,929 | B2 | 11/2005 | Mitchell |
| 6,409,766 | B1 | 6/2002 | Brett | 6,966,930 | B2 | 11/2005 | Arnin et al. |
| 6,413,259 | B1 | 7/2002 | Lyons et al. | 6,974,478 | B2 | 12/2005 | Reiley et al. |
| 6,416,515 | B1 | 7/2002 | Wagner et al. | 6,981,989 | B1 | 1/2006 | Fleischmann et al. |
| 6,419,703 | B1 | 7/2002 | Fallin et al. | 6,991,632 | B2 | 1/2006 | Ritland |
| 6,419,704 | B1 | 7/2002 | Ferree | 6,994,727 | B2 | 2/2006 | Khandkar et al. |
| 6,436,140 | B1 | 8/2002 | Liu et al. | 6,997,929 | B2 | 2/2006 | Manzi et al. |
| 6,440,168 | B1 | 8/2002 | Cauthen | 7,011,685 | B2 | 3/2006 | Arnin et al. |
| 6,442,814 | B1 | 9/2002 | Landry et al. | 7,018,415 | B1 | 3/2006 | McKay |
| 6,443,990 | B1 | 9/2002 | Aebi et al. | 7,029,475 | B2 | 4/2006 | Panjabi |
| 6,447,512 | B1 | 9/2002 | Landry et al. | 7,083,622 | B2 | 8/2006 | Simonson |
| 6,447,544 | B1 | 9/2002 | Michelson | 7,083,649 | B2 | 8/2006 | Zucherman et al. |
| 6,451,021 | B1 | 9/2002 | Ralph et al. | 7,090,698 | B2 | 8/2006 | Goble et al. |
| 6,454,769 | B2 | 9/2002 | Wagner et al. | 7,101,398 | B2 | 9/2006 | Dooris et al. |
| 6,454,806 | B1 | 9/2002 | Cohen et al. | 7,118,579 | B2 | 10/2006 | Michelson |
| 6,454,807 | B1 | 9/2002 | Jackson | 7,118,580 | B1 | 10/2006 | Beyersdorff et al. |
| 6,478,822 | B1 | 11/2002 | Leroux et al. | 7,128,760 | B2 | 10/2006 | Michelson |
| 6,478,823 | B1 | 11/2002 | Michelson | 7,147,664 | B2 | 12/2006 | Louis et al. |
| 6,482,207 | B1 | 11/2002 | Errico | 7,153,310 | B2 | 12/2006 | Ralph et al. |
| 6,482,234 | B1 | 11/2002 | Weber et al. | 7,204,853 | B2 | 4/2007 | Gordon et al. |
| 6,488,710 | B2 | 12/2002 | Besselink | 7,273,496 | B2 | 9/2007 | Mitchell |
| 6,500,205 | B1 | 12/2002 | Michelson | 7,291,150 | B2 | 11/2007 | Graf |
| 6,520,996 | B1 | 2/2003 | Manasas et al. | 7,291,173 | B2 | 11/2007 | Richelsoph et al. |
| 6,524,312 | B2 | 2/2003 | Landry et al. | 7,311,713 | B2 | 12/2007 | Johnson et al. |
| 6,533,817 | B1 | 3/2003 | Norton et al. | 7,316,714 | B2 | 1/2008 | Gordon et al. |
| 6,533,818 | B1 | 3/2003 | Weber et al. | 7,318,839 | B2 | 1/2008 | Malberg et al. |
| 6,540,748 | B2 | 4/2003 | Lombardo | 7,320,707 | B2 | 1/2008 | Zucherman |
| 6,558,423 | B1 | 5/2003 | Michelson | 7,326,250 | B2 | 2/2008 | Beaurain et al. |
| 6,562,040 | B1 | 5/2003 | Wagner et al. | 7,338,525 | B2 | 3/2008 | Ferree |
| 6,562,074 | B2 | 5/2003 | Gerbec et al. | 7,338,527 | B2 | 3/2008 | Blatt et al. |
| 6,565,566 | B1 | 5/2003 | Wagner et al. | 7,364,589 | B2 | 4/2008 | Eisermann |
| 6,565,605 | B2 | 5/2003 | Goble et al. | 7,473,276 | B2 | 1/2009 | Aebi et al. |
| 6,569,442 | B2 | 5/2003 | Gan et al. | 7,476,238 | B2 | 1/2009 | Panjabi |
| 6,572,653 | B1 | 6/2003 | Simonson | 7,485,146 | B1 | 2/2009 | Crook et al. |
| 6,576,016 | B1 | 6/2003 | Hochschuler et al. | 7,517,359 | B2 | 4/2009 | Drewry et al. |
| 6,579,318 | B2 | 6/2003 | Varga et al. | 7,547,309 | B2 | 6/2009 | Bertagnoli et al. |
| 6,579,319 | B2 | 6/2003 | Goble et al. | 7,550,009 | B2 | 6/2009 | Arnin et al. |
| 6,582,467 | B1 | 6/2003 | Teitelbaum et al. | 7,556,651 | B2 | 7/2009 | Humphreys et al. |
| 6,595,992 | B1 | 7/2003 | Wagner et al. | 7,615,068 | B2 | 11/2009 | Timm et al. |
| 6,595,998 | B2 | 7/2003 | Johnson et al. | 7,635,379 | B2 | 12/2009 | Callahan et al. |
| 6,610,091 | B1 | 8/2003 | Reiley | 7,682,396 | B2 | 3/2010 | Beaurain et al. |
| 6,610,094 | B2 | 8/2003 | Husson | 7,699,875 | B2 | 4/2010 | Timm et al. |
| 6,613,050 | B1 | 9/2003 | Wagner et al. | 7,708,778 | B2 | 5/2010 | Gordon et al. |
| 6,616,671 | B2 | 9/2003 | Landry et al. | 7,713,287 | B2 | 5/2010 | Timm et al. |
| 6,626,904 | B1 | 9/2003 | Jammet et al. | 7,713,288 | B2 | 5/2010 | Timm et al. |
| 6,626,905 | B1 | 9/2003 | Schmeil et al. | 7,753,958 | B2 | 7/2010 | Gordon et al. |
| 6,635,062 | B2 | 10/2003 | Ray et al. | 7,771,479 | B2 | 8/2010 | Humphreys et al. |
| 6,641,614 | B1 | 11/2003 | Wagner et al. | 7,785,351 | B2 | 8/2010 | Gordon et al. |
| 6,648,893 | B2 | 11/2003 | Dudasik | 7,794,480 | B2 | 9/2010 | Gordon et al. |
| 6,648,915 | B2 | 11/2003 | Sazy | 7,799,082 | B2 | 9/2010 | Gordon et al. |
| 6,648,917 | B2 | 11/2003 | Gerbec et al. | 7,811,309 | B2 | 10/2010 | Timm et al. |
| 6,666,870 | B2 | 12/2003 | Dixon | 7,909,869 | B2 | 3/2011 | Gordon et al. |
| 6,666,891 | B2 | 12/2003 | Boehm et al. | 7,909,877 | B2 | 3/2011 | Krueger et al. |
| 6,679,915 | B1 | 1/2004 | Cauthen | 7,931,675 | B2 | 4/2011 | Panjabi et al. |
| 6,682,533 | B1 | 1/2004 | Dinsdale et al. | 7,942,905 | B2 | 5/2011 | Lim et al. |
| 6,685,742 | B1 | 2/2004 | Jackson | 7,951,170 | B2 | 5/2011 | Jackson |
| 6,692,495 | B1 | 2/2004 | Zacouto | 7,959,677 | B2 | 6/2011 | Landry et al. |
| 6,706,070 | B1 | 3/2004 | Wagner et al. | 8,043,379 | B2 | 10/2011 | Moumene et al. |
| 6,712,819 | B2 | 3/2004 | Zucherman et al. | 8,052,723 | B2 | 11/2011 | Gordon et al. |
| 6,716,247 | B2 | 4/2004 | Michelson | 8,062,375 | B2 | 11/2011 | Glerum et al. |
| 6,719,796 | B2 | 4/2004 | Cohen et al. | 8,105,382 | B2 | 1/2012 | Olmos et al. |
| 6,733,531 | B1 | 5/2004 | Trieu | 8,118,869 | B2 | 2/2012 | Gordon et al. |
| 6,736,850 | B2 | 5/2004 | Davis | 8,118,870 | B2 | 2/2012 | Gordon et al. |
| 6,743,257 | B2 | 6/2004 | Castro | 8,118,871 | B2 | 2/2012 | Gordon et al. |
| 6,758,861 | B2 | 7/2004 | Ralph et al. | 8,123,810 | B2 | 2/2012 | Gordon et al. |
| 6,773,460 | B2 | 8/2004 | Jackson | 8,157,844 | B2 | 4/2012 | Gimbel et al. |
| 6,802,844 | B2 | 10/2004 | Ferree | 8,172,903 | B2 | 5/2012 | Gordon et al. |
| 6,811,567 | B2 | 11/2004 | Reiley | 8,182,514 | B2 | 5/2012 | Gimbel et al. |
| 6,821,298 | B1 | 11/2004 | Jackson | 8,187,330 | B2 | 5/2012 | Gimbel et al. |
| 6,852,129 | B2 | 2/2005 | Gerbec et al. | 8,257,440 | B2 | 9/2012 | Gordon et al. |
| 6,863,673 | B2 | 3/2005 | Gerbec et al. | 8,267,965 | B2 | 9/2012 | Gimbel et al. |
| D505,205 | S | 5/2005 | Freid | 8,377,098 | B2 | 2/2013 | Landry et al. |
| 6,893,464 | B2 | 5/2005 | Kiester | 8,388,687 | B2 | 3/2013 | Gimbel et al. |
| 6,902,580 | B2 | 6/2005 | Fallin et al. | 2001/0020476 | A1 | 9/2001 | Gan et al. |
| 6,928,284 | B2 | 8/2005 | Palat et al. | 2001/0032020 | A1 | 10/2001 | Besselink |
| 6,936,070 | B1 | 8/2005 | Muhanna | 2002/0040243 | A1 | 4/2002 | Atalli et al. |

| Publication No. | Date | Inventor |
|---|---|---|
| 2002/0045945 A1 | 4/2002 | Liu et al. |
| 2002/0065557 A1 | 5/2002 | Goble et al. |
| 2002/0068977 A1 | 6/2002 | Jackson |
| 2002/0072801 A1 | 6/2002 | Michelson |
| 2002/0082701 A1 | 6/2002 | Zdeblick et al. |
| 2002/0091390 A1 | 7/2002 | Michelson |
| 2002/0095154 A1 | 7/2002 | Atkinson et al. |
| 2002/0123806 A1 | 9/2002 | Reiley |
| 2002/0128659 A1 | 9/2002 | Michelson |
| 2002/0128714 A1 | 9/2002 | Manasas et al. |
| 2002/0130112 A1 | 9/2002 | Manasas et al. |
| 2002/0138077 A1 | 9/2002 | Ferree |
| 2002/0143401 A1 | 10/2002 | Michelson |
| 2003/0028250 A1 | 2/2003 | Reiley et al. |
| 2003/0040802 A1 | 2/2003 | Errico |
| 2003/0055427 A1 | 3/2003 | Graf |
| 2003/0069643 A1 | 4/2003 | Ralph et al. |
| 2003/0074063 A1 | 4/2003 | Gerbec et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0135275 A1 | 7/2003 | Garcia et al. |
| 2003/0135277 A1 | 7/2003 | Bryan et al. |
| 2003/0139812 A1 | 7/2003 | Garcia et al. |
| 2003/0149483 A1 | 8/2003 | Michelson |
| 2003/0176923 A1 | 9/2003 | Keller et al. |
| 2003/0191470 A1 | 10/2003 | Ritland |
| 2003/0204259 A1 | 10/2003 | Goble et al. |
| 2003/0204260 A1 | 10/2003 | Ferree |
| 2003/0220643 A1 | 11/2003 | Ferree |
| 2003/0225409 A1 | 12/2003 | Freid et al. |
| 2003/0233145 A1 | 12/2003 | Landry et al. |
| 2004/0006391 A1 | 1/2004 | Reiley |
| 2004/0019353 A1 | 1/2004 | Freid et al. |
| 2004/0030387 A1 | 2/2004 | Landry et al. |
| 2004/0030389 A1 | 2/2004 | Ferree |
| 2004/0039448 A1 | 2/2004 | Pisharodi |
| 2004/0044411 A1 | 3/2004 | Suddaby |
| 2004/0049190 A1 | 3/2004 | Biedermann et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049280 A1 | 3/2004 | Cauthen |
| 2004/0049281 A1 | 3/2004 | Reiley |
| 2004/0087947 A1 | 5/2004 | Lim et al. |
| 2004/0093083 A1 | 5/2004 | Branch et al. |
| 2004/0102774 A1 | 5/2004 | Trieu |
| 2004/0106997 A1 | 6/2004 | Lieberson |
| 2004/0117020 A1 | 6/2004 | Frey et al. |
| 2004/0127989 A1 | 7/2004 | Dooris et al. |
| 2004/0133278 A1 | 7/2004 | Marino et al. |
| 2004/0133281 A1 | 7/2004 | Khandkar et al. |
| 2004/0138662 A1 | 7/2004 | Landry et al. |
| 2004/0138749 A1 | 7/2004 | Zucherman |
| 2004/0143265 A1 | 7/2004 | Landry et al. |
| 2004/0143332 A1 | 7/2004 | Krueger et al. |
| 2004/0147928 A1 | 7/2004 | Landry et al. |
| 2004/0153065 A1 | 8/2004 | Lim |
| 2004/0167626 A1 | 8/2004 | Geremakis et al. |
| 2004/0181223 A1 | 9/2004 | Ritland |
| 2004/0181284 A1 | 9/2004 | Simonson |
| 2004/0220567 A1 | 11/2004 | Eisermann et al. |
| 2004/0236327 A1 | 11/2004 | Paul et al. |
| 2004/0236329 A1 | 11/2004 | Panjabi |
| 2004/0243240 A1 | 12/2004 | Beaurain et al. |
| 2004/0254643 A1 | 12/2004 | Jackson |
| 2004/0254644 A1 | 12/2004 | Taylor |
| 2004/0267364 A1 | 12/2004 | Carli et al. |
| 2004/0267369 A1 | 12/2004 | Lyons et al. |
| 2005/0010295 A1 | 1/2005 | Michelson |
| 2005/0015146 A1 | 1/2005 | Louis et al. |
| 2005/0015149 A1 | 1/2005 | Michelson |
| 2005/0021144 A1 | 1/2005 | Malberg et al. |
| 2005/0027361 A1 | 2/2005 | Reiley |
| 2005/0033431 A1 | 2/2005 | Gordon et al. |
| 2005/0033432 A1 | 2/2005 | Gordon et al. |
| 2005/0033437 A1 | 2/2005 | Bao et al. |
| 2005/0033439 A1 | 2/2005 | Gordon et al. |
| 2005/0060034 A1 | 3/2005 | Berry |
| 2005/0085815 A1 | 4/2005 | Harms et al. |
| 2005/0107881 A1 | 5/2005 | Alleyne et al. |
| 2005/0113927 A1 | 5/2005 | Malek |
| 2005/0124991 A1 | 6/2005 | Jahng |
| 2005/0125061 A1 | 6/2005 | Zucherman et al. |
| 2005/0131406 A1 | 6/2005 | Reiley |
| 2005/0143818 A1 | 6/2005 | Yuan et al. |
| 2005/0149020 A1 | 7/2005 | Jahng |
| 2005/0149023 A1 | 7/2005 | Ritland |
| 2005/0154461 A1 | 7/2005 | Humphreys et al. |
| 2005/0154465 A1 | 7/2005 | Hodges et al. |
| 2005/0154466 A1 | 7/2005 | Humphreys et al. |
| 2005/0159818 A1 | 7/2005 | Blain |
| 2005/0171543 A1 | 8/2005 | Timm et al. |
| 2005/0171608 A1 | 8/2005 | Peterman et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0209697 A1 | 9/2005 | Paponneau et al. |
| 2005/0209698 A1 | 9/2005 | Gordon et al. |
| 2005/0222569 A1 | 10/2005 | Panjabi |
| 2005/0228500 A1 | 10/2005 | Kim et al. |
| 2005/0245930 A1 | 11/2005 | Timm et al. |
| 2005/0256578 A1 | 11/2005 | Blatt et al. |
| 2005/0273167 A1 | 12/2005 | Triplett et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288670 A1 | 12/2005 | Panjabi et al. |
| 2006/0009768 A1 | 1/2006 | Ritland |
| 2006/0009850 A1 | 1/2006 | Frigg et al. |
| 2006/0015100 A1 | 1/2006 | Panjabi et al. |
| 2006/0036240 A1 | 2/2006 | Colleran |
| 2006/0036245 A1 | 2/2006 | Stern |
| 2006/0084986 A1 | 4/2006 | Grinberg et al. |
| 2006/0089717 A1 | 4/2006 | Krishna et al. |
| 2006/0095132 A1 | 5/2006 | Kirschman |
| 2006/0129244 A1 | 6/2006 | Ensign |
| 2006/0142759 A1 | 6/2006 | Arnin et al. |
| 2006/0149228 A1 | 7/2006 | Schlapfer et al. |
| 2006/0149229 A1 | 7/2006 | Kwak et al. |
| 2006/0149278 A1 | 7/2006 | Abdou |
| 2006/0149383 A1 | 7/2006 | Arnin et al. |
| 2006/0155377 A1 | 7/2006 | Beaurain et al. |
| 2006/0167547 A1 | 7/2006 | Suddaby |
| 2006/0189983 A1 | 8/2006 | Fallin et al. |
| 2006/0195114 A1 | 8/2006 | Bertagnoli |
| 2006/0195191 A1 | 8/2006 | Sweeney et al. |
| 2006/0195192 A1 | 8/2006 | Gordon et al. |
| 2006/0217712 A1 | 9/2006 | Mueller et al. |
| 2006/0229729 A1 | 10/2006 | Gordon |
| 2006/0241642 A1 | 10/2006 | Arnin et al. |
| 2006/0241769 A1 | 10/2006 | Gordon et al. |
| 2006/0241770 A1 | 10/2006 | Rhoda et al. |
| 2006/0241771 A1 | 10/2006 | Gordon et al. |
| 2006/0247635 A1 | 11/2006 | Gordon et al. |
| 2006/0247779 A1 | 11/2006 | Gordon et al. |

| | | | |
|---|---|---|---|
| 2006/0260483 | A1 | 11/2006 | Hartmann et al. |
| 2006/0264937 | A1 | 11/2006 | White |
| 2006/0265068 | A1 | 11/2006 | Schwab |
| 2006/0265074 | A1 | 11/2006 | Krishna |
| 2007/0010886 | A1 | 1/2007 | Banick |
| 2007/0073405 | A1 | 3/2007 | Verhulst et al. |
| 2007/0073406 | A1 | 3/2007 | Gordon et al. |
| 2007/0093828 | A1 | 4/2007 | Abdou |
| 2007/0093846 | A1 | 4/2007 | Frigg et al. |
| 2007/0162137 | A1 | 7/2007 | Kloss et al. |
| 2007/0213720 | A1 | 9/2007 | Gordon et al. |
| 2007/0213821 | A1 | 9/2007 | Kwak et al. |
| 2007/0225814 | A1 | 9/2007 | Atkinson |
| 2007/0239279 | A1 | 10/2007 | Francis |
| 2007/0270838 | A1 * | 11/2007 | Bruneau et al. .............. 606/61 |
| 2007/0270972 | A1 | 11/2007 | Gordon et al. |
| 2007/0288094 | A1 | 12/2007 | Krishna et al. |
| 2008/0015702 | A1 | 1/2008 | Lakin et al. |
| 2008/0027547 | A1 | 1/2008 | Yu et al. |
| 2008/0033562 | A1 | 2/2008 | Krishna |
| 2008/0065079 | A1 | 3/2008 | Bruneau et al. |
| 2008/0133013 | A1 | 6/2008 | Duggal et al. |
| 2008/0161853 | A1 | 7/2008 | Arnold et al. |
| 2008/0177310 | A1 | 7/2008 | Reiley |
| 2008/0234732 | A1 | 9/2008 | Landry et al. |
| 2008/0234740 | A1 | 9/2008 | Landry et al. |
| 2008/0234741 | A1 | 9/2008 | Landry et al. |
| 2008/0234764 | A1 | 9/2008 | Landry et al. |
| 2008/0234823 | A1 | 9/2008 | Landry et al. |
| 2008/0300685 | A1 | 12/2008 | Carls et al. |
| 2008/0312692 | A1 | 12/2008 | Brennan et al. |
| 2009/0005817 | A1 | 1/2009 | Friedrich et al. |
| 2009/0076549 | A1 | 3/2009 | Lim et al. |
| 2009/0093846 | A1 | 4/2009 | Hestad |
| 2009/0105758 | A1 | 4/2009 | Gimbel et al. |
| 2009/0105759 | A1 | 4/2009 | Gimbel et al. |
| 2009/0105764 | A1 | 4/2009 | Jackson |
| 2009/0105820 | A1 | 4/2009 | Jackson |
| 2009/0105827 | A1 | 4/2009 | Gimbel et al. |
| 2009/0105828 | A1 | 4/2009 | Gimbel et al. |
| 2009/0105829 | A1 | 4/2009 | Gimbel et al. |
| 2009/0143862 | A1 | 6/2009 | Trieu |
| 2009/0177196 | A1 | 7/2009 | Zlock et al. |
| 2010/0174317 | A1 | 7/2010 | Timm et al. |
| 2010/0222819 | A1 | 9/2010 | Timm et al. |
| 2010/0331985 | A1 | 12/2010 | Cordon et al. |
| 2011/0196428 | A1 | 8/2011 | Panjabi et al. |
| 2012/0143254 | A1 | 6/2012 | Gimbel et al. |
| 2012/0245689 | A1 | 9/2012 | Gimbel et al. |

FOREIGN PATENT DOCUMENTS

| | | |
|---|---|---|
| FR | 2718946 | 10/1995 |
| FR | 2745706 | 9/1997 |
| FR | 2799949 | 4/2001 |
| RU | 2085145 | 7/1997 |
| WO | 9641582 | 12/1996 |
| WO | 9848739 | 11/1998 |
| WO | 0004851 | 2/2000 |
| WO | 0074606 | 12/2000 |
| WO | 0101893 | 1/2001 |
| WO | 0156513 | 8/2001 |
| WO | 0245625 | 6/2002 |
| WO | 2004019762 | 3/2004 |
| WO | 2004019828 | 3/2004 |
| WO | 2004019830 | 3/2004 |
| WO | 2004024011 | 3/2004 |
| WO | 2004026188 | 4/2004 |
| WO | 2004041129 | 5/2004 |
| WO | 2004054479 | 7/2004 |
| WO | 2005016194 | 2/2005 |
| WO | 2005067824 | 7/2005 |
| WO | 2005070349 | 8/2005 |
| WO | 2005117725 | 12/2005 |
| WO | WO 2005117725 | 12/2005 |
| WO | 2006066198 | 6/2006 |
| WO | 2006116851 | 11/2006 |
| WO | 2007104024 | 9/2007 |
| WO | 2008089350 | 7/2008 |

OTHER PUBLICATIONS

U.S. Patent and Trademark Office "Communication" for U.S. Appl. No. 11/134,055, mailed Jan. 19, 2010.
U.S. Patent and Trademark Office "Communication" for U.S. Appl. No. 11/134,073, mailed Jan. 27, 2010.
U.S. Patent and Trademark Office "Communication" for U.S. Appl. No. 11/134,091, mailed Jan. 26, 2010.
U.S. Patent and Trademark Office "Communication" for U.S. Appl. No. 11/371,182, mailed Feb. 8, 2010.
U.S. Patent and Trademark Office "Communication" for U.S. Appl. No. 11/134,066, mailed Feb. 18, 2010.
U.S. Patent and Trademark Office "Communication" for U.S. Appl. No. 11/134,079, mailed Feb. 19, 2010.
U.S. Patent and Trademark Office "Communication" for U.S. Appl. No. 11/134,067, mailed Feb. 18, 2010.
U.S. Patent and Trademark Office "Communication" for U.S. Appl. No. 10/777,411, mailed Mar. 5, 2010.
U.S. Patent and Trademark Office "Communication" for U.S. Appl. No. 11/050,632, mailed Mar. 2, 2010.
U.S. Patent and Trademark Office "Communication" for U.S. Appl. No. 11/371,190, mailed Feb. 26, 2010.
U.S. Patent and Trademark Office "Communication" for U.S. Appl. No. 11/134,082, mailed Mar. 12, 2010.
U.S. Patent and Trademark Office "Communication" for U.S. Appl. No. 11/134,069, mailed Dec. 30, 2009.
U.S. Patent and Trademark Office "Communication" for U.S. Appl. No. 11/371,170, mailed May 4, 2010.
U.S. Patent and Trademark Office "Communication" for U.S. Appl. No. 11/371,376, mailed May 26, 2010.
U.S. Patent and Trademark Office "Communication" for U.S. Appl. No. 11/526,849, mailed Jun. 1, 2010.
U.S. Patent and Trademark Office "Communication" for U.S. Appl. No. 11/655,790, mailed Mar. 15, 2010.
U.S. Patent and Trademark Office "Communication" for U.S. Appl. No. 11/134,069, mailed Apr. 19, 2010.
U.S. Patent and Trademark Office "Communication" for U.S. Appl. No. 11/371,188, mailed Apr. 28, 2010.
U.S. Patent and Trademark Office "Communication" for U.S. Appl. No. 11/371,181, mailed Jun. 9, 2008.
U.S. Patent and Trademark Office "Communication" for U.S. Appl. No. 11/371,190, mailed Apr. 17, 2008.
U.S. Patent and Trademark Office "Communication" for U.S. Appl. No. 11/371,188, mailed Mar. 17, 2009.
U.S. Patent and Trademark Office "Communication" for U.S. Appl. No. 11/371,182, mailed Oct. 11, 2007.
U.S. Patent and Trademark Office "Communication" for U.S. Appl. No. 11/371,182, mailed Jun. 9, 2008.
U.S. Patent and Trademark Office "Communication" for U.S. Appl. No. 11/371,182, mailed Dec. 12, 2008.
U.S. Patent and Trademark Office "Communication" for U.S. Appl. No. 11/371,182, mailed Mar. 25, 2009.
U.S. Patent and Trademark Office "Communication" for U.S. Appl. No. 11/371,182, mailed Apr. 24, 2009.
U.S. Patent and Trademark Office "Communication" for U.S. Appl. No. 11/371,376, mailed Apr. 20, 2009.
U.S. Patent and Trademark Office "Communication" for U.S. Appl. No. 11/371,328, mailed Mar. 17, 2009.
U.S. Patent and Trademark Office "Communication" for U.S. Appl. No. 11/371,190, mailed Aug. 11, 2008.
U.S. Patent and Trademark Office "Communication" for U.S. Appl. No. 11/655,724, mailed May 27, 2009.
U.S. Patent and Trademark Office "Communication" for U.S. Appl. No. 11/655,787, mailed May 27, 2009.
U.S. Patent and Trademark Office "Communication" for U.S. Appl. No. 11/655,737, mailed May 27, 2009.
U.S. Patent and Trademark Office "Communication" for U.S. Appl. No. 11/655,723, mailed May 27, 2009.
U.S. Patent and Trademark Office "Communication" for U.S. Appl. No. 11/655,790, mailed Jun. 4, 2009.
U.S. Patent and Trademark Office "Communication" for U.S. Appl. No. 11/134,082, mailed May 25, 2010.

U.S. Patent and Trademark Office "Communication" for U.S. Appl. No. 10/777,411, mailed Jun. 9, 2010.
U.S. Patent and Trademark Office "Communication" for U.S. Appl. No. 11/371,328, mailed Jun. 17, 2010.
U.S. Patent and Trademark Office "Communication" for U.S. Appl. No. 11/371,188, mailed Jun. 15, 2010.
U.S. Patent and Trademark Office "Communication" for U.S. Appl. No. 11/371,182, mailed Jun. 8, 2010.
U.S. Patent and Trademark Office "Communication" for U.S. Appl. No. 11/371,182, mailed Jul. 21, 2009.
U.S. Patent and Trademark Office "Communication" for U.S. Appl. No. 11/134,073, mailed Jul. 22, 2009.
International Preliminary Report on Patentability for International Application No. PCT/US2008/051346 mailed Mar. 27, 2009, 23 pages.
International Search Report and Written Opinion for International Application No. PCT/US2008/051346 mailed Sep. 9, 2008, 20 pages.
U.S. Patent and Trademark Office "Communication" for U.S. Appl. No. 11/371,376, mailed Jul. 28, 2009.
U.S. Patent and Trademark Office "Communication" for U.S. Appl. No. 11/371,328, mailed Sep. 28, 2009.
U.S. Patent and Trademark Office "Communication" for U.S. Appl. No. 11/371,190, mailed Apr. 29, 2009.
PCT Search Report and Written Opinion for PCT/US2004/025090 mailed on Apr. 11, 2005 (23 pages).
U.S. Patent and Trademark Office "Communication" for U.S. Appl. No. 11/343,933 mailed Nov. 19, 2007.
U.S. Patent and Trademark Office "Communication" for U.S. Appl. No. 11/134,091 mailed Feb. 21, 2008.
U.S. Patent and Trademark Office "Communication" for U.S. Appl. No. 11/134,092 mailed Feb. 21, 2008.
U.S. Patent and Trademark Office "Communication" for U.S. Appl. No. 10/777,411 mailed Mar. 20, 2008.
U.S. Patent and Trademark Office "Communication" for U.S. Appl. No. 11/134,055 mailed Aug. 25, 2008.
U.S. Patent and Trademark Office "Communication" for U.S. Appl. No. 11/343,933 mailed Jun. 30, 2008.
U.S. Patent and Trademark Office "Communication" for U.S. Appl. No. 10/777,411 mailed Mar. 19, 2007.
U.S. Patent and Trademark Office "Communication" for U.S. Appl. No. 10/777,411 mailed Sep. 24, 2007.
U.S. Patent and Trademark Office "Communication" for U.S. Appl. No. 10/777,411 mailed Aug. 29, 2008.
U.S. Patent and Trademark Office "Communication" for U.S. Appl. No. 10/777,411 mailed Dec. 23, 2008.
U.S. Patent and Trademark Office "Communication" for U.S. Appl. No. 11/050,632 mailed Sep. 24, 2008.
U.S. Patent and Trademark Office "Communication" for U.S. Appl. No. 11/050,632 mailed Apr. 16, 2009.
U.S. Patent and Trademark Office "Communication" for U.S. Appl. No. 11/134,066 mailed Dec. 4, 2008.
U.S. Patent and Trademark Office "Communication" for U.S. Appl. No. 11/134,091 mailed Dec. 24, 2008.
U.S. Patent and Trademark Office "Communication" for U.S. Appl. No. 11/134,069 mailed Dec. 24, 2008.
U.S. Patent and Trademark Office "Communication" for U.S. Appl. No. 11/134,069 mailed Jun. 5, 2009.
U.S. Patent and Trademark Office "Communication" for U.S. Appl. No. 11/134,082 mailed Dec. 3, 2008.
U.S. Patent and Trademark Office "Communication" for U.S. Appl. No. 11/345,602 mailed Mar. 31, 2009.
U.S. Patent and Trademark Office "Communication" for U.S. Appl. No. 10/777,411, mailed Jul. 17, 2009.
U.S. Patent and Trademark Office "Communication" for U.S. Appl. No. 11/134,079, mailed Aug. 14, 2009.
U.S. Patent and Trademark Office "Communication" for U.S. Appl. No. 11/134,082, mailed Aug. 14, 2009.
U.S. Patent and Trademark Office "Communication" for U.S. Appl. No. 11/134,067, mailed Aug. 14, 2009.
U.S. Patent and Trademark Office "Communication" for U.S. Appl. No. 11/050,632, mailed Aug. 25, 2009.
U.S. Patent and Trademark Office "Communication" for U.S. Appl. No. 11/134,066, mailed Sep. 9, 2009.
U.S. Patent and Trademark Office "Communication" for U.S. Appl. No. 11/345,602, mailed Oct. 13, 2009.
U.S. Patent and Trademark Office "Communication" for U.S. Appl. No. 11/371,170, mailed Nov. 4, 2009.
U.S. Patent and Trademark Office "Communication" for U.S. Appl. No. 11/371,190, mailed Nov. 7, 2008.
U.S. Patent and Trademark Office "Communication" for U.S. Appl. No. 11/371,190, mailed Oct. 29, 2009.
U.S. Patent and Trademark Office "Communication" for U.S. Appl. No. 10/777,411, mailed Oct. 1, 2009.
U.S. Patent and Trademark Office "Communication" for U.S. Appl. No. 11/371,376, mailed Nov. 4, 2009.
U.S. Patent and Trademark Office "Communication" for U.S. Appl. No. 11/371,376, mailed Aug. 28, 2009.
U.S. Patent and Trademark Office "Communication" for U.S. Appl. No. 11/371,188, mailed Sep. 25, 2009.
U.S. Patent and Trademark Office "Communication" for U.S. Appl. No. 11/371,182, mailed Oct. 14, 2009.
Co-pending U.S. Appl. No. 11/371,170 entitled "Dynamic Interbody Device" to Gordon et al, filed Mar. 8, 2006.
Co-pending U.S. Appl. No. 11/371,376 entitled "Artificial Functional Spinal Unit System and Method for Use" to Gordon et al, filed Mar. 8, 2006.
Co-pending U.S. Appl. No. 11/655,787 entitled "Artificial Functional Spinal Unit System and Method for Use" to Landry et al, filed Jan. 19, 2007.
Co-pending U.S. Appl. No. 11/655,723 entitled "Artificial Functional Spinal Unit System and Method for Use" to Landry et al, filed Jan. 19, 2007.
Co-pending U.S. Appl. No. 11/655,724 entitled "Artificial Functional Spinal Unit System and Method for Use" to Landry et al, filed Jan. 19, 2007.
Co-pending U.S. Appl. No. 11/655,737 entitled "Dynamic Interbody Device" to Landry et al, filed Jan. 19, 2007.
Humphreys et al., "Biomechanics of the KENTI (TM) Total Joint Replacement", Presented at the Global Symposium on Motion Preservation Technology, May 9-13, 2006; 3 pages.
Hodges et al., "Biomechanics of the KENTI (TM) Total Joint Replacement", Presented at the Global Symposium on Motion Preservation Technology, May 9-13, 2006; 1 page.
Patel et al., "Changes in Kinematics following Single Level fusion, Single and Bi-Level Charite disc replacement in the Lumbar Spine" Presented at the Global Symposium on Motion Preservation Technology, May 9-13, 2006; 1 page.
Serhan et al. "Biomechanics of the posterior lumbar articulating elements," Neurosurg Focus 2007, 22(1):E1, 6 pages.
Khoueir et al. "Classification of posterior dynamic stabilization devices," Neurosurg Focus, 2007, 22(1):E1, 8 pages.
U.S. Patent and Trademark Office "Communication" for U.S. Appl. No. 11/371,190, mailed Oct. 11, 2007.
U.S. Patent and Trademark Office "Communication" for U.S. Appl. No. 11/371,376, mailed Nov. 29, 2007.
U.S. Patent and Trademark Office "Communication" for U.S. Appl. No. 11/371,181, mailed Oct. 11, 2007.
Co-pending U.S. Appl. No. 11/975,921 entitled "Posterior Stabilization System With a Variable Length Elongated Member" to Gimbel et al.
Co-pending U.S. Appl. No. 11/975,918 entitled "Dampener System for a Posterior Stabilization System With a Fixed Length Elongated Member" to Gimbel et al.
PCT Search Report and Written Opinion for International Application No. PCT/US2007/063595 mailed Dec. 11, 2007, 15 pages.
Co-pending U.S. Appl. No. 11/975,920 entitled "Posterior Stabilization System With Isolated, Dual Dampener Systems" to Gimbel et al.
Co-pending U.S. Appl. No. 11/975,917 entitled "Dampener System for a Posterior Stabilization System With a Variable Length Elongated Member" to Gimbel et al.
Co-pending U.S. Appl. No. 11/975,919 entitled "Spinal Stabilization Systems With Dynamic Interbody Devices" to Gimbel et al.

Co-pending U.S. Appl. No. 11/655,790 entitled "Artificial Functional Spinal Unit System and Method for Use" to Landry et al, filed Jan. 19, 2007.
U.S. Patent and Trademark Office "Communication" for U.S. Appl. No. 11/655,724, mailed Nov. 23, 2009.
U.S. Patent and Trademark Office "Communication" for U.S. Appl. No. 11/655,787, mailed Nov. 23, 2009.
U.S. Patent and Trademark Office "Communication" for U.S. Appl. No. 11/655,737, mailed Nov. 23, 2009.
U.S. Patent and Trademark Office "Communication" for U.S. Appl. No. 11/655,723, mailed Nov. 24, 2009.
U.S. Patent and Trademark Office "Communication" for U.S. Appl. No. 11/371,376, mailed Jul. 29, 2010.
U.S. Patent and Trademark Office "Communication" for U.S. Appl. No. 11/371,190, mailed Aug. 11, 2010.
U.S. Patent and Trademark Office "Communication" for U.S. Appl. No. 11/134,091, mailed Aug. 4, 2010.
U.S. Patent and Trademark Office "Communication" for U.S. Appl. No. 11/975,916, mailed Aug. 4, 2010.
U.S. Patent and Trademark Office "Communication" for U.S. Appl. No. 11/975,917, mailed Aug. 17, 2010.
U.S. Patent and Trademark Office "Communication" for U.S. Appl. No. 11/975,919, mailed Aug. 19, 2010.
U.S. Patent and Trademark Office "Communication" for U.S. Appl. No. 11/371,182, mailed Aug. 25, 2010.
U.S. Patent and Trademark Office "Communication" for U.S. Appl. No. 11/371,188, mailed Sep. 1, 2010.
U.S. Patent and Trademark Office "Communication" for U.S. Appl. No. 10/777,411, mailed Oct. 15, 2010.
U.S. Patent and Trademark Office "Communication" for U.S. Appl. No. 11/371,170, mailed Jul. 12, 2010.
U.S. Patent and Trademark Office "Communication" for U.S. Appl. No. 11/526,849, mailed Dec. 6, 2010.
U.S. Patent and Trademark Office "Communication" for U.S. Appl. No. 11/371,328, mailed Jan. 6, 2011.
U.S. Patent and Trademark Office "Communication" for U.S. Appl. No. 11/371,170, mailed Jan. 28, 2011.
U.S. Patent and Trademark Office "Communication" for U.S. Appl. No. 11/975,916, mailed Feb. 9, 2011.
U.S. Patent and Trademark Office "Communication" for U.S. Appl. No. 11/975,917, mailed Feb. 4, 2011.
U.S. Patent and Trademark Office "Communication" for U.S. Appl. No. 11/975,919, mailed Feb. 4, 2011.
U.S. Patent and Trademark Office "Communication" for U.S. Appl. No. 11/526,849, mailed Feb. 23, 2011.
Co-pending U.S. Appl. No. 13/072,511 entitled "Interbody Device Insertion Systems and Methods" to Gimbel et al, filed Mar. 25, 2011.
U.S. Patent and Trademark Office "Communication" for U.S. Appl. No. 11/371,170, mailed May 6, 2011.
U.S.P.T.O. Notice of Allowance for U.S. Appl. No. 11/134,069, mailed Oct. 13, 2011.
U.S.P.T.O. Final Office Action for U.S. Appl. No. 11/134,055, mailed Nov. 14, 2011.
U.S.P.T.O. Non-Final Office Action for U.S. Appl. No. 12/841,792, mailed Oct. 20, 2011.
U.S.P.T.O. Notice of Allowance for U.S. Appl. No. 11/134,073, mailed Oct. 13, 2011.
U.S.P.T.O. Notice of Allowance for U.S. Appl. No. 11/134,079, mailed Nov. 25, 2011.
U.S.P.T.O. Notice of Allowance for U.S. Appl. No. 11/134,067, mailed Oct. 3, 2011.
U.S.P.T.O. Notice of Allowance for U.S. Appl. No. 11/371,170, mailed Oct. 12, 2011.
U.S.P.T.O. Notice of Allowance for U.S. Appl. No. 11/975,921, mailed Dec. 14, 2011.
U.S.P.T.O. Notice of Allowance for U.S. Appl. No. 11/975,920, mailed Nov. 16, 2011.
E.P. Communication Pursuant to Article 94(3) EPC for Application No. 08713804.6-2310 mailed Nov. 10, 2011.
U.S.P.T.O. Notice of Allowance for U.S. Appl. No. 11/134,091, mailed May 4, 2012.
U.S.P.T.O. Final Office Action for U.S. Appl. No. 12/841,792, mailed Mar. 23, 2012.
U.S.P.T.O. Non-Final Office Action for U.S. Appl. No. 11/371,376, mailed Mar. 23, 2012.
U.S.P.T.O. Notice of Allowance for U.S. Appl. No. 11/975,919, mailed May 11, 2012.
U.S.P.T.O. Non-Final Office Action for U.S. Appl. No. 13/306,535, mailed May 24, 2012.
U.S.P.T.O. Non-Final Office Action for U.S. Appl. No. 11/345,602, mailed Mar. 5, 2012.
E.P.O. Report of Deficiencies for European Application No. 07 758 171.8-2310 mailed on Feb. 13, 2012.
J.P. Notice of Reason for Refusal for Japanese Application No. 2009-546510 mailed on Mar. 6, 2012.
U.S.P.T.O. Non-Final Office Action for U.S. Appl. No. 10/634,950, mailed Dec. 1, 2005.
U.S.P.T.O. Non-Final Office Action for U.S. Appl. No. 11/655,724, mailed Feb. 17, 2012.
U.S.P.T.O. Notice of Allowance for U.S. Appl. No. 11/975,918, mailed Jan. 19, 2012.
U.S.P.T.O. Notice of Allowance for U.S. Appl. No. 11/975,917, mailed Feb. 1, 2012.
U.S.P.T.O. Final Office Action for U.S. Appl. No. 111975,919, mailed Jan. 27, 2012.
U.S.P.T.O. Final Office Action for U.S. Appl. No. 11/134,091, mailed Feb. 10, 2012.
U.S.P.T.O. Notice of Allowance for U.S. Appl. No. 11/134,082, mailed Jan. 11, 2012.
U.S.P.T.O. Advisory Action for U.S. Appl. No. 11/134,055, mailed Feb. 15, 2012.
J.P. Notice of Reason for Refusal for Japanese Application No. 2008-558536 mailed Jan. 10, 2012.
U.S.P.T.O. Advisory Action for U.S. Appl. No. 12/841,792, mailed Jul. 19, 2012.
U.S.P.T.O. Final Office Action for U.S. Appl. No. 11/345,602, mailed Aug. 13, 2012.
U.S.P.T.O. Final Office Action for U.S. Appl. No. 11/655,724, mailed Aug. 24, 2012.
U.S.P.T.O. Non-Final Office Action for U.S. Appl. No. 13/306,535, mailed Aug. 24, 2012.
Co-pending U.S. Appl. No. 13/306,535 entitled "Posterior Stabilization Systems With Shared, Dual Dampener Systems" to Gimbel et al., filed Nov. 29, 2011.
Co-pending U.S. Appl. No. 13/072,511 entitled "Instrumentation for Artificial Functional Spinal Unit System" to Gimbel et al., filed Mar. 25, 2012.
Co-pending U.S. Appl. No. 13/437,604 entitled "Method of Inserting an Expandable Intervertebral Implant Without Overdistraction" to Gordon et al., filed Apr. 2, 2012.
U.S.P.T.O. Non-Final Office Action for U.S. Appl. No. 11/975,920, mailed Jun. 7, 2011.
U.S.P.T.O. Non-Final Office Action for U.S. Appl. No. 11/975,921, mailed Jun. 9, 2011.
U.S.P.T.O. Final Office Action for U.S. Appl. No. 11/134,055, mailed Jun. 9, 2011.
U.S.P.T.O. Notice of Allowance for U.S. Appl. No. 11/371,328, mailed Jun. 23, 2011.
U.S.P.T.O. Non-Final Office Action for U.S. Appl. No. 11/975,919, mailed Jul. 21, 2011.
U.S.P.T.O. Advisory Action for U.S. Appl. No. 11/371,170, mailed Aug. 5, 2011.
U.S.P.T.O. Notice of Allowance for U.S. Appl. No. 11/655,790, mailed Feb. 4, 2011.
U.S.P.T.O. Non-Final Office Action for U.S. Appl. No. 11/975,918, mailed Aug. 15, 2011.
U.S.P.T.O. Final Office Action for U.S. Appl. No. 11/975,916, mailed Sep. 6, 2011.
U.S.P.T.O. Non-Final Office Action for U.S. Appl. No. 11/975,917, mailed Aug. 3, 2011.
U.S.P.T.O. Non-Final Office Action for U.S. Appl. No. 11/134,091, mailed Aug. 12, 2011.
U.S.P.T.O. Final Office Action for U.S. Appl. No. 11/371,376, mailed Oct. 16, 2012.
U.S.P.T.O. Notice of Allowance for U.S. Appl. No. 11/655,724, mailed Oct. 4, 2012.

U.S.P.T.O. Non-Final Office Action for U.S. Appl. No. 11/134,055, mailed Nov. 8, 2012.
E.P.O. Communication Pursuant to Article 94(3) for European Application No. 07 758 171.8-2310 mailed on Oct. 11, 2012.
J.P. Final Decision of Rejection for Japanese Application No. 2008-558536 considered by Examiner on Sep. 4, 2012.
U.S.P.T.O. Non-Final Office Action for U.S. Appl. No. 11/655,737, mailed Mar. 15, 2013.
U.S.P.T.O. Non-Final Office Action for U.S. Appl. No. 11/975,916, mailed Jan. 28, 2013.
Co-pending U.S. Appl. No. 13/784,224 entitled "Interbody Device Insertion Systems and Methods" to Gimbel et al., filed Mar. 4, 2013.
E.P. Communication Pursuant to Article 94(3) EPC for Application No. 08713804.6-2310 mailed Jan. 22, 2013.

* cited by examiner

POSTERIOR STABILIZATION SYSTEMS WITH SHARED, DUAL DAMPENER SYSTEMS

BACKGROUND

1. Field of the Invention

Embodiments of the invention generally relate to functional spinal implant assemblies for insertion into an intervertebral space between adjacent vertebrae of a human spine and reconstruction of the posterior elements to provide stability, flexibility, and proper biomechanical motion. More specifically, embodiments relate to spinal stabilization systems that include one or more dynamic posterior stabilization systems.

2. Description of Related Art

The human spine is a complex mechanical structure including alternating bony vertebrae and fibrocartilaginous discs that are connected by strong ligaments and supported by musculature that extends from the skull to the pelvis and provides axial support to the body. The intervertebral discs provide mechanical cushion between adjacent vertebral segments of the spinal column and generally include two basic components: the nucleus pulposus and the annulus fibrosis. The intervertebral discs are positioned between two vertebral end plates. The annulus fibrosis forms the perimeter of the disc and is a tough outer ring that binds adjacent vertebrae together. The end plates are made of thin cartilage overlying a thin layer of hard cortical bone that attaches to the spongy, cancellous bone of a vertebra. The vertebrae generally include a vertebral foramen bounded by the anterior vertebral body and the neural arch, which consists of two pedicles that are united posteriorly by the laminae. The spinous and transverse processes protrude from the neural arch. The superior and inferior articular facets lie at the root of the transverse process.

The spine is a flexible structure capable of a high degree of curvature and twist in nearly every direction. The motion segment or functional spinal unit (FSU) is the basic motion unit of the lumbar spine. The anterior elements of the FSU include the vertebral bodies, the intervertebral disc, and the connecting soft tissues and ligaments. The posterior elements of the FSU include the bony ring created by the pedicles and lamina, the facet joints, and the connecting soft tissues and ligaments. The facet joints are located on both sides at the junction of superior and inferior bony projections of the posterior elements.

The total motion of the spine results from the cumulative motion of the individual FSUs. Each motion segment allows rotational motion in three directions (flexion-extension, lateral bending, and axial rotation) and translational motion in three directions (anterior-posterior, medial-lateral, and superior-inferior). The available motion is primarily governed by the intervertebral disc, facet joints, and ligaments. Typical maximum amounts of lumbar rotation are up to about 17° of flexion-extension, 6° of lateral bending, and 3° of axial rotation. Moderate motions of the spine during everyday living may result in less than 10° of flexion-extension.

Translation of one vertebral body with respect to an adjacent vertebral body can be up to a few millimeters during rotation. The quality of the motion is described by the shape of the motion segment moment-rotation curve. The motion segment moment-rotation curve is the rotational response of the FSU due to loading away from the center of rotation. The moment-rotation curves are non-linear with an initial low stiffness region, followed by a higher stiffness region. The initial region of high flexibility, where spinal motion is produced with less resistance to bending moments, is typically referred to as the neutral zone. Typically, the neutral zone ranges from 10-50% of the total range of motion. The stiffness (Nm/deg) in the neutral zone is about 10-30% of the high stiffness region. Alterations to the FSU caused by surgical intervention, degeneration, acute injury, or other factors are thought to change this non-linear behavior.

Genetic or developmental irregularities, trauma, chronic stress, and degenerative wear can result in spinal pathologies for which surgical intervention may be necessary. In cases of deterioration, disease, or injury, an intervertebral disc, or a portion of the intervertebral disc, may be removed from the human spine during a discectomy.

After some discectomies, one or more non-dynamic intervertebral devices may be placed in the disc space to fuse or promote fusion of the adjacent vertebrae. During some procedures, fusion may be combined with posterior fixation to address intervertebral disc and/or facet problems. The fusion procedure (e.g., posterior lumbar interbody fusion) and the posterior fixation procedure may be performed using a posterior approach. The posterior fixation and non-dynamic intervertebral devices may cooperate to inhibit motion and promote bone healing. Fusing two vertebrae together results in some loss of motion. Fusing two vertebrae together may also result in the placement of additional stress on one or more adjacent functional spinal units. The additional stress may cause deterioration of an adjacent functional spinal unit that may result in the need for an additional surgical procedure or procedures.

After some discectomies, a dynamic intervertebral device (DID) may be placed in the disc space. The DID may allow for movement of adjacent vertebrae coupled to the DID relative to each other. U.S. Pat. No. 4,863,477 to Monson, which is incorporated herein by reference, discloses a resilient dynamic device intended to replace the resilience of a natural human spinal disc. U.S. Pat. No. 5,192,326 to Bao et al., which is incorporated herein by reference, describes a prosthetic nucleus for replacing just the nucleus portion of a human spinal disc. U.S. Patent Application Publication No. 2005/0021144 to Malberg et al., which is incorporated herein by reference, describes an expandable spinal implant. Allowing for movement of the vertebrae coupled to the disc prosthesis may promote the distribution of stress that reduces or eliminates the deterioration of adjacent functional spinal units.

An intervertebral device may be positioned between vertebrae using a posterior approach, an anterior approach, a lateral approach, or other type of approach. A challenge of positioning a device between adjacent vertebrae using a posterior approach is that a device large enough to contact the end plates and slightly expand the space must be inserted through a limited space. This challenge is often further heightened by the presence of posterior osteophytes, which may cause "fish mouthing" of the posterior vertebral end plates and result in very limited access to the disc. A further challenge in degenerative disc spaces is the tendency of the disc space to assume a lenticular shape, which may require a larger implant than can be easily introduced without causing trauma to adjacent nerve roots. The size of rigid devices that may safely be introduced into the disc space is thereby limited. During some spinal fusion procedures using a posterior approach, two implants are inserted between the vertebrae. During some posterior procedures, one or both facet joints between the vertebrae may be removed to provide additional room for the insertion of a fusion device. Removal of the facet may also allow for the removal of soft tissue surrounding the facet (for example, the facet capsule) that work to resist posterior distraction.

The anterior approach poses significant challenges as well. Though the surgeon may gain very wide access to the interbody space from the anterior approach, this approach has its own set of complications and limitations. The retroperitoneal approach usually requires the assistance of a surgeon skilled in dealing with the visceral contents and the great vessels. The spine surgeon has extremely limited access to the nerve roots and no ability to access or replace the facet joints. Complications of the anterior approach that are approach specific include retrograde ejaculation, ureteral injury, and great vessel injury. Injury to the great vessels may result in massive blood loss, postoperative venous stasis, limb loss, or death. The anterior approach is more difficult in patients with significant obesity and may be virtually impossible in the face of previous retroperitoneal surgery.

Despite the difficulties of the anterior approach, the anterior approach does allow for the wide exposure needed to place a large device. In accessing the spine anteriorly, one of the major structural ligaments, the anterior longitudinal ligament, must be completely divided. A large amount of anterior annulus must also be removed along with the entire nucleus. Once these structures have been resected, the vertebral bodies may need to be over distracted to place the device within the disc space and restore disc space height. Failure to adequately tension the posterior annulus and ligaments increases the risk of device failure and/or migration. Yet in the process of placing these devices, the ligaments are overstretched while the devices are forced into the disc space under tension. Over distraction can damage the ligaments and the nerve roots. The anterior disc replacement devices currently available or in clinical trials may be too large to be placed posteriorly, and may require over distraction during insertion to allow the ligaments to hold them in position.

A facet joint or facet joints of a functional spinal unit may be subjected to deterioration, disease or trauma that requires surgical intervention. Disc degeneration is often coupled with facet degeneration, so that disc replacement only may not be sufficient treatment for a large group of patients.

Facet degeneration may be addressed using a posterior approach. Thus a second surgical approach may be required if the disc degeneration is treated using an anterior approach. The need to address facet degeneration has led to the development of facet replacement devices. Some facet replacement devices are shown in U.S. Pat. Nos. 6,419,703 to Fallin et al.; 6,902,580 to Fallin et al.; 6,610,091 to Reiley; 6,811, 567 to Reiley; and 6,974,478 to Reiley et al, each of which is incorporated herein by reference. The facet replacement devices may be used in conjunction with anterior disc replacement devices, but the facet replacement devices are not designed to provide a common center of rotation with the anterior disc replacement devices. The use of an anterior disc replacement device that has a fixed center of rotation contrary to the fixed center of rotation of the facet replacement device may restrict or diminish motion and be counterproductive to the intent of the operation.

During some spinal stabilization procedures a posterior fixation system may be coupled to the spine. During some procedures, posterior fixation systems may be coupled to each side of the spine. The posterior fixation systems may include elongated members that are coupled to vertebrae by fasteners (e.g., hooks and screws). One or more transverse connectors may be connected to the posterior fixation systems to join and stabilize the posterior fixation systems.

During some spinal stabilization procedures, dynamic posterior stabilization systems may be used. U.S. Patent Publication Nos. 2005/0182409 to Callahan et al.; 2005/0245930 to Timm et al.; and 2006/0009768 to Ritland, each of which is incorporated herein by reference, disclose dynamic posterior stabilization systems.

During some spinal stabilization procedures, a dynamic interbody device or devices may be used in conjunction with one or more dynamic posterior stabilization systems. U.S. Patent Publication No. 2006/0247779 to Gordon et al., and U.S. patent application Ser. No. 11/655,724 to Landry et al., each of which is incorporated herein by reference, disclose dynamic interbody devices and dynamic posterior stabilization systems that may be used together to stabilize a portion of a spine.

A portion of the load applied to a spine of a patient may apply shear forces to dynamic interbody devices positioned between vertebrae. In some spinal stabilization systems, shear forces applied to the dynamic interbody devices are resisted by rod and pedicle screw constructs. The shear forces may apply large moments to the pedicle screws through the rods that result in undesired loosening of the pedicle screws. In some embodiments, the pedicle screw and rod constructs are relatively massive constructs to accommodate applied shear loads without loosening.

The width of fusion devices or dynamic devices that are installed using a posterior approach may be limited by the available insertion space and/or the need to limit retraction of neural structures exiting the vertebrae being stabilized. Subsidence of the lower vertebra caused by a fusion device or dynamic device inserted using a posterior approach has been noted in some patients. Subsidence may be due to small contact area between the vertebra and the device and/or by limited or no contact of the device over cortical bone surrounding the end plate of the vertebra. The contact surfaces of many fusion devices and/or dynamic interbody devices that are inserted using posterior approaches have substantially the same contact area against the upper vertebra and the lower vertebra being stabilized.

Prosthetic replacement of the intervertebral disc accompanied by removal of the facet joints may require a dynamic stabilization system that replicates the physiological function of the removed or replaced structures. Dynamic stabilization devices are typically attached to or placed between the posterior elements of adjacent spinal units. A large number of dynamic stabilization devices have been previously proposed to protect the spine from abnormal motion or loading, but it would be a great advance in the art to provide a dynamic stabilization system that physiologically controls the pattern and magnitude of motion.

SUMMARY

In an embodiment, a posterior stabilization system may be secured to a first vertebra and a second vertebra of a human spine to stabilize the vertebrae and provide resistance to movement of the vertebrae relative to each other. The posterior stabilization system may include bone fastener and a dampener system. The dampener system may include a first dampener set and a second dampener set. The first dampener set may be compressed when the first bone fastener moves towards the second bone fastener and the second dampener set is not subjected to additional compression. The first dampener set and the second dampener set may be compressed when the first bone fastener moves away from second bone fastener.

In an embodiment, a dynamic stabilization system for a human spine is provided. The dynamic stabilization system comprises a first bone fastener configured to couple to a first vertebra, a second bone fastener configured to couple to a second vertebra, and a dampener system. The dampener system comprises a first portion configured to couple to the first bone fastener, a first dampener set, a second dampener set, and a member positioned between the first dampener set and the second dampener set. The member is configured to couple to the second bone fastener. Compression of the first dampener set provides resistance to movement of the first bone fastener towards the second bone fastener. Compression of the first dampener set and the second dampener set provides resistance to movement of the first bone fastener away from the second bone fastener.

In an embodiment, the dynamic stabilization system comprises a first bone fastener configured to couple to a first vertebra, a second bone fastener configured to couple to a second vertebra, and a dampener system. The dampener system comprises a variable length elongated member configured to couple to the first bone fastener; a member configured to couple to the variable length elongated member and the second bone fastener; a first dampener set coupled to the variable length elongated member on a first side of the member; and a second dampener set coupled to the variable length elongated member on a second side of the member. The first dampener set is configured to compress to provide resistance to movement of the first bone fastener towards the second bone fastener. The first dampener set and the second dampener set are configured to compress to provide resistance to movement of the first bone fastener away from the second bone fastener.

A method is disclosed for stabilizing a portion of a human spine. The method comprises securing a first bone fastener to a first vertebra, securing a second bone fastener to a second vertebra, and attaching a dampener system to the first bone fastener and the second bone fastener. The dampener system comprises a first dampener set and a second dampener set positioned on an elongated member. Compression of the first dampener set provides resistance to movement of the first bone fastener towards the second bone fastener. Compression of the first dampener set and the second dampener set provides resistance to movement of the first bone fastener away from the second bone fastener. The method may also comprise securing at least one dynamic interbody device between the first vertebra and the second vertebra.

BRIEF DESCRIPTION OF THE DRAWINGS

Advantages of the present invention will become apparent to those skilled in the art with the benefit of the following detailed description and upon reference to the accompanying drawings in which:

FIG. 69 depicts a perspective view of a dynamic posterior stabilization system compressed as if vertebrae coupled to the system were subjected to extension and/or lateral bending towards the side that the system is coupled to.

FIG. 70 depicts a perspective view of a dynamic posterior stabilization system compressed as if vertebrae coupled to the system were subjected to flexion and/or lateral bending away from the side that the system is coupled to.

Figure 1:
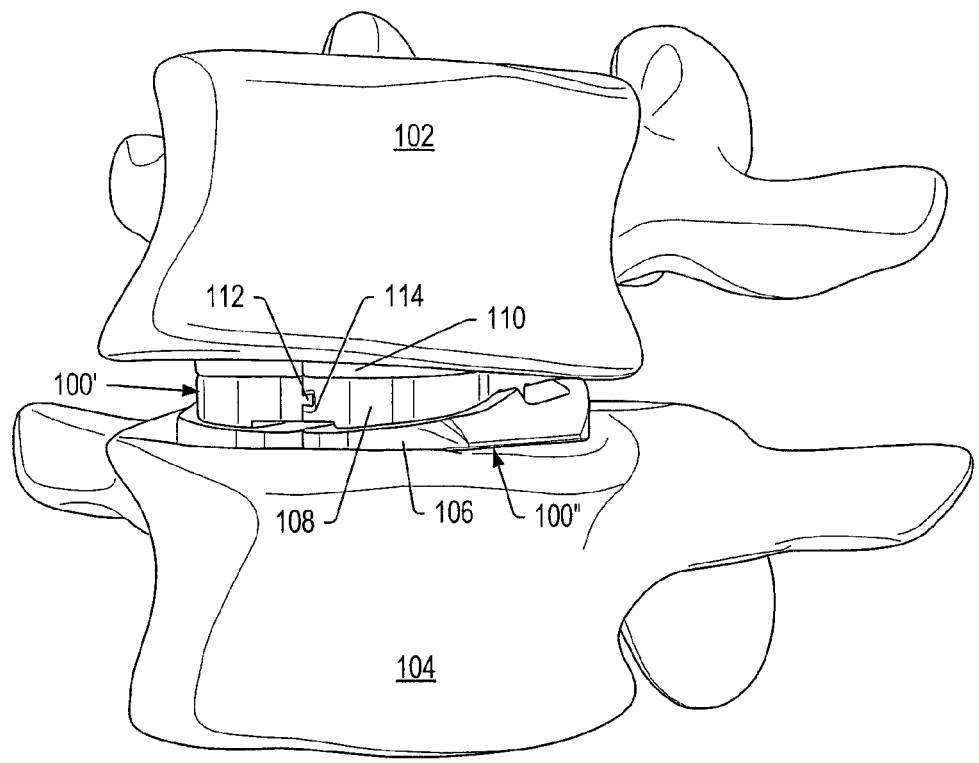
FIG. 1 depicts embodiments of dynamic interbody devices positioned between vertebrae.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

A "functional spinal unit" generally refers to a motion segment of a spine. The functional spinal unit may include two vertebrae, an intervertebral disc between the vertebrae, and the two facet joints between the vertebrae. An "artificial functional spinal unit" refers to a functional spinal unit where one or more of the components of the functional spinal unit are replaced by implants or devices that permit at least some motion of the spine. At least a portion of the intervertebral disc and/or one or both of the facet joints may be replaced by implants or devices during a spinal stabilization procedure.

As used herein, "coupled" includes a direct or indirect joining or touching unless expressly stated otherwise. For example, a first member is coupled to a second member if the first member contacts the second member, or if a third member is positioned between the first member and the second member.

A "dynamic interbody device" generally refers to an artificial intervertebral implant that allows for flexion/extension, lateral bending and/or axial rotation of vertebrae coupled to the device. The dynamic interbody device may replace a portion or all of an intervertebral disc. In some embodiments, a pair of dynamic interbody devices are installed during a spinal stabilization procedure. In some embodiments, one or more dynamic interbody devices are installed using a posterior approach. In other embodiments, a dynamic interbody device may be installed using an anterior approach or other type of approach. In some embodiments, one or more dynamic interbody devices are placed in a disc space between vertebrae, and at least one posterior stabilization system is coupled to the vertebrae. In some embodiments, one or more dynamic interbody devices are placed in the disc space without coupling a posterior stabilization system to the vertebrae.

In some embodiments, the dynamic interbody device is a bimodal device. Bimodal refers to a device that has at least two separate curved surfaces to accommodate flexion/extension with lateral bending and/or axial rotation.

Dynamic interbody devices may have surfaces that contact vertebrae. In some embodiments, a surface of the dynamic interbody device that contacts a vertebra may include one or more keels, protrusions, and/or osteoconductive/osteoinductive layers or coatings. A keel of the dynamic interbody device may be positioned in a channel formed in a vertebra. The channel may be formed in the vertebra so that the dynamic interbody device will be positioned at a desired location when inserted into the patient. Protrusions of the dynamic interbody device may penetrate an endplate of the vertebra to secure the dynamic interbody device to the vertebra. An osteoconductive/osteoinductive layer may promote bone growth that secures the dynamic interbody device to the vertebra. The osteoconductive/osteoinductive layer may include, but is not limited to a scaffold, a roughened surface, a surface treated with a titanium plasma spray, bone morphogenic proteins, and/or hydroxyapatite. A roughened surface may be formed by chemical etching, by surface abrading, by shot peening, by an electrical discharge process, and/or by embedding particles in the surface.

An anterior end of a dynamic interbody device may have a height that is greater than the height of a posterior end of the dynamic interbody device. The difference in heights between the anterior end and the posterior end of the dynamic interbody device may provide the patient with a desired amount of lordosis. Dynamic interbody devices that provide different amounts of lordosis may be provided in an instrument kit supplied for a spinal stabilization procedure. For example, the instrument kit for a posterior spinal stabilization procedure may include pairs of dynamic interbody devices that establish 0°, 3°, 6°, 9°, 12° or 15° of lordosis. Other dynamic interbody device lordosis angles or lordosis angle ranges may be provided. The amount of lordosis provided by a dynamic interbody device may be printed or etched on a visible surface of the dynamic interbody device. Other information may also be printed or etched on the visible surface of the dynamic interbody device. Such information may include dimension information (e.g., length, width, and/or height) and whether the dynamic interbody device is to be installed on the left side of the patient or the right side of the patient.

In some embodiments, one or more dynamic interbody devices are installed in a disc space formed between vertebrae during a spinal stabilization procedure. The shape and/or size of a dynamic interbody device may depend on a number of factors including surgical approach employed for insertion, intended position in the spine (e.g., cervical or lumbar), and patient anatomy. A dynamic interbody device for the lumbar spine may have a height that is less than about 22 mm. Several sizes of interbody devices may be provided in the instrument kit for the spinal stabilization procedure. In an embodiment, dynamic interbody devices having heights of 6 mm, 8 mm, 10 mm, 12, mm, 14 mm, 16 mm, 18 mm, and 20 mm are provided in the instrument kit for the spinal stabilization procedure. In an embodiment, dynamic interbody devices having heights of 7 mm, 8 mm, 9 mm, 10 mm, 12 mm and 14 mm are provided. Other sizes and/or different height ranges of dynamic interbody devices may be provided in the instrument kit for the spinal stabilization procedure. The dynamic interbody devices may include indicia indicating the height of the spinal stabilization devices.

The dynamic interbody devices may allow for flexion/extension. The dynamic interbody device may allow for a maximum of about 20° of flexion from the neutral position. The dynamic interbody device may be designed so that the dynamic interbody device has a smaller or a larger maximum angle of flexion from the neutral position. In some embodiments, the dynamic interbody device allows for a maximum of about 7° of flexion from the neutral position. In some embodiments, the maximum amount of flexion allowed by the dynamic interbody device is substantially the same as the maximum amount of extension allowed by the dynamic interbody device. In some embodiments, the maximum amount of flexion allowed by the dynamic interbody device is different from the maximum amount of extension. For example, an embodiment of a dynamic interbody device allows for a maximum of about 15° of flexion and a maximum of about 10° of extension.

The total flexion-extension range of motion may vary with implant height. Shorter dynamic interbody devices may have smaller ranges of motion than taller dynamic interbody devices. For example, a 7 mm dynamic interbody device may have a flexion-extension range of motion of about 17°, and a 14 mm dynamic interbody device may have a flexion-extension range of motion of about 23°. The minimum desirable range of motion may be ±2.5° since the prevalence of adjacent level degeneration after total disc replacement has been shown to be lower in patients with greater than 5° of motion. The 7 mm dynamic interbody device with the flexion-extension range of motion of about 17° may be able to accommodate an angle between adjacent vertebral body endplates of about 11.5° without additional built in lordotic angle. The 14 mm dynamic interbody device with the flexion-extension range of motion of about 23° may be able to accommodate an angle between adjacent vertebral body endplates of about 17.5° without additional built in lordotic angle. Such dynamic interbody devices may allow for sufficient lordotic alignment since the intervertebral body angles are approximately 8.5° at the L3-L4 level, 13° at the L4-L5 level, and 14.5° at the L5-S1 level.

The dynamic interbody device may allow for up to about 5° of axial rotation of vertebrae coupled to the dynamic interbody device (e.g. ±2.5° of rotation from a neutral position). The dynamic interbody device may allow for more or less axial rotation. In an embodiment, the dynamic interbody device allows for about ±1.5° of axial rotation of vertebrae coupled to the dynamic interbody device from a neutral position.

The dynamic interbody device may allow for up to about 10° of lateral bending of vertebrae coupled to the dynamic interbody device (e.g. ±5° of lateral bending from a neutral position). The dynamic interbody device may allow for more or less lateral bending. In an embodiment, the dynamic interbody device allows for about ±3° of lateral bending of vertebrae coupled to the dynamic interbody device from a neutral position.

The dynamic interbody device may allow for coupled lateral bending and axial rotation so that axial rotation causes some lateral bending and lateral bending causes some axial rotation. The dynamic interbody device may be formed so that a set amount of lateral bending results in a set amount of axial rotation. For example, 1° of lateral bending results in about 0.5° of axial rotation (i.e. a 2:1 ratio of lateral bending to axial rotation). A 4:1, 3:1, 2.5:1, 2:1, 1.5:1, 1:1 or other ratio of lateral bending to axial rotation may be set for the dynamic interbody devices. In some embodiments, dynamic interbody devices may be designed to be positioned between two particular vertebrae (e.g., between L4 and L5, between L3 and L4, etc.). The ratio of lateral bending to axial rotation may be selected mimic the natural ratio of lateral bending to axial rotation for normal vertebrae of the same level.

In some embodiments, a pair of dynamic interbody devices may be installed between two vertebrae to establish all or a portion of a spinal stabilization system. Each dynamic interbody device of the pair of dynamic interbody devices may be installed using a posterior approach.

In some embodiments, a single dynamic interbody device may be positioned in a disc space between vertebrae. The use of a single dynamic interbody device may avoid the need to have left oriented and right oriented dynamic interbody devices. The single dynamic interbody device may be installed using an anterior approach, a posterior approach, or a different type of approach. Single dynamic interbody devices inserted using an anterior approach may be installed using installation procedures known in the art. The coupled axial rotation/lateral bending of the anterior dynamic interbody device includes the functionality of the facet joints. One or both of the facets may be removed using a simple minimally invasive procedure without the need to install a posterior stabilization system.

As used herein a "dynamic posterior stabilization system" generally refers to an apparatus used to replace or supplement a facet joint while allowing for both dynamic resistance and at least some motion of the first vertebra to be stabilized relative to the second vertebra to be stabilized. The first vertebra and the second vertebra may be vertebrae of a functional spinal unit. In some embodiments, bone fasteners of the dynamic posterior stabilization system are secured to the first vertebra and the second vertebra. In some embodiments, a bone fastener of the dynamic posterior stabilization system may be coupled to a vertebra adjacent to the vertebrae of the functional spinal unit being stabilized. The bone fasteners may be coupled to lamina, pedicles, and/or vertebral bodies of the vertebrae. In some embodiments, dynamic posterior stabilization systems may be positioned in three or more vertebrae to form a multi-level stabilization system.

The dynamic posterior stabilization system may replace or supplement a normal, damaged, deteriorated, defective or removed facet joint. The dynamic posterior stabilization system may include bone fasteners, an elongated member, and at least one bias member. The bias member may provide little or no initial resistance to movement of a first vertebra coupled to the system relative to a second vertebra coupled to the system. Resistance to additional movement of the first vertebra relative to the second vertebra may increase. The increasing resistance provided by the bias member may mimic the behavior of a normal functional spinal unit. The dynamic posterior stabilization system may stabilize the vertebrae, limit the range of motion of the first vertebra relative to the second vertebra, and/or share a portion of the load applied to the vertebrae.

The dynamic posterior stabilization systems disclosed herein may allow for rotational and/or translational motion of an elongated member (e.g., a rod or plate) relative to one or more bone fasteners. The bone fasteners may include threading, barbs, rings or other protrusions that secure the bone fasteners to vertebrae. In some embodiments, the bone fasteners may be cemented or glued to the vertebrae. Bone fasteners may include collars. In some embodiments, a collar of a bone fastener is an integral portion of the bone fastener. In some embodiments, the collar is a separate component that is coupled to at least one other component of the bone fastener. The collar of the bone fastener is the portion of the bone fastener that couples to an elongated member of the dynamic posterior stabilization system. In some embodiments, the bone fasteners are polyaxial pedicle screws and the collars are the upper portions of the polyaxial pedicle screws. In some embodiments, the bone fasteners are bone screws and the collars are plates, rod holders, or other structures that are coupled to the bone screws.

During installation of dynamic interbody devices of a spinal stabilization system, or during installation of a single dynamic interbody device, one or both facet joints of the vertebrae may be removed. A dynamic posterior stabilization system may be installed to replace a removed facet joint. One or both of the dynamic interbody devices of the spinal stabilization system, or the single dynamic interbody device, may be coupled to a dynamic posterior stabilization system. Coupling a dynamic interbody device to the dynamic posterior stabilization system may inhibit backout of the dynamic interbody device from the disc space.

In some embodiments, a dynamic posterior stabilization system may be installed without removal of a facet joint. The dynamic posterior stabilization system may be installed after a discectomy, laminectomy, or other procedure. The dynamic posterior stabilization system may change the dynamic resistance that is not normal due to degeneration, disease, loss of a portion of the intervertebral disc and/or tissue damage.

A dynamic interbody device and a dynamic posterior stabilization system may include one or more biocompatible metals having a non-porous quality and a smooth finish (e.g., surgical grade stainless steel, titanium and/or titanium alloys). In some embodiments, a dynamic interbody device or dynamic posterior stabilization system may include ceramic and/or one or more other suitable biocompatible materials, such as biocompatible polymers and/or biocompatible metals. Biocompatible polymers may include, but are not limited to, polyetheretherketone resins ("PEEK"), carbon reinforced PEEK, ultra high molecular weight polyethylenes, polyethylenes, polyanhydrides, and alpha polyesters. For example, a dynamic interbody device or a dynamic posterior stabilization system may be constructed of a combination of biocompatible materials including cobalt chromium molybdenum alloy, ultra high molecular weight polyethylene, and polycarbonate—urethane or silicone blend.

Dynamic interbody devices may include surfaces that mate with complementary surfaces and allow for motion of vertebrae coupled to the dynamic interbody devices. Components or members of dynamic interbody devices may be formed using CNC (computer numerical control) machining or other techniques. Some surfaces of the dynamic interbody devices may be treated to promote movement of the surfaces and/or to inhibit galling. For example, two surfaces that move relative to each other may have mismatched hardness and/or different surface finish orientations to promote free movement of the surfaces relative to each other.

In some embodiments, dynamic interbody devices and dynamic posterior stabilization systems may be made of non-magnetic, radiolucent materials to allow unrestricted intra-operative and post-operative imaging. Certain material may interfere with x-ray and/or magnetic imaging. Magnetic materials may interfere with magnetic imaging techniques. Most non-magnetic stainless steels and cobalt chrome contain enough iron and/or nickel so that both magnetic imaging and x-ray imaging techniques are adversely affected. Other materials, such as titanium and some titanium alloys, are substantially iron free. Such materials may be used when magnetic imaging techniques are to be used, but such materials are often radio-opaque and sub-optimal for x-ray imaging techniques. Many ceramics and polymers are radiolucent and may be used with both magnetic imaging techniques and x-ray imaging techniques. The dynamic interbody devices and/or the dynamic posterior stabilization systems may include coatings and/or markers that indicate the positions of the devices and/or systems during operative and/or post-operative imaging.

In some embodiments, two dynamic interbody devices may be positioned in a disc space between two vertebrae during a spinal stabilization procedure. The largest width of each dynamic interbody device may be less than one half the width of the vertebrae the dynamic interbody devices are to be positioned between. FIG. 1 depicts embodiments of dynamic interbody devices 100', 100" that may be implanted using a posterior approach. Anterior ends and/or posterior ends of dynamic interbody devices 100', 100" may be positioned near the edge of the endplates of vertebrae 102, 104 so that the dynamic interbody devices abut strong, supportive bone of the vertebrae to be stabilized. Dynamic interbody devices 100', 100" may be bilateral devices with coupled axial rotation and lateral bending.

Figure 2:
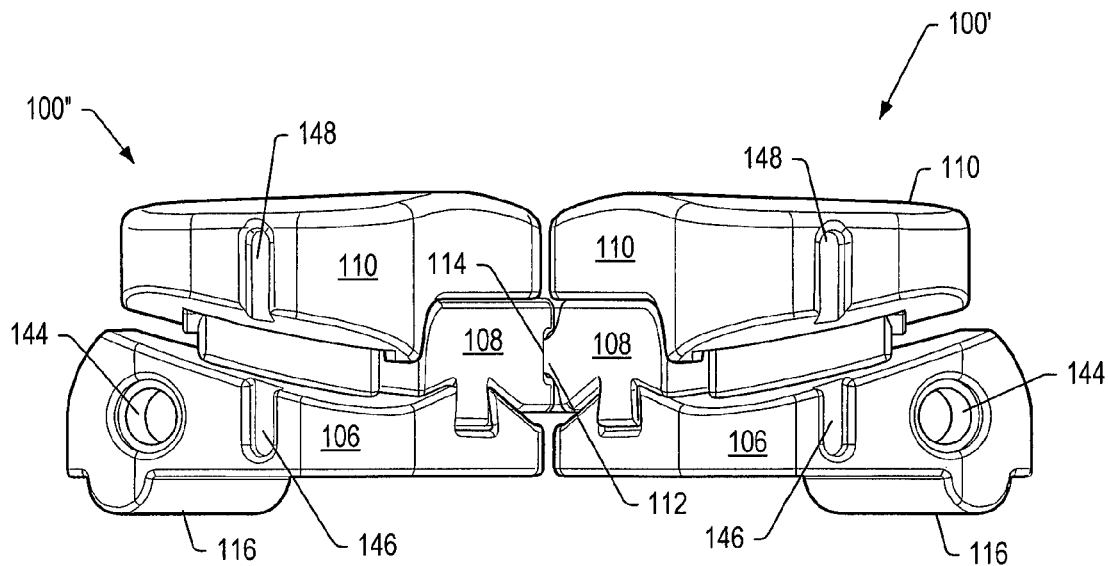
FIG. 2 depicts a rear view of dynamic interbody device embodiments.

FIG. 2 depicts a rear view of dynamic interbody devices 100', 100". Each dynamic interbody device 100' or 100" may include first member 106, second member 108 and third member 110. First members 106 may be coupled to second members 108 so that dynamic interbody devices 100', 100" accommodate lateral bending and axial rotation of vertebrae coupled to the dynamic interbody devices. In some embodiments, dynamic interbody devices 100', 100" couple lateral bending and axial motion together so that lateral bending motion causes axial rotation, and axial rotation causes lateral bending. Third members 110 may be coupled to second members 108 so that dynamic interbody device 100', 100" accommodate flexion and extension of vertebrae coupled to the dynamic interbody device. Dynamic interbody devices 100', 100" are shown in positions of neutral lateral bending, neutral axial rotation and maximum flexion in FIG. 2.

In some embodiments, the first members are coupled to the second members to allow for lateral bending without coupled axial rotation. In some embodiments, the first members are coupled to the second members to allow for axial rotation without coupled lateral bending.

In some embodiments, first member 106 of dynamic interbody device 100' may be substantially a mirror image first member 106 of dynamic interbody device 100", and third member 110 of dynamic interbody device 100' may be substantially a mirror image of third member 110 of dynamic interbody device 100". In other embodiments, the first member of dynamic interbody device 100' may have a shape that is different than the mirror image of the first member of dynamic interbody device 100" and/or the third member of dynamic interbody device 100' may have a shape that is different than the mirror image of the third member of dynamic interbody device 100".

Second member 108 of dynamic interbody device 100' may be substantially the mirror image of second member 108 of dynamic interbody device 100" with the exception of second member 108 of dynamic interbody device 100' having portion 112 that engages portion 114 of second member 108 of dynamic interbody device 100" to join dynamic interbody device 100' to dynamic interbody device 100" when the dynamic interbody devices are positioned between vertebrae. In other embodiments, first member 106 of dynamic interbody device 100' has a portion that engages a portion of first member 106 of dynamic interbody device 100" when the dynamic interbody devices are positioned between vertebrae. In other embodiments, third member 110 of dynamic interbody device 100' has a portion that engages a portion of first member 110 of dynamic interbody device 100" when the dynamic interbody devices are positioned between vertebrae.

Figure 3:
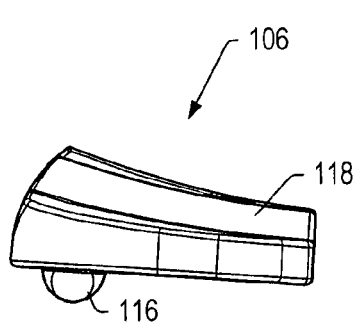
FIG. 3 depicts a front view of the first member of a dynamic interbody device embodiment.
Figure 4:
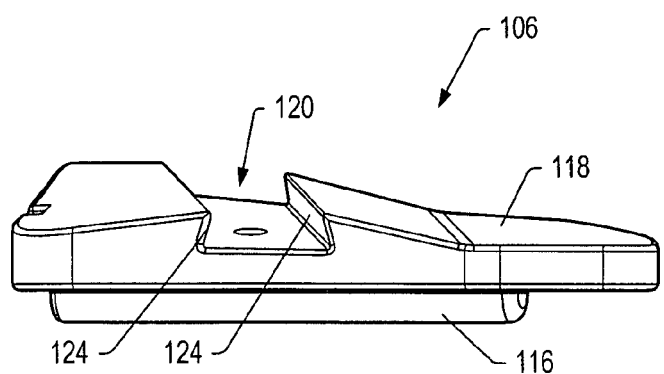
FIG. 4 depicts a side view of the first member of the dynamic interbody device embodiment.
Figure 5:
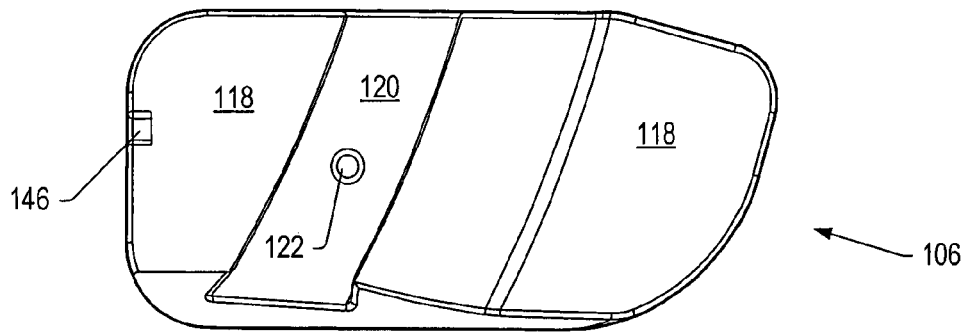
FIG. 5 depicts a top view of the first member of the dynamic interbody device embodiment.

FIG. 3 depicts a front view of first member 106 of dynamic interbody device 100'. FIG. 4 depicts a side view of first member 106 of dynamic interbody device 100'. FIG. 5 depicts a top view of first member 106 of dynamic interbody device

100′. First member 106 may include keel 116, superior surface 118, slot 120, and opening 122. Keel 116 may reside in a groove or recess formed in a vertebra when dynamic interbody device 100′ is positioned in a disc space between vertebrae. Keel 116 may inhibit undesired movement of dynamic interbody device 100′ relative to the vertebrae.

Superior surface 118 of first member 106 may be curved. The curvature of superior surface 118 may complement a curvature of an inferior surface of the second member of the dynamic interbody device to allow the dynamic interbody device to accommodate lateral bending.

First member 106 may include arcuate slot 120. Arcuate slot 120 may interact with, a complementary protrusion of the second member to allow the dynamic interbody device to accommodate axial rotation. The curvature of superior surface 118 and arcuate slot 120 allows the dynamic interbody device to provide coupled lateral bending and axial rotation to vertebrae adjacent to the dynamic interbody device. In some embodiments, the second member may have an arcuate slot and the first member may have a complementary protrusion.

Arcuate slot 120 and the protrusion of the second member may be dovetailed or include another type of interconnection system that inhibits non-rotational separation of first member 106 from the second member when the protrusion of the second member is engaged in the slot of the first member. End surfaces 124 of arcuate slot 120 may interact with the end surfaces of the protrusion of the second member to resist shear load applied to the dynamic interbody device when the dynamic interbody device is positioned between vertebrae. End surfaces 124 and the end surfaces of the protrusion of the second member may be guides for lateral bending axial rotation of vertebrae coupled to the dynamic interbody device.

First member 106 may include opening 122 in slot 120. A pin may be positioned in opening 122. The pin may reside in a groove in the second member to define the maximum amount of lateral bending/axial rotation allowed by the dynamic interbody device. In other embodiments, a pin positioned in an opening in the second member may reside in a groove in the first member to define the maximum amount of lateral bending/axial rotation allowed by the dynamic interbody device.

Figure 6:
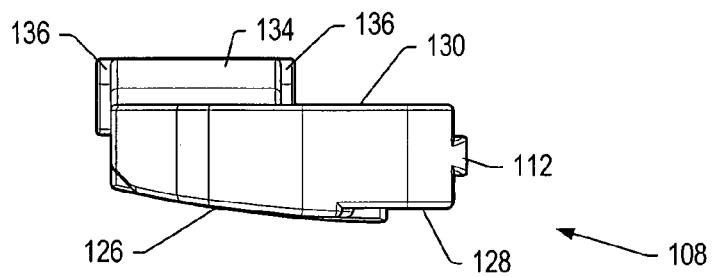
FIG. 6 depicts a front view of the second member of the dynamic interbody device embodiment.
Figure 7:
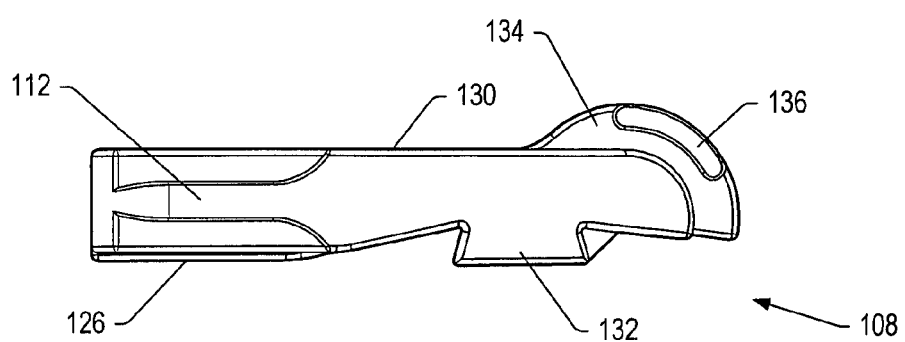
FIG. 7 depicts a side view of the second member of the dynamic interbody device embodiment.
Figure 8:
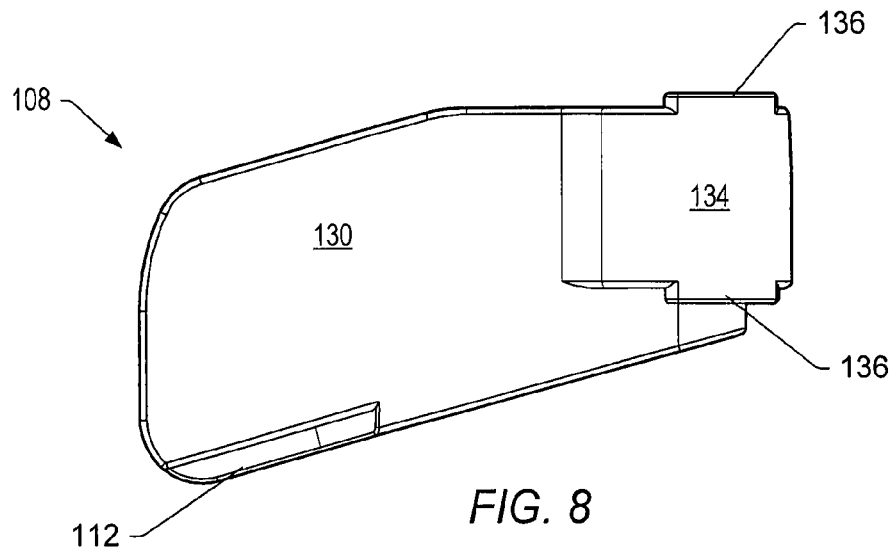
FIG. 8 depicts a top view of the second member of the dynamic interbody device embodiment.
Figure 9:
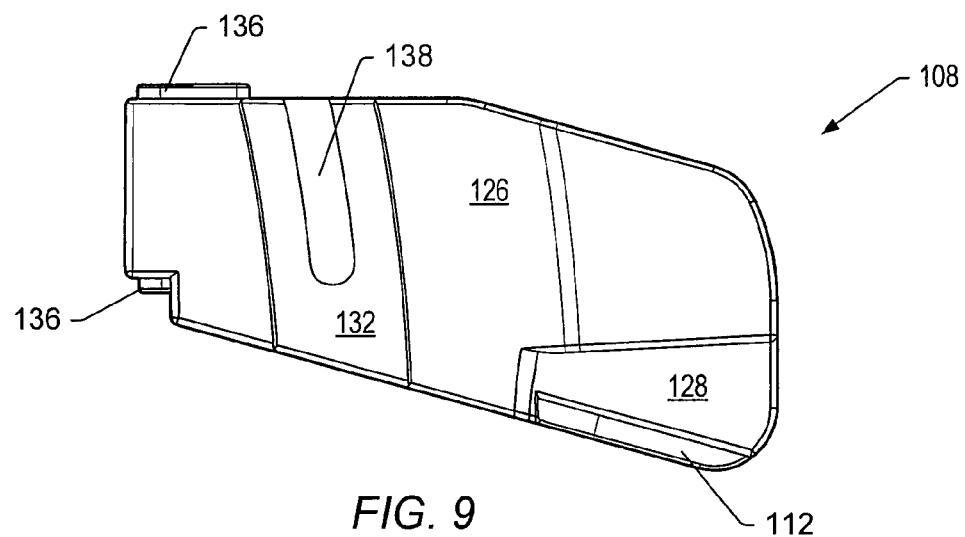
FIG. 9 depicts a bottom view of the second member of the dynamic interbody device embodiment.
Figure 10:
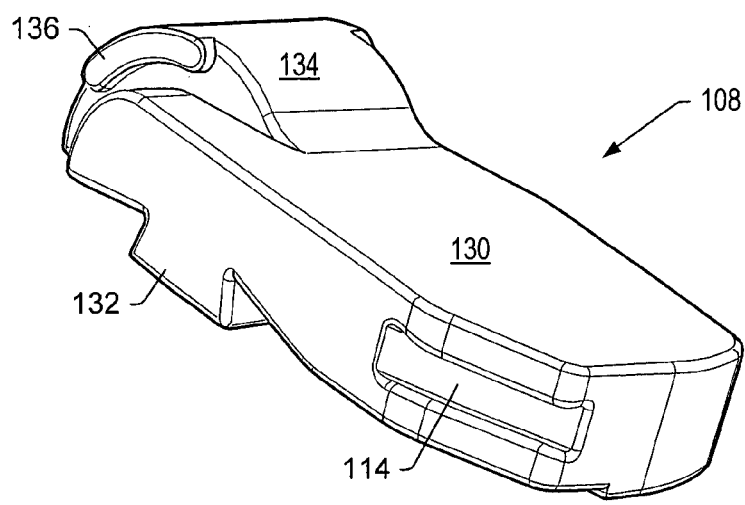
FIG. 10 depicts a perspective view of the second member of a dynamic interbody device embodiment.

FIG. 6 depicts a front view of second member 108 of dynamic interbody device 100′. FIG. 7 depicts a side view of second member 108 of dynamic interbody device 100′. FIG. 8 depicts a top view of second member 108 of dynamic interbody device 100′. FIG. 9 depicts a bottom view of second member 108 of dynamic interbody device 100′. Second member 108 may include inferior surface 126, recessed surface 128, superior surface 130, protrusion 132, bearing 134, tabs 136, groove 138, and portion 112. Some of inferior surface 126 may rest on the superior surface of the first member when protrusion 132 is placed in the arcuate slot of the first member. Inferior surface 126 may include a curvature that complements the curvature of the superior surface of the first member and protrusion 132 may complement the arcuate slot in the first member so that the dynamic interbody device is able to accommodate coupled lateral bending and axial rotation of vertebra joined to the dynamic interbody device Portion 112 of second member 108 of the dynamic interbody device (shown in FIG. 6) may engage a complementary portion of the second member of a second dynamic interbody device positioned adjacent to the dynamic interbody device when the dynamic interbody devices are positioned in a disc space between vertebrae. FIG. 10 depicts second member 108 with portion 114 that complements portion 112 of second member shown in FIG. 6. Engaging portion 112 with complementary portion 114 of the second dynamic interbody device may stabilize the dynamic interbody devices when the dynamic interbody devices are positioned between vertebrae. Coupling the dynamic interbody devices together with portions 112, 114 may assure that the second members of the dynamic interbody devices move in tandem relative to the first members of the dynamic interbody devices.

Coupling the dynamic interbody devices together with portions 112, 114 may inhibit migration of the dynamic interbody devices and/or subsidence of the vertebrae coupled to the dynamic interbody devices. Having complementary portions may require that a specific dynamic interbody device be installed prior to the other dynamic interbody device during an insertion procedure. For example, the dynamic interbody device with a female connection portion (i.e., portion 114 in FIG. 10) may need to be installed first. After insertion, migration and/or removal of the dynamic interbody devices is only possible by reversing the insertion order with the two dynamic interbody devices held in the same position as during insertion (i.e., neutral in axial rotation and lateral bending while in full flexion). Proper positioning of the two dynamic interbody devices may be determined by examining the position of the connected portions using imaging techniques before removal of the insertion instruments.

As shown in FIG. 7, second member 108 may include bearing 134. Bearing 134 may fit in a recess of the third member to allow the dynamic interbody device to accommodate flexion and extension of vertebra coupled to the dynamic interbody device. Bearing 134 may include tabs 136. Tabs 136 may fit in tracks in the third member to inhibit separation of second member 108 from the third member. To assemble the dynamic interbody device, the third member may be coupled to the second member. The second member may be coupled to the first member. The first member will inhibit separation of the third member from the second member even when the dynamic interbody device is subjected to the maximum amount of extension.

As shown in FIG. 9, groove 138 may be formed in protrusion 132 of second member 108. In some embodiments, groove 138 may be open at one side of second member 108. A pin in the first member may reside in groove 138 of the assembled dynamic interbody device.

Second member 108 may include recessed surface 128 in inferior surface 126. Recessed surface 128 may allow a portion of second member 108 to extend over a portion of the first member of the second dynamic interbody device without interference during lateral bending.

Figure 11:
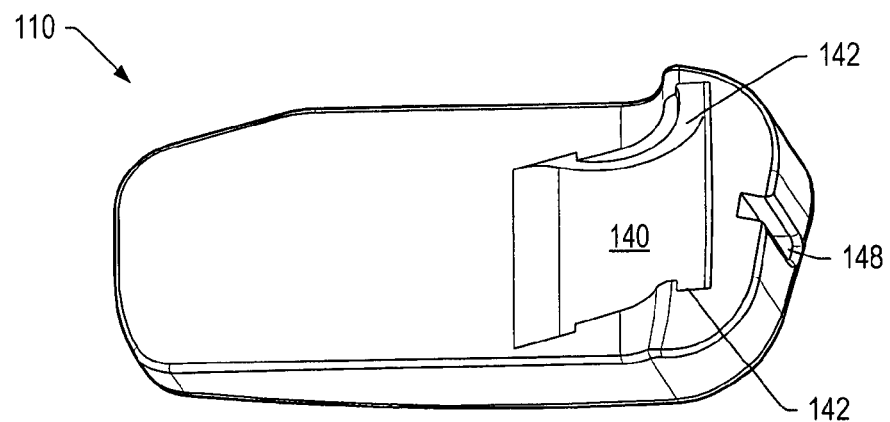
FIG. 11 depicts a perspective view of the third member of a dynamic interbody device embodiment.

FIG. 11 depicts a perspective view that emphasizes bottom surface of third member 110. Third member 110 may include recess 140 with tracks 142. Recess 140 and tracks 142 may complement the bearing and tabs of the second member.

As shown in FIG. 2, first member 106 of each dynamic interbody device 100′, 100″ may include opening 144. Opening 144 may be a threaded opening or have another type of releasable coupling mechanism. Opening 144 may be used to releasably couple the dynamic interbody device to an insertion instrument. In other embodiments, openings for the insertion instrument may be located in the second member and/or the third member.

The dynamic interbody device may include one or more features that allow the insertion instrument to hold the dynamic interbody device in a desired position. For example, first member 106 may include slot 146 and third member 110 may include slot 148. A portion of the insertion instrument may be placed in slots 146, 148. The portion of the insertion instrument that fits in slots 146, 148 may place the dynamic interbody device in a desired position for insertion between vertebrae (i.e., neutral axial rotation, neutral lateral bending, and full flexion).

Figure 12:
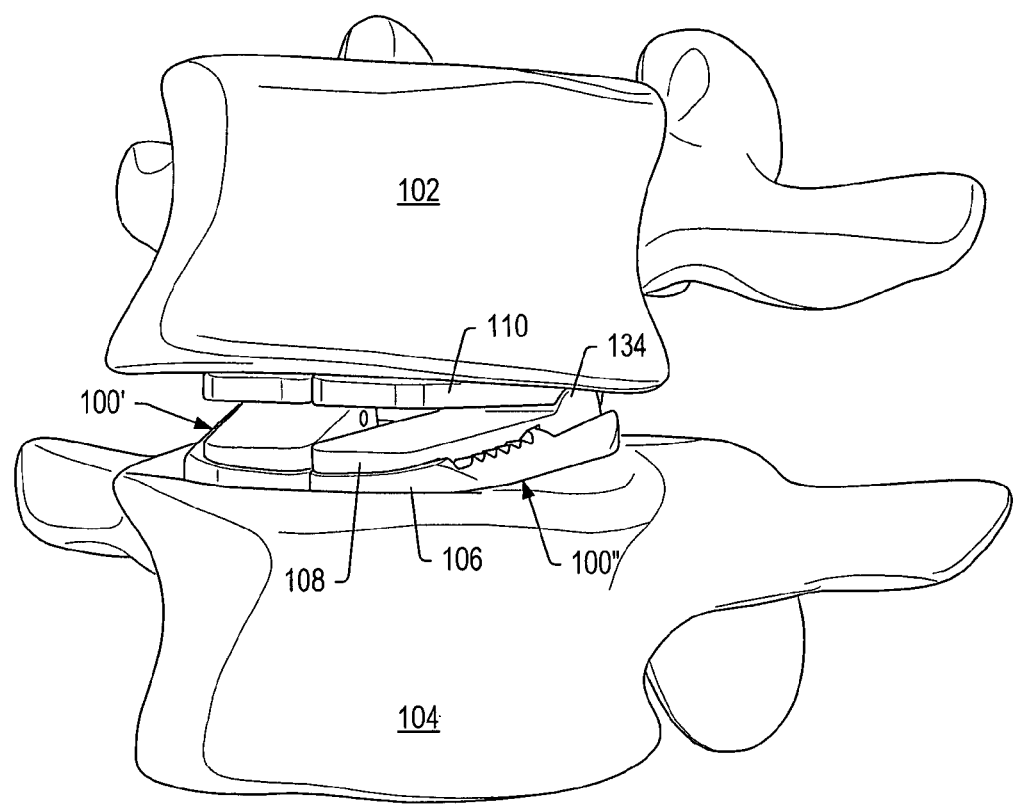
FIG. 12 depicts embodiments of dynamic interbody devices positioned between vertebrae.

FIG. 12 depicts alternate embodiments of dynamic interbody devices 100', 100" positioned between vertebra 102, 104. Each dynamic interbody device may include first member 106, second member 108 and third member 110. First member 106 and second member 108 may include complementary curved ridges that allow for coupled lateral bending and axial rotation of vertebrae 102, 104 that the dynamic interbody devices are positioned between. In some embodiments, the second member includes a guide recess. A guide pin of the first member resides in the guide recess to join the first member and the second member together and/or to limit the amount of axial rotation and lateral bending allowed by the dynamic interbody device. The first member may include undercut surfaces. The undercut surfaces of the first member may interact with undercut surfaces of the second member to inhibit separation of the first member from the second member and to take a portion of the shear load applied to the dynamic interbody device.

A tab of third member 110 may be placed in a slot of second member 108. A pin may be positioned in second member 108 through an opening in the slot to join the second member to third member 110. Second member 108 may include bearing 134. Third member 110 may include a recess with a curved surface that complements the curve of bearing 134. The coupling of the recess of third member 110 with the bearing of second member 108 may accommodate flexion and extension of vertebrae 102, 104 that dynamic interbody devices 100', 100" are positioned between.

Dynamic interbody devices 100', 100" work in conjunction to allow for coupled lateral bending and axial rotation and/or flexion/extension of vertebrae 102, 104 the dynamic interbody devices are positioned between. During an insertion procedure, careful positioning of the dynamic interbody devices 100', 100" may be needed to ensure that dynamic interbody device 100' works in conjunction with dynamic interbody device 100". In some dynamic interbody device embodiments, a separation angle of about 30° (i.e., each implant oriented at about 15° from a center line of endplate of the lower vertebra being stabilized) is desired between dynamic interbody devices 100', 100". In some dynamic interbody device embodiments, a separation angle of about 24° (i.e., each implant oriented at about 12° from a center line of endplate of the lower vertebra being stabilized) is desired between dynamic interbody devices 100', 100". Other embodiments of dynamic interbody devices may be designed to operate in conjunction with each other at other separation angles.

In some embodiments, insertion instruments may allow insertion of dynamic interbody devices 100', 100" so that ends of the dynamic interbody devices touch. Intra-operative imaging may be used to ensure the proper positioning and alignment of the dynamic interbody devices. In some embodiments, a portion of dynamic interbody device 100' may engage a portion of dynamic interbody device 100" to ensure proper positioning of the dynamic interbody devices 100', 100". For example, a dovetailed portion of dynamic interbody device 100' fits in a complementary groove of dynamic interbody device 100" when the dynamic interbody devices are properly positioned. Engaging dynamic interbody devices may inhibit migration of the dynamic interbody devices after insertion.

Figure 13:
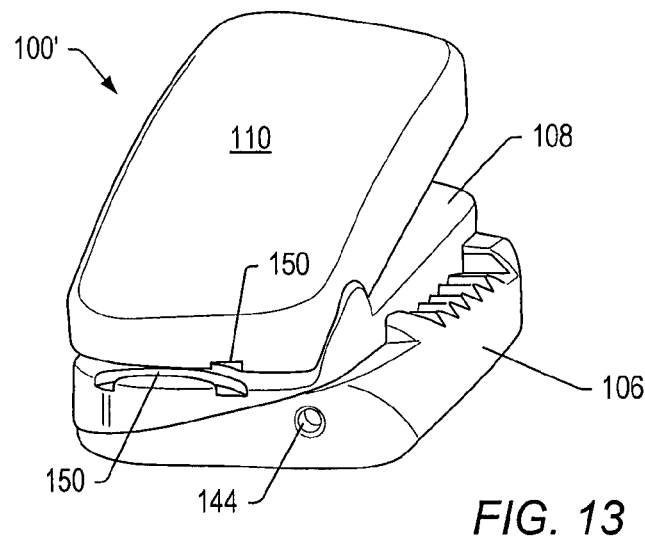
FIG. 13 depicts the posterior end of an embodiment of a dynamic interbody device.

FIG. 13 depicts the posterior end of dynamic interbody device 100' when there is no lateral bending or axial rotation of second member 108 of the dynamic interbody device relative to first member 106. In some embodiments, first member 106 may be wider than second member 108 and third member 110. First member 106 may abut the lower vertebra of the vertebrae to be stabilized. Having the first member wider than second member 108 and/or third member 110 may take advantage of the space available for insertion of the dynamic interbody devices between the vertebrae.

In many previous devices inserted using a posterior approach, the width of the portion of the device that contacted the upper vertebra was substantially the same as the width of the portion of the device that contacted the lower vertebra. The width of devices was typically the largest width that allowed insertion of the portion of the device that contacted the upper vertebra without undue retraction of neural structures exiting between the vertebrae. The space available for insertion of a device using a posterior approach is typically wider near the lower vertebra and becomes less wide nearer the upper vertebra.

In some embodiments, second member 108 and third member 110 may include curved dovetailed slots 150. Slots 150 may accept a first portion of an inserter. When the first portion of the inserter is coupled to slots 150 of second member 108 and third member 110, movement of the second member relative to the third member (e.g., flexion/extension) is inhibited. First member 106 may include inserter opening 144. Inserter opening 144 may be threaded. A second portion of the inserter may fit in inserter opening 144. When the first portion of the inserter is coupled to slots 150 and the second portion of the inserter is positioned in inserter opening 144, movement of first member 106 relative to second member 108 is inhibited.

The first member of the dynamic interbody device may be wider than the third member to take advantage of the available insertion space for the dynamic interbody devices. Having first members with large widths provides large contact area between the first members and the lower vertebra. The large contact area may inhibit subsidence of the vertebra that is more likely to subside due to the presence of the dynamic interbody devices. Even though third member may be less wide than first member, the third member provides sufficient contact against the upper vertebra to inhibit subsidence of the upper vertebra.

Pairs of dynamic interbody devices having different widths, lengths, and/or heights may be provided in the instrument kit for the spinal stabilization procedure. For example, the instrument kit may include pairs of implants having small widths, medium widths, and large widths of different heights and/or lengths.

In some embodiments, a dynamic interbody device or dynamic interbody devices may not allow coupled axial rotation and lateral bending of vertebrae adjacent to the dynamic interbody device or dynamic interbody devices. For example, in an embodiment, the curvature of ridges in the first member and second member of the dynamic interbody device only allows for axial rotation of vertebrae adjacent to the dynamic interbody device without allowing for lateral bending. The interaction of the first member with the second member allows for axial rotation and resists at least a portion of the shear load applied by the vertebrae to the dynamic interbody device. In an embodiment, the curvature of ridges in the first member and the second member allow for lateral bending of vertebrae adjacent to the dynamic interbody device without allowing for axial rotation. The interaction of the first member with the second member allows for lateral bending and resists at least a portion of the shear load applied by the vertebrae to the dynamic interbody device.

Figure 14:
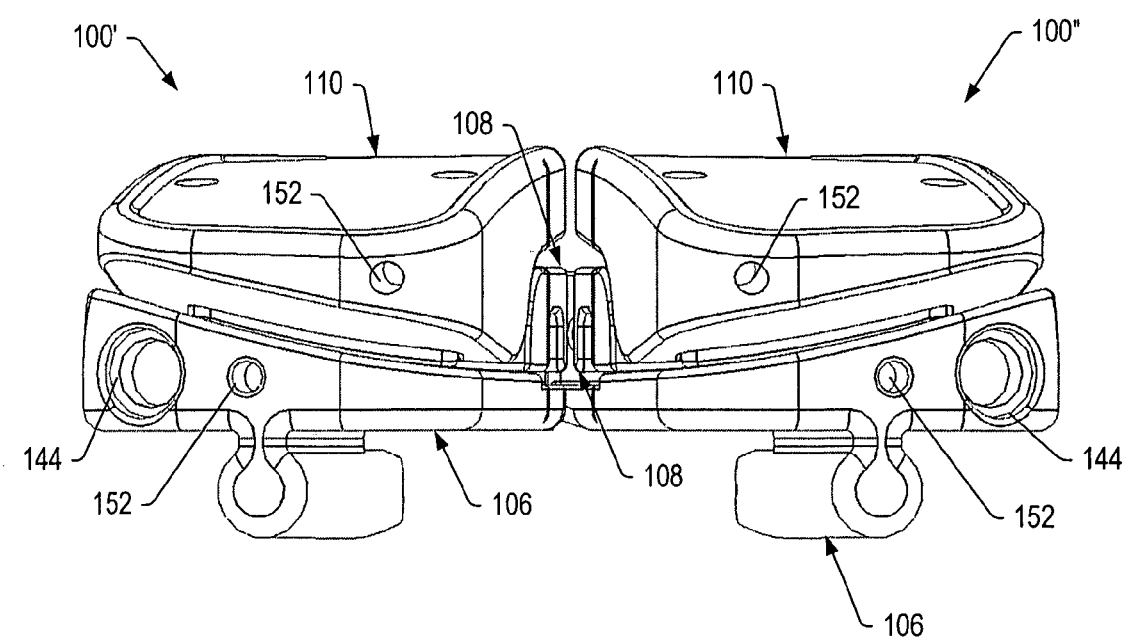
FIG. 14 depicts a rear view of an embodiment of a pair of dynamic interbody devices.

FIG. 14 depicts a perspective view of embodiments of dynamic interbody devices 100', 100". Each dynamic interbody device 100', 100" may include first member 106, second member 108 and third member 110. First member 106 may include inserter opening 144. Inserter opening 144 may be threaded. First member 106 and third member 110 may also include openings 152. Ends of an insertion instrument may be positioned in openings 152 to fix the position of first member 106 relative to third member 110 during insertion.

An instrument kit for a surgical procedure may include a number dynamic interbody devices 100', 100" having different heights. In some embodiments, the position of inserter opening 144 and/or openings 152 is different for dynamic interbody devices 100', 100" with different heights so that only the appropriate insertion instruments can be used with the dynamic interbody devices. In some embodiments, the position of inserter opening 144 and openings 152 is the same for all dynamic interbody devices so that only two insertion instruments are needed for the instrument kit (an insertion instrument for dynamic interbody device 100' and an insertion instrument for dynamic interbody device 100").

Figure 15:
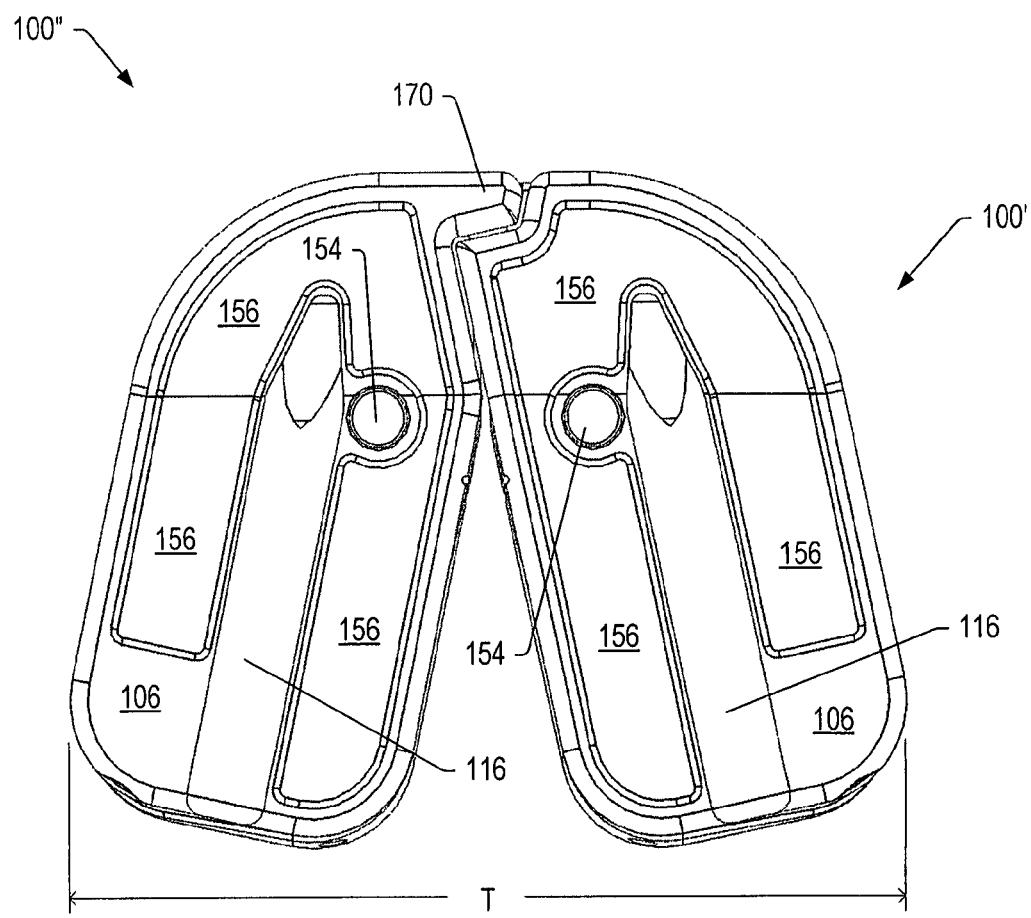
FIG. 15 depicts a bottom view of an embodiment of a pair of dynamic interbody devices.

FIG. 15 depicts a bottom view of dynamic interbody devices 100', 100". Dynamic interbody devices 100', 100" may include pins 154, keels 116, and recessed areas 156. Each pin 154 may couple first member 106 to the second member of the dynamic interbody device. Keels 116 may secure dynamic interbody devices 100', 100" to the vertebra. During the surgical procedure to install dynamic interbody devices 100', 100", a framework may be formed for positioning sizing tools and insertion instruments that allow properly sized dynamic interbody devices to be positioned at desired locations. Portions of the framework may include guides that allow a drill bit to form openings in the vertebra for keels 116.

Recessed areas 156 may have a depth of about 0.35 mm. Other depths may be used. A porous titanium coating or other material that promotes implant retention may be formed or placed in recessed area 156. Bone of the vertebra that first member 106 is placed against may bond to the porous titanium coating. Initially, the rough surface of the porous titanium coating may provide resistance to migration of the dynamic interbody device until rigid fixation is achieved when the bone bonds to the porous titanium coating.

Figure 16:
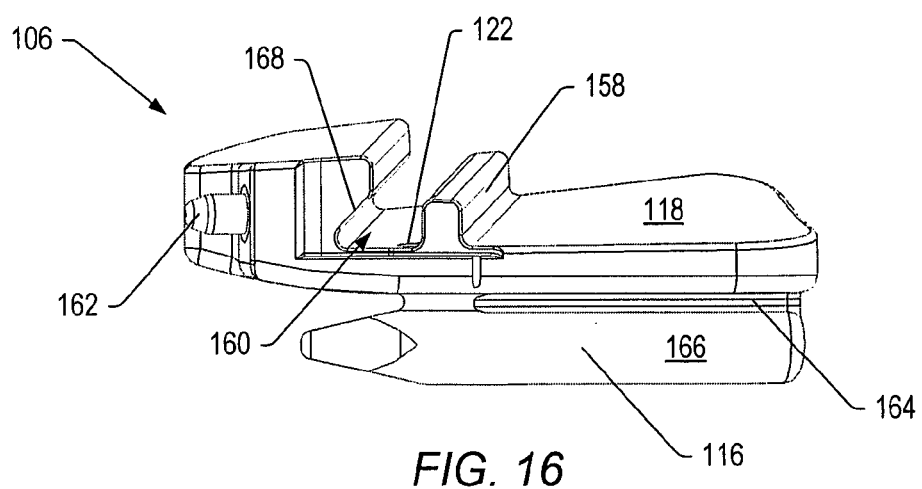
FIG. 16 depicts a side view of an embodiment of the first member of a dynamic interbody device.

FIG. 16 depicts a side view of first member 106 of dynamic interbody device 100' depicted in FIG. 14. First member 106 may include keel 116, curved ridge 158, curved groove 160, superior surface 118, and protrusion 162. Keel 116 may include neck 164 and base 166. Base 166 may be a cylinder that is wider than neck 164. The width of base 166 as compared to neck 164 inhibits keel 116 from lifting out of the vertebra. Neck 164 and base 166 may have angled portions at the anterior ends. The angled portions may facilitate insertion into the vertebra.

Curved ridge 158 may be positioned in a groove in the second member of the dynamic interbody device. An engaging portion of the second member may be placed in curved groove 160. Angled surface 168 and the corresponding angled surface of the engaging portion of the second member inhibit vertical separation of first member 106 from the second member. After the second member is coupled to first member 106, a pin may be positioned in opening 122 in groove 160 to secure the first member to the second member. The pin may provide a limit to the amount of axial rotation and/or lateral bending of vertebrae coupled to the dynamic interbody device allowed by the dynamic interbody device.

During the surgical procedure to install the dynamic interbody devices in a disc space formed between two vertebrae, protrusion 162 may be placed in an opening in an end portion of the other dynamic interbody device (end portion 170 depicted in FIG. 15). The framework formed during the insertion procedure may facilitate placement of the dynamic interbody devices so that protrusion 162 is positionable in the opening in the end portion of the other dynamic interbody device. Protrusion 162 may have a tapered bullet shape to facilitate placement of the protrusion in the opening in the end portion of the other dynamic interbody device. Images may be taken during the installation procedure to ensure that the dynamic interbody devices are properly positioned relative to each other.

Figure 17:
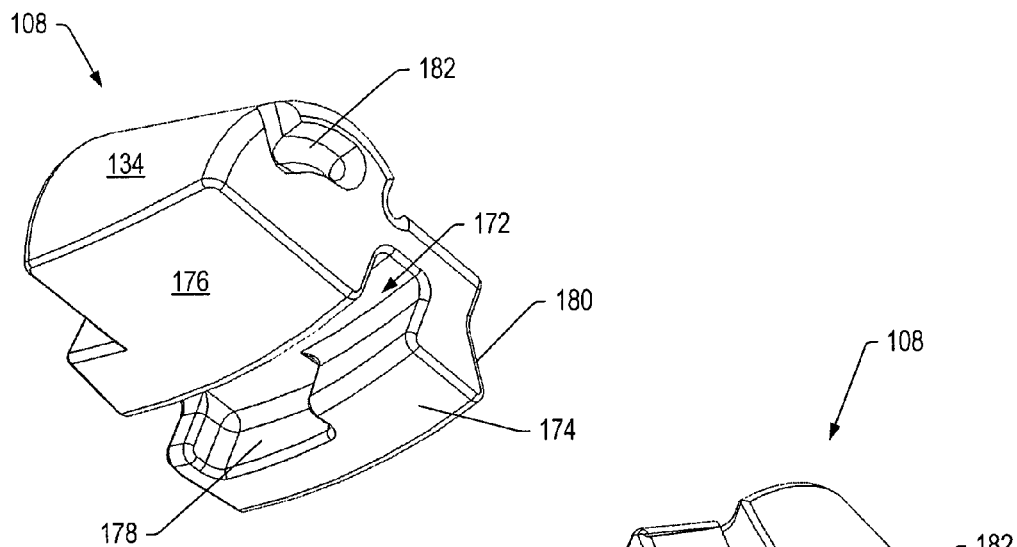
FIG. 17 depicts a perspective view of an embodiment of the second member of a dynamic interbody device that emphasizes the bottom of the second member.
Figure 18:
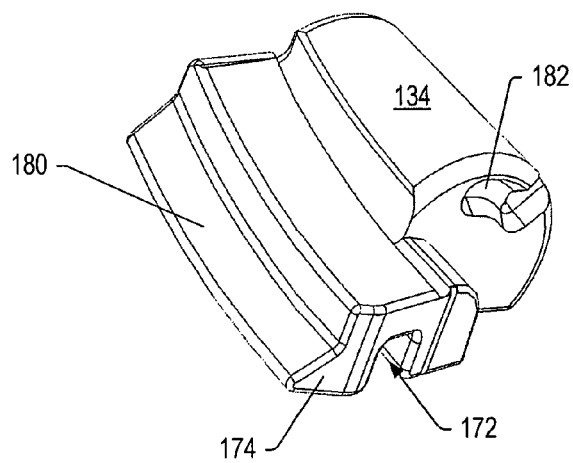
FIG. 18 depicts a perspective view of an embodiment of the second member of a dynamic interbody device that emphasizes the top of the second member.

FIG. 17 and FIG. 18 depict perspective views of second member 108 of dynamic interbody device 100" depicted in FIG. 14. Second member 108 may include angled groove 172, engaging portion 174, curved surface 176, and bearing 134. The ridge of the first member may fit in angled groove 172 of second member 108. Movement of second member 108 relative to ridge allowed by angled groove 172 may allow the dynamic interbody device to accommodate axial rotation of vertebrae coupled to the dynamic interbody device. Angled groove 172 may also include slot 178. Slot 178 may accept an end of a pin or other projection that is positioned in the first member during assembly of the dynamic interbody device. Positioning the pin in slot 178 inhibits separation of the first member from second member 108 and provides a limit to the range of motion of axial rotation and lateral bending allowed by the dynamic interbody device.

Engaging portion 174 may fit in the groove of the first member. Angled surface 180 of engaging portion may complement the angled surface of the groove in the first member. The angled surfaces may interact to inhibit vertical separation of the first member from second member 108.

Curved surface 176 of second member 108 may complement the superior surface of the first member. The complementary surfaces may allow the dynamic interbody device to accommodate lateral bending of vertebrae coupled to the dynamic interbody device.

Bearing 134 may be positioned in a recess in the third member. Bearing 134 may allow the dynamic interbody device to accommodate flexion and extension of vertebra coupled to the dynamic interbody device. Second member 108 may include channel 182 on each side of bearing 134. Channel 182 may include an entry portion and a curved portion. A ball bearing may be positioned in each channel 182 during assembly of the dynamic interbody device. The ball bearings allow the third member to move in flexion and extension relative to second member 108 and inhibit separation of the third member from the second member.

Figure 19:
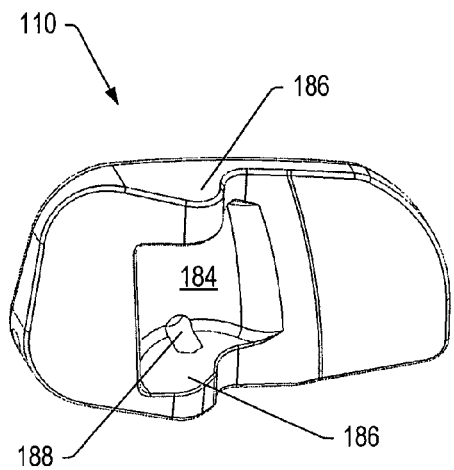
FIG. 19 depicts a perspective view of an embodiment of the third member of a dynamic interbody device that emphasizes the bottom of the third member.

FIG. 19 depicts a perspective view of third member 110 that emphasizes the bottom surface of the third member. Third member 110 may include recess 184 defined by arms 186. Recess 184 may complement the bearing of the second member. Opening 188 may be formed in each arm 186. A ball bearing may be positioned in each opening 188 during assembly of the dynamic interbody device.

Figure 20:
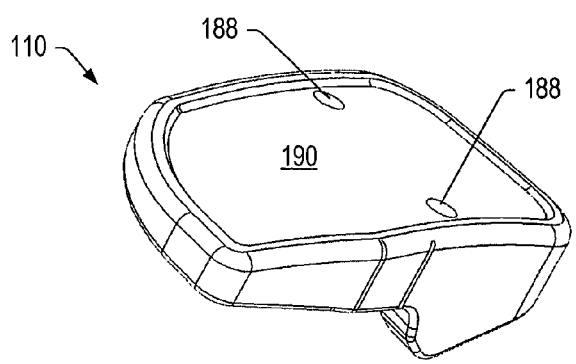
FIG. 20 depicts a perspective view of an embodiment of the third member of a dynamic interbody device that emphasizes the top of the third member.

FIG. 20 depicts a perspective view of third member 110 that emphasizes the top surface of the third member. Openings 188 extend from the top surface to the recess on the bottom side of third member 110. Third member 110 may include recessed area 190. Recessed areas 190 may have a depth of about 0.35 mm. Other depths may be used. A porous titanium coating or other material that promotes implant retention may be formed or placed in recessed area 190. Bone of the vertebra that third member 110 is placed against may bond to the porous titanium coating. Initially, the rough surface of the porous titanium coating may provide resistance to migration of the dynamic interbody device until rigid fixation is achieved when the bone bonds to the porous titanium coating.

During assembly of the dynamic interbody device, the bearing of the second member may be placed in the recess of the third member. The third member may be tilted relative to the second member so that the openings in the arms of the third member align with the entry portions of the channels in the bearings in the second members. A ball bearing may be placed in each opening. The ball bearings may fall adjacent to the beginning of the arced portions of the channels in the second member. The third member may be tilted downwards towards the engaging portion of the second member so that the entry portions of the groove are not aligned with the openings in the third member to trap the ball bearings in the arced portions of the channels.

The engaging portion of the second member may be positioned at the groove in the first member. The second member/third member combination may be pushed into the first member so that the curved ridge of the first member is positioned in the groove of the second member and the engaging portion of the second member is positioned in the curved groove of the first member. A pin may be press fit into the opening in the first member so that the end of the pin resides in the slot in the second member. When the third member is rotated, the bottom posterior surface of the third member contacts the upper posterior surface of the first member before the opening in the third member aligns with the upper portion of the channel in the second member, thus preventing the possibility of removal of the ball bearings from the dynamic interbody device.

In some embodiments, the third members of the dynamic interbody devices are domed. For example, the upper surfaces of the third members have a dome approximately 1 mm in height to better conform to the concave surface of the upper vertebra. The domed surface may provide immediate and long-term retention of the dynamic interbody devices in the disc space.

For some dynamic interbody devices, the vertebra contact surface of the first member is larger than the vertebral contact surface of the third member. The larger vertebral contact surface of the first member mimics the anatomy of the surgical canal. Table 1 gives values for four dynamic interbody device sizes. The AP Length is the anterior-posterior length. The Lower Width is the width across the lower surface of the first member. The T Width is the transverse width of a pair of assembled dynamic interbody device measured from the lower surface of the first member of each dynamic interbody device (i.e., width T depicted in FIG. 15). Upper Area is the footprint area of the contact surface of the third member. Lower Area is the footprint area of the contact surface of the first member, not excluding the keel.

TABLE 1

| Size | AP Length (mm) | Lower Width (mm) | T Width (mm) | Upper Area (mm$^2$) | Lower Area (mm$^2$) |
|---|---|---|---|---|---|
| 1 | 24 | 13 | 31.3 | 557 | 557 |
| 2 | 26.7 | 13.7 | 33.9 | 633 | 679 |
| 3 | 29.3 | 14.5 | 36.5 | 706 | 797 |
| 4 | 32 | 15 | 38.6 | 777 | 906 |

The above noted sizes were chosen based on a statistical sizing analysis of percentile groupings of male and female vertebral body endplates. For L4-L5 and L5-S1 male and female vertebral bodies, the estimated vertebral body endplate coverage of ideally sized and placed dynamic interbody devices ranged from 38% (95$^{th}$ percentile L4-L5 upper endplate for males) to 63% (5$^{th}$ percentile L5-S1 lower endplate for females) with an overall average endplate coverage of 53%. A 30% to 40% coverage may be sufficient to prevent subsidence into cancellous bone under physiologic axial loads. Portions of the dynamic interbody devices are positioned on the endplates of the vertebral bodies near the pedicles. These regions are high strength regions of the vertebral bodies that provide extra subsidence residence as compared to interbody devices that are designed to be centrally positioned on the endplates.

Figure 21:
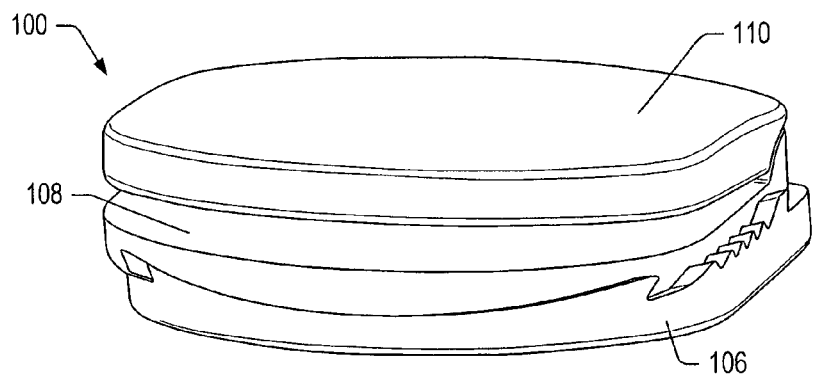
FIG. 21 depicts a perspective view of an embodiment of a dynamic interbody device.

In some embodiments, a single dynamic interbody device may be used. FIG. 21 depicts a perspective view of dynamic interbody device 100 emphasizing the anterior side and the superior surface. Dynamic interbody device 100 is shown with some axial rotation and lateral bending from a neutral position. Dynamic interbody device 100 may be placed in a disc space between two vertebrae using an anterior approach. The width of the dynamic interbody device may be greater that one half the width of the vertebrae the dynamic interbody device is to be positioned between. The width of the dynamic interbody device may be substantially the same as the width of the vertebrae the dynamic interbody device is to be positioned between. Dynamic interbody device 100 may include first member 106, second member 108, and third member 110. Dynamic interbody device 100 may be a bilateral device with coupled axial rotation and lateral bending. First member 106 may be coupled to second member 108 so that dynamic interbody device 100 accommodates lateral bending and axial rotation of vertebrae coupled to dynamic interbody device 100. As with a natural functional spinal unit, dynamic interbody device 100 couples lateral bending and axial motion together so that lateral bending motion causes axial rotation, and axial rotation causes lateral bending. Third member 110 may be coupled to second member 108 so that dynamic interbody device 100 accommodates flexion and extension of vertebrae coupled to the dynamic interbody device.

The superior surface may be coupled to an upper vertebra of the vertebrae to be stabilized. An inferior surface of the dynamic interbody device may be coupled to the lower vertebra of the vertebrae to be stabilized. At least a portion the superior surface may be positioned near the edge of the endplate of the upper vertebra so that the dynamic interbody device abuts strong, supportive bone of the upper vertebra. At least a portion of the inferior surface may be positioned near the edge of the endplate of the lower vertebra so that the dynamic interbody device abuts strong, supportive bone of the lower vertebra.

Figure 22:
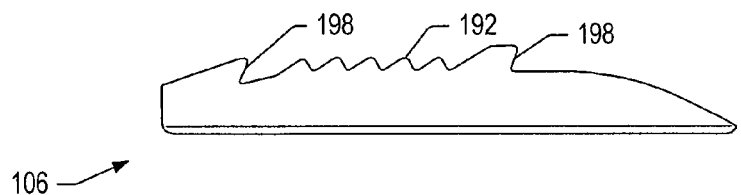
FIG. 22 depicts a side view of a first member of the dynamic interbody device depicted in FIG. 21.
Figure 23:
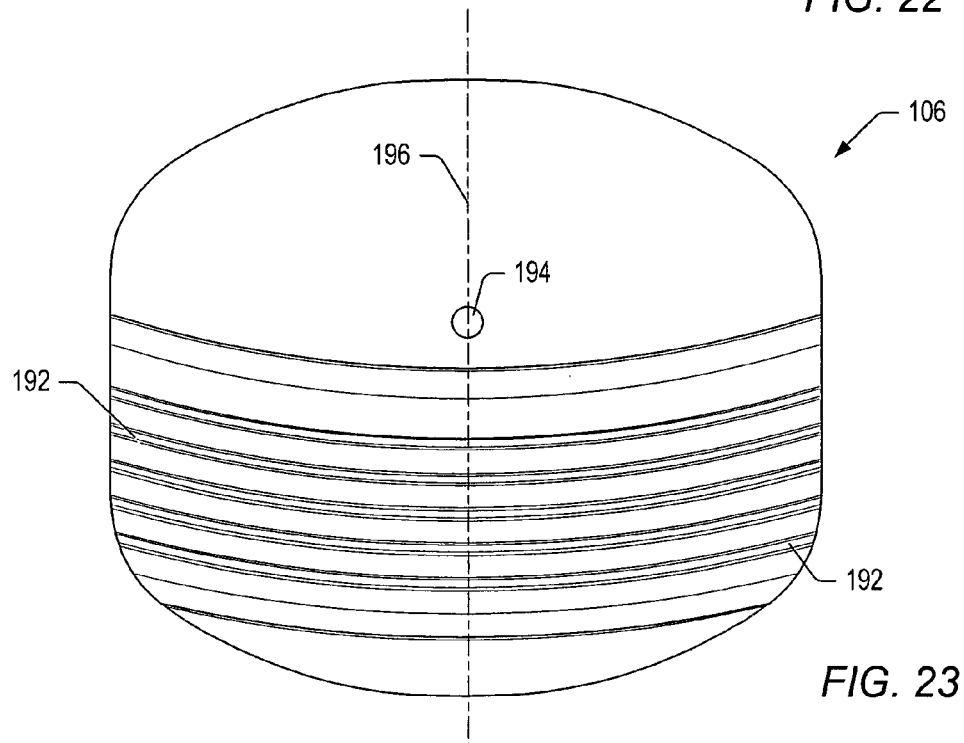
FIG. 23 depicts a top view of the first member of the dynamic interbody device depicted in FIG. 21.

FIG. 22 depicts a side view of first member 106 and FIG. 23 depicts a top view of the first member. First member 106 may include ridges 192 and pin opening 194. Ridges 192 and the grooves between the ridges may mate with corresponding grooves and ridges of the second member so that the dynamic interbody device accommodates coupled lateral bending and axial rotation. As depicted in FIG. 23, ridges 192 may be curved. The curvature allows the dynamic interbody device to accommodate axial rotation. Ridges 192 may be symmetrical about center line 196 of first member 106 so that the dynamic interbody device accommodates the same amount of clockwise axial rotation as counterclockwise axial rotation. In some embodiments, the ridges and grooves may not be symmetrical about the centerline so that the dynamic interbody device allows no or limited axial rotation in a particular direction to accommodate the needs of a patient.

A guide pin may be press fit or otherwise secured in pin opening 194 after the second member is coupled to first member 106. The guide pin may fit in a guide recess in the second member. The guide pin may limit the amount of lateral bending and axial rotation allowed by the dynamic interbody device and/or inhibit separation of first member 106 from the second member. In some embodiments, the first member may have a guide recess and a guide pin may positioned in the second member may reside in the guide recess.

As seen in FIG. 22, first member 106 may include one or more undercut surfaces 198. Undercut surfaces 198 may inhibit separation of the second member from first member 106 when the second member is coupled to the first member. Undercut surfaces 198 may share a portion of the load applied to the dynamic interbody device.

Figure 24:
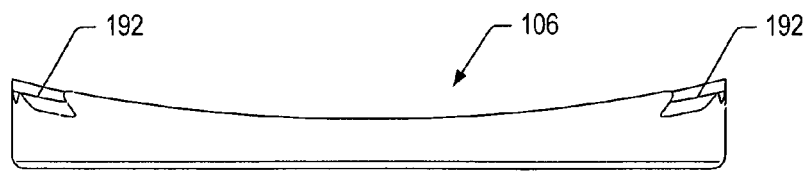
FIG. 24 depicts a front view of the first member of the dynamic interbody device depicted in FIG. 21.

FIG. 24 depicts a front view of first member 106. First member 106 may decrease in height from a position at or near the right side of the first member to the center of the first member. The first member 106 may increase in height from the center to a position near or at the left side of the first member. At least a portion of first member 106 has a concave shape. The concave shape of at least a portion of first member 106 may allow the dynamic interbody device to accommodate lateral bending of vertebrae coupled to the dynamic interbody device.

Figure 25:
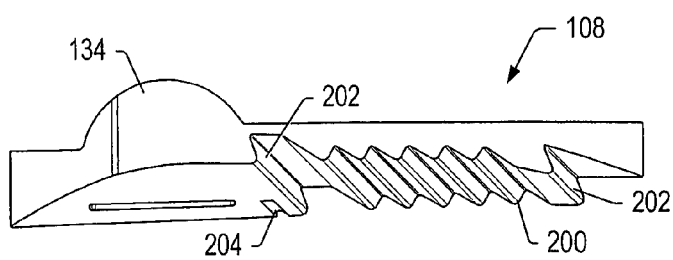
FIG. 25 depicts a side view of the second member of the dynamic interbody device depicted in FIG. 21.

FIG. 25 depicts a side view of second member 108. The bottom of second member 108 may include ridges 200, one or more undercut surfaces 202, and guide recess 204. Ridges 200 may be curved and the bottom of second member 108 may have a convex shape so that the ridges of the second member mate with the grooves between the ridges of the first member, and the ridges of the first member mate with the grooves between the ridges of the second member. Undercut surfaces 202 may interact with the undercut surfaces of the first member to inhibit separation of second member 108 from the first member when the dynamic interbody device is assembled. An end of the guide pin placed in the pin opening of the first member may reside in guide recess 204 of second member. The guide pin may limit the range of motion for axial rotation and lateral bending of the assembled dynamic interbody device and inhibit separation of the first member from second member 108.

Second member 108 may include bearing 134. Bearing 134 may fit in a recess in the third member so that the assembled dynamic interbody device is able to accommodate flexion and/or extension of vertebrae coupled to the dynamic interbody device. Other connection systems between the second member and the third member that accommodate flexion/extension of vertebrae coupled to the dynamic interbody device may also be used.

In some embodiments, the second member includes a bearing recess and the third member includes a bearing that fits in the recess. Bearing 134 may be located towards a posterior end of the dynamic interbody device. Locating bearing 134 near the posterior end of the dynamic interbody device locates the axis of rotation for flexion/extension close to the natural axis of rotation for flexion/extension of the vertebrae. The curvature of bearing 134 may be relative small to limit translational movement of the third member relative to second member during flexion/extension.

Figure 26:
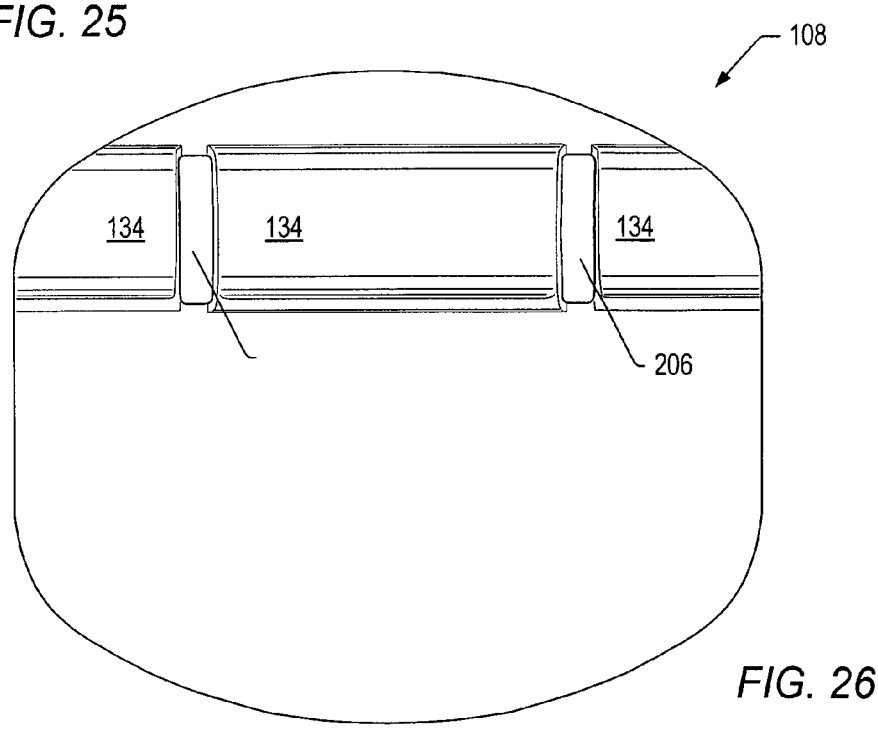
FIG. 26 depicts a top view of the second member of the dynamic interbody device depicted in FIG. 21.

FIG. 26 depicts a top surface of second member 108. Second member 108 may include slots 206. Tabs of the third member may be positioned in slots 206. One or more pins positioned in bearing 134 of second member 108 and through the tabs of the third member may couple the second member to the third member. When the dynamic interbody device is positioned between vertebrae, fluid may enter the slots and keep the dynamic interbody device lubricated.

In some embodiments, the second member of the dynamic interbody device may have a protrusion and the first member may have a complementary slot instead of a plurality of complementary ridges and grooves. In some embodiments, the second member of the dynamic interbody device may have a slot and the first member may have a complementary protrusion instead of a plurality of complementary ridges and grooves in the second member and the first member.

Figure 27:
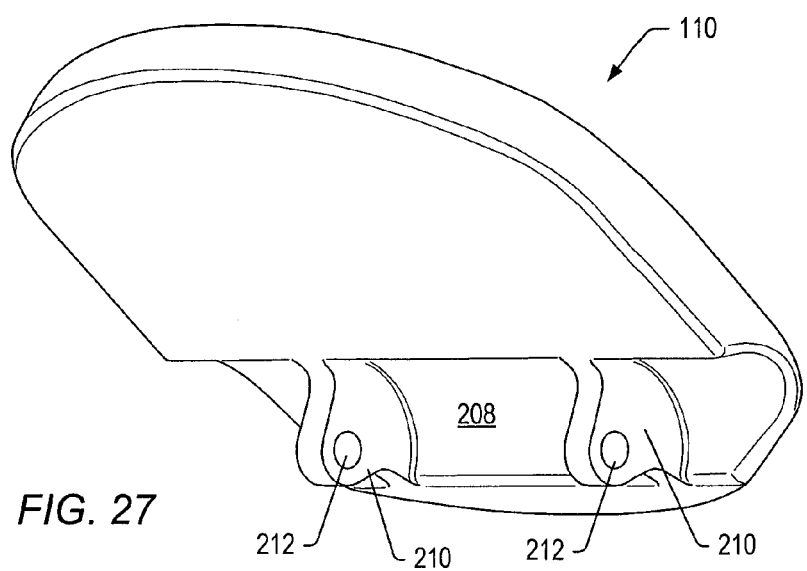
FIG. 27 depicts a perspective view of the third member of the dynamic interbody device depicted in FIG. 21.

FIG. 27 depicts a perspective view of third member 110 that emphasizes a bottom surface of the third member. Third member 110 may include recess 208 and tabs 210. Recess 208 may be complementary to the bearing of the second member so that the assembled dynamic interbody device allows for flexion/extension of vertebrae coupled to the dynamic interbody device. Tabs 210 may be positioned in the slots of the second member. A pin or pins positioned through openings 212 in tabs 210 may couple third member 110 to the second member.

In some embodiments, the front faces of the first member, second member and/or third member may include indentions, openings, or other surface features for connecting the dynamic interbody device to an inserter. The connection between the dynamic interbody device and the inserter allows force to be applied substantially evenly to the dynamic interbody device to facilitate insertion of the dynamic interbody device into the disc space. The inserter may maintain the position of the first member relative to the second member and the third member during insertion.

The ridges of the first member are complementary to the ridges of the second member. When the dynamic interbody device is positioned between vertebrae, the vertebrae exert compressive and/or shear forces on the dynamic interbody device. Having a number of ridges increases the surface area for dissipating force applied to the dynamic interbody device. Increasing the surface area for dissipating force applied to the dynamic interbody device may reduce pressure and decrease wear of the dynamic interbody device.

A front part of the third member may rotate towards the second member to accommodate flexion. The front part of the third member may rotate away from the second member to accommodate extension.

Figure 28:
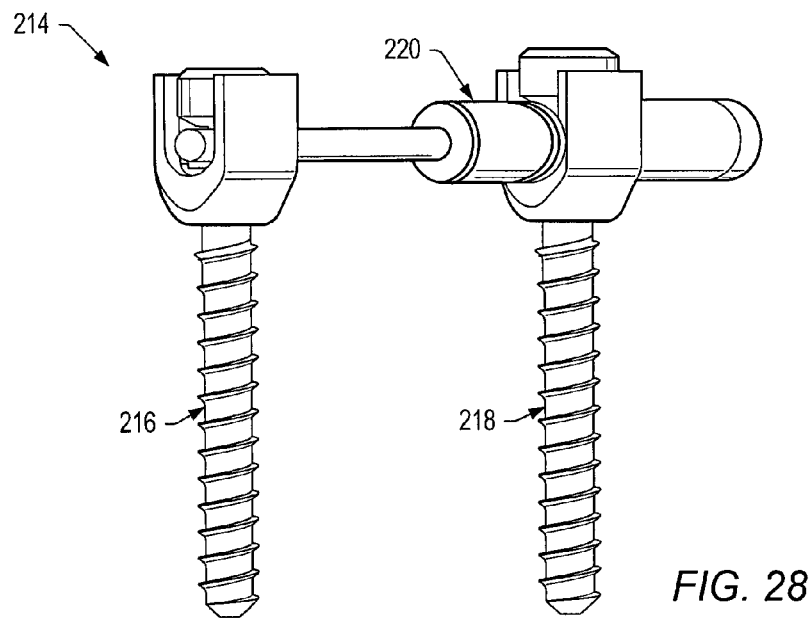
FIG. 28 depicts a perspective view of an embodiment of a posterior stabilization system.

Dynamic posterior stabilization systems may be used to support vertebrae and/or to provide resistance to motion of a first vertebra relative to a second vertebra. FIG. 28 depicts an embodiment of in-line dynamic posterior stabilization system 214. Dynamic posterior stabilization system 214 may include first bone fastener 216, second bone fastener 218, and dampener system 220. An instrument kit supplied for a spinal stabilization procedure may include a number of bone fasteners and dampener systems that allow for the formation of dynamic posterior stabilization systems.

An elongated member of dampener system 220 is positioned directly between collars of first bone fastener 216 and second bone fastener 218 in an in-line system. In some embodiments, the dampener system may be offset from both of the bone fasteners to accommodate space restrictions in the patient. In some embodiments, the dynamic posterior stabilization system includes an offset member that couples to the second bone fastener to allow the dampener system to be positioned to one side of the second bone fastener. The offset member may allow the dampener system to be positioned towards the spine (medially) or away from the spine (laterally). Positioning the dampener system to one side of the second bone fastener allows a second dampener system of a multi-level construct to be attached to the collar of the second bone fastener. In dynamic posterior stabilization systems where the dampener system is offset from one of the bone fasteners, a transverse connector to a dynamic posterior stabilization system on an opposite side of the spine may be needed to counteract moments generated when force is applied to the dynamic posterior stabilization system due to the offset position of the bone fastener relative to the dampener system.

The bone fasteners of dynamic posterior stabilization system 214 may be pedicle screws, clamps, hooks, barbs, or other fasteners that secure to vertebrae. In some embodiments, the bone fasteners are pedicle screws. The pedicle screws may include self-tapping thread. In some embodiments, the pedicle screws are polyaxial pedicle screws. In some embodiments, the bone fasteners are non-polyaxial pedicle screws.

Figures 29, 30:
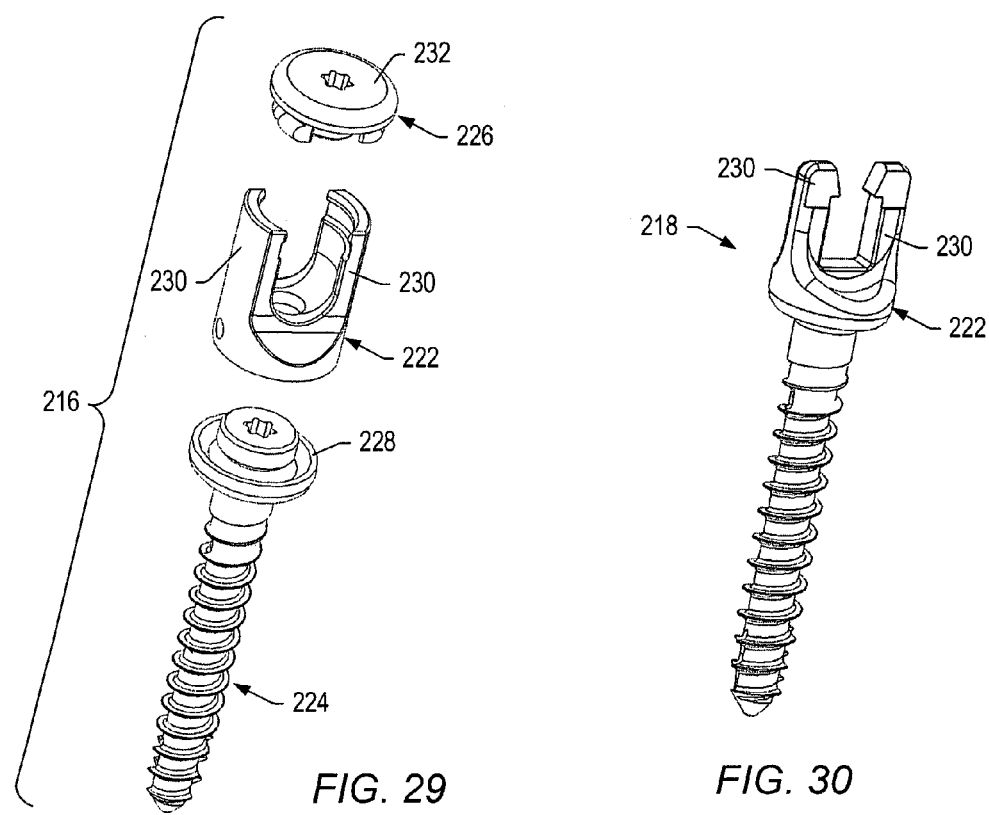
FIG. 29 depicts an exploded perspective view of an embodiment of a bone fastener.
FIG. 30 depicts a perspective view of an embodiment of a bone fastener.

FIG. 29 depicts an exploded view of an embodiment of first bone fastener 216 that includes collar 222, threaded shaft 224 and closure member 226. Collar 222 may be press fit or otherwise secured to threaded shaft 224. An opening through a bottom portion of collar 222 allows an end of a driver to couple to a tool opening in threaded shaft 224 so that the threaded shaft may be driven into a vertebra.

In some embodiments, a portion of threaded shaft 224 near collar 222 has a porous titanium coating. The porous titanium coating may enhance fixation of the bone fastener to bone. Only having a portion of the threaded shaft with the porous titanium coating may allow for removal of the bone fastener during a revision surgery. In some embodiments, the entire length of the threaded shaft may have a porous titanium coating.

Closure member 226 may be attached to collar 222 to secure a portion of the dampener system to the bone fastener. In some embodiments, closure member 226 includes threading that engages threading in collar 222. In some embodiments, the closure member may snap onto the collar. In some embodiments, a bottom portion of closure member 226 includes one or more ridges or projections that engage the portion of the dampener system positioned in the collar to securely hold the dampener system in the collar. The ridges or projections may bite into or deform against the portion of the dampener system positioned in the collar.

In some embodiments, an offset member of a dampener system may slide over collar 222. The offset member allows the dampener system to be positioned medial or lateral to the bone fastener. The bottom of the offset member may be positioned against base 228 of threaded shaft 224. When the bottom of the offset member is positioned against base 228 of threaded shaft 224, the top of the offset member may be substantially even with the top of arms 230 of collar 222. Top portion 232 of closure member 226 may extend past arms 230 of collar 222 to inhibit removal of the offset member when the closure member is coupled to the collar.

In some embodiments, the first bone fastener is identical to the second bone fastener. In some embodiments, the first bone fastener may by a different type of fastener, and/or have a different collar, size, and/or length than the second bone fastener. For example, FIG. 30 depicts an embodiment of second bone fastener 218 that is different than first bone fastener 216 depicted in FIG. 29. Arms 230 of second bone fastener 218 depicted in FIG. 30 may snap onto a sleeve positioned in collar 222 of the second bone fastener to secure the sleeve to the second bone fastener. The use of snap-on arms may eliminate the need for a closure member for the bone fastener.

Figure 31:
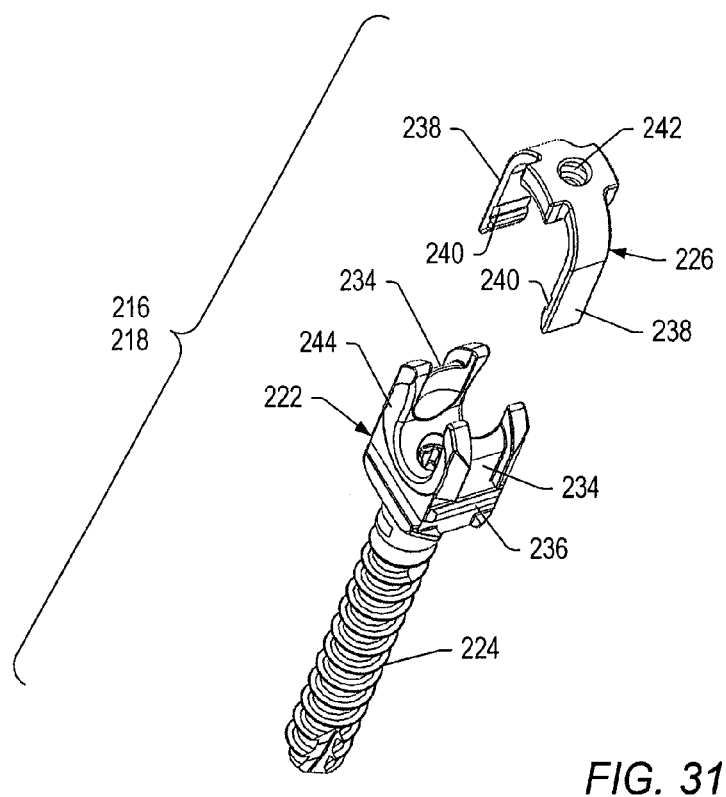
FIG. 31 depicts a perspective view of an embodiment of a bone fastener.

In some embodiments, the first bone fastener is identical to the second bone fastener. FIG. 31 depicts an embodiment of a bone fastener for an in-line dynamic posterior stabilization system that may be used as first bone fastener 216 or second bone fastener 218. The bone fastener may include collar 222, threaded shaft 224 and closure member 226. In some embodiments, collar 222 is about 15 mm high, about 11.6 mm wide, about 8 mm thick. Collar 222 may have other dimensions.

Collar 222 may include slots 234 and ledges 236 on each side of the collar. Arms 238 of closure member 226 may fit in slots 234. Grooves 240 in arms 238 may snap over ledges 236 of collar 222 to secure closure member 226 to the collar. Closure member 226 may include threaded opening 242. An insertion tool may be attached to threaded opening 242 to facilitate attachment of closure member 226 to collar 222. The insertion tool may also be used to remove closure member 226 from collar 222. A threaded end of the insertion tool may be attached to threaded opening 242. The insertion tool may be rotated to contact the end of the insertion tool against an object positioned in collar (e.g., a ball or elongated member of a dampener system). Continued rotation of the insertion tool will apply upward force to closure member 226 that pulls grooves 240 past ledges 236 and allows closure member 226 to be removed from collar 222.

The inside surface of collar 222 may be a smooth spherical surface. A ball of a dampener system may be positioned in collar 222. The ball of the dampener system may articulate in collar 222. The articulation may be unlimited in axial rotation. The articulation may have about ±13° range of motion in the medial-lateral direction and ±24° in the anterior-posterior direction. The limits of motion may occur when a portion of the dampener system (e.g., the elongated member) contacts the inside edges of collar 222.

Collar 222 may include concave recesses 244 on each side of the collar. Convex portions of washers of the dampener system may be positioned in concave recesses 244. Concave recesses 244 may interact with the convex portions of the washers to center the dampener system in collar 222. The dampener system may articulate within collar 222. The range of motion of the dampener system relative to the collar may be about ±10° in the medial-lateral direction, about ±23° in the anterior-posterior direction, and about ±35° in axial rotation.

Dampener systems may be preassembled as single units. The dampener systems may be included in an instrument kit for the spinal stabilization procedure. The instrument kit supplied for a surgical procedure may include a number of different bone fasteners. Bone fasteners may be provided in a variety of lengths and thread diameters. In some embodiments, the instrument kit includes bone fasteners with lengths ranging from about 30 to about 55 mm in 5 mm increments. Bone fasteners of a specific length may have the same color and/or include indicia indicating the length. In some embodiments, the instrument kit includes two sets of bone fasteners, each set having a different thread diameter. For example, the first bone fastener set may have a thread diameter of about 6.0 mm and the second set may have a thread diameter of 7.0 mm. The 6.0 mm thread diameter bone fasteners may be the standard bone fasteners used in most procedures. The 7.0 mm thread diameter bone fasteners may be used in the event of a revision surgery after removal of the smaller bone fastener. The bone fasteners may be color coded and/or include indicia that indicates the thread diameter of the bone fasteners.

The instrument kit may include dampener systems having various lengths. Lengths of dampener systems refer to the interpedicular distance measured between centers of collars of the bone fasteners. For a single level spinal stabilization procedure for two adjacent vertebrae, the instrument kit may include dampener systems ranging in length from about 25 mm to about 35 mm in 5 mm increments. Other lengths and/or size increments may be provided. Also, the length of the dampener systems may be adjustable by +2.5 mm by rotating a portion (e.g., a ball) of the dampener system. The dampener systems may be color coded and/or include indicia that indicate the lengths of the dampener sets.

In some embodiments, the dampener systems are isolated dual dampener systems. One dampener set provides resistance to flexion and another dampener set provides resistance to extension in dual dampener systems. In some embodiments, the dampener systems are partially shared dual dampener systems. One dampener set provides resistance to extension and both dampener sets provide resistance to flexion in shared dual dampener systems. In some embodiments, the dampener systems are single dampener systems. One dampener set provides resistance to both flexion and extension in single dampener systems.

A dampener set may be a single dampener or a plurality of dampeners. The dampeners may be elastic washers, elastic tubes, springs, or other systems that provide resistance to compression. The dampener sets may have non-linear compression characteristics such that the dampener sets are initially easier to compress and then become stiffer. The use of dampener sets with non-linear compression characteristics may allow for a large neutral zone (10-50% of the total range of motion) where the stiffness in the neutral zone is about 10-30% of the stiffness outside of the neutral zone.

Dampener sets may be made of biocompatible material. The dampener set material may be able to undergo large deformations for millions of cycles. The dampener set material may be fatigue and wear resistant under large deformations (e.g., ~50% or more). In some embodiments, the dampener sets may be made of materials having non-linear compression behavior that approximates or matches the behavior of the normal spine in flexion/extension, and/or lateral bending. In some embodiments, the dampener sets may be made of material or materials having linear compression behavior. The material shape and/or the configuration of linear materials may allow for non-linear compression behavior that approximates or matches the behavior of the normal spine in flexion-extension and/or lateral bending.

Figure 32:
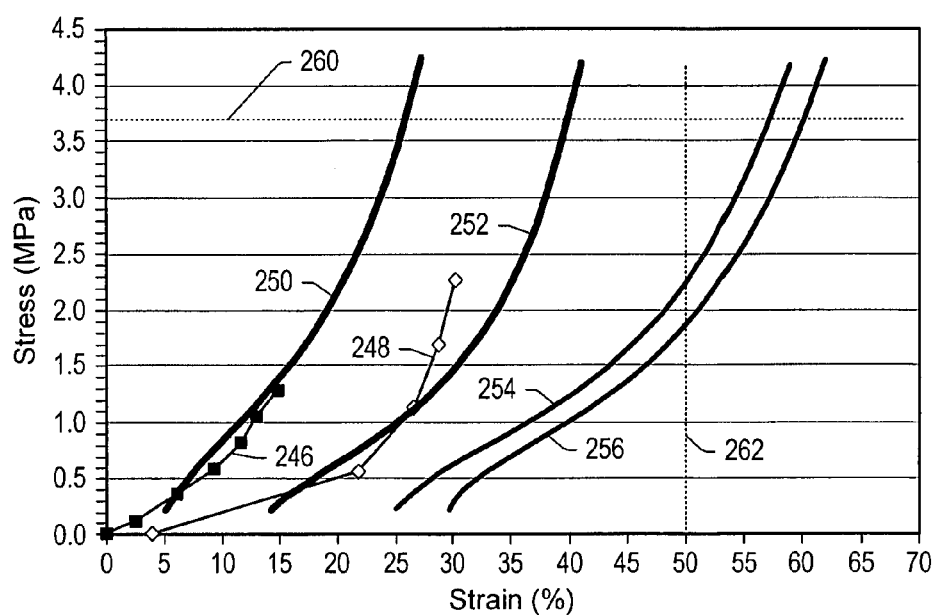
FIG. 32 depicts a plot of stress versus strain for the compression of silicone dampeners together with estimated stress-strain behavior required by the dampeners to allow for normal physiological motion of a reconstructed functional spinal unit.

The material used to form dampener sets may be elastic foam. Materials that may be used to form the dampener sets are silicone elastomers. Silicone elastomers may be available from NuSil Silicone Technology, LLC. (Carpinteria, Calif.). Other types of elastomers may also be used. FIG. 32 depicts stress-strain behavior required by dampener sets to allow for normal physiological motion of a reconstructed function spinal unit plotted along with measured compressive stress-strain curves for four silicone elastomers. Data for curve 246 is based on in vitro testing data from isolated lumbar functional spinal units. Data for curve 248 is based on in vitro testing data from whole lumbar spines. The remaining curves depict stress strain behavior of silicone elastomers available from NuSil Technology, LLC. Curve 250 depicts stress-strain for 80 durometer, unrestricted LSR (liquid silicone rubber) elastomer (MED-4880). Curves 252, 254, 256 depict curves for unrestricted high-consistency elastomers. Curve 252 corresponds to 70 durometer MED-4770, curve 254 corresponds 55 durometer MED-4755, and curve 256 corresponds to 50 durometer MED 4719. Line 260 depicts an approximation of the maximum in vivo stress on a dampener set. Line 262 depicts an approximation of the maximum in vivo strain on a dampener set. The non-linearity of the elastomers match well with the estimated requirements for the dampener sets.

Figure 33:
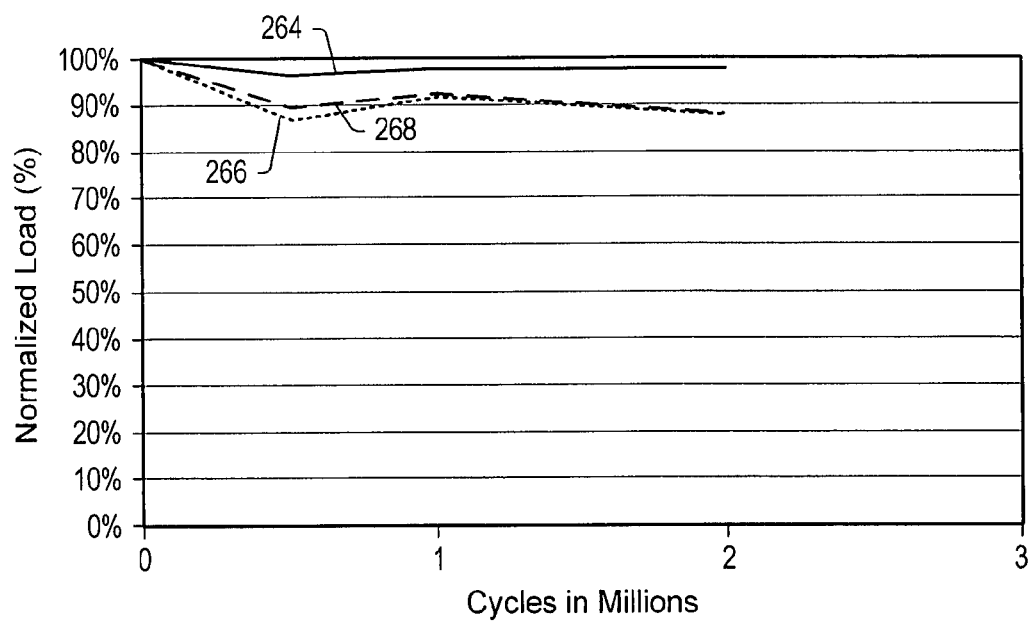
FIG. 33 depicts a plot of normalized load versus number of compression cycles for 70 durometer silicone elastomer at 20% or 40% strain.

FIG. 33 depicts dampener set load when compressed after 0.5 million, 1 million and 2 million compression cycles to 20% or 40% strain for 70 durometer silicone elastomers. Curve 264 is for 20% fatigue strain for a gamma sterilized material. Curve 266 is for 40% fatigue strain for a gamma sterilized material. Curve 268 is for 40% fatigue strain for an unsterilized material. The load decreased slightly (up to approximately 15%) following the first 0.5 million cycles and then remained essentially constant for up to 2 million cycles. Gamma sterilization resulted in a slight load loss for the material.

Figure 34:
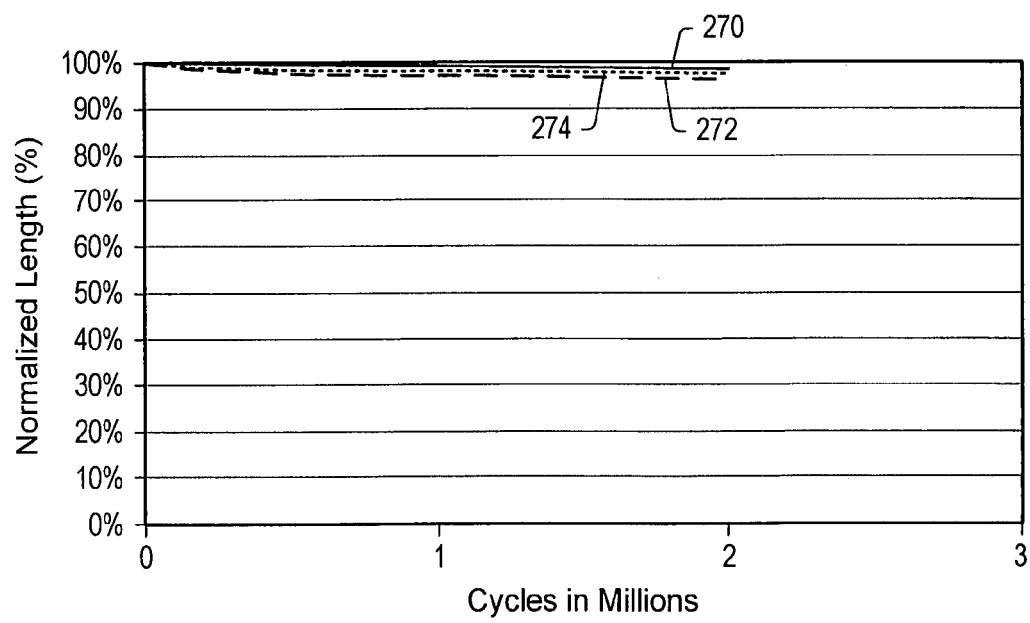
FIG. 34 depicts a plot of plot of normalized length versus number of compression cycles for 70 durometer silicone elastomer at 20% or 40% strain.

FIG. 34 depicts dampener set resting length after 0.5 million, 1 million and 2 million compression cycles to 20% or 40% strain for 70 durometer silicone elastomers. Curve 270 is for 20% fatigue strain for a gamma sterilized material. Curve 272 is for 40% fatigue strain for a gamma sterilized material. Curve 274 is for 40% fatigue strain for an unsterilized material. The resting length of the dampener sets did not appreciably decrease after 2 million compression cycles. The amount of permanent length reduction was less than about 5% following repetitive cycling loading with strain below 50% of the initial dampener length.

A dampener set may be pre-compressed during assembly of the dampener system. For example, a length of a dampener set before assembly into a dampener system may be about 15% longer than the length of the dampener set after assembly into the dampener system. Pre-compressing the dampener set may accommodate any permanent deformation of the dampener set due to repetitive loading. Pre-compressing the dampener set may also inhibit formation of a gap between the dampener set and other portions of the dampener system when the dampener system is in a neutral position.

Figure 35:
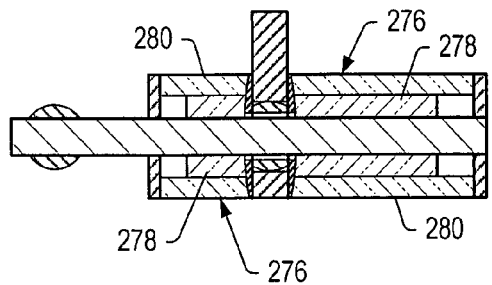
FIG. 35 depicts a cross-sectional representation of a portion of an embodiment of a dynamic posterior stabilization system.

In some embodiments, non-linear dampener set behavior may be obtained using materials that do not have inherent non-linear properties. Non-linear dampener behavior may be obtained by altering the dampener set design from a simple cylinder design. For example, a first elastomer with a first length may be positioned concentrically inside or outside of a second elastomer with a length that is different from the first length. FIG. 35 depicts a cross-sectional representation of a portion of a dampener system with dampener sets 276 of concentrically positioned elastomers. Inner dampener 278 may be made of a material having a first modulus of elasticity. Outer dampener 280 may be made of a material having a lower modulus of elasticity. In some embodiments, the material used to form the outer dampener is the same material as the material used to form the inner dampener. In some embodiments, the material used to form the inner dampener and/or the outer dampener has substantially linear compression behavior. In some embodiments, the material used to form the inner dampener and/or the outer dampener has non-linear compression behavior.

Figure 36A:
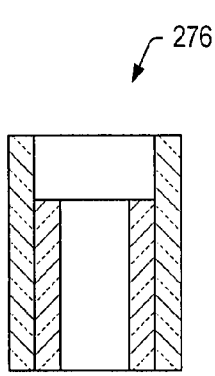
FIG. 36A depicts a cross section of a dampener set embodiment formed of a two concentric cylinders.
Figure 36B:
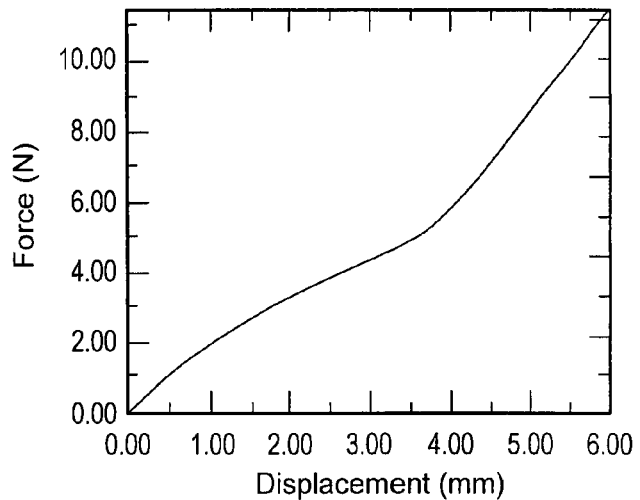
FIG. 36B depicts a plot of force versus displacement for simulated compression of the dampener set depicted in FIG. 36A.
Figure 37A:
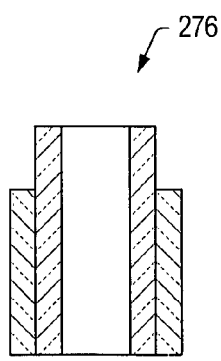
FIG. 37A depicts a cross section of a dampener set embodiment formed of a two concentric cylinders.
Figure 37B:
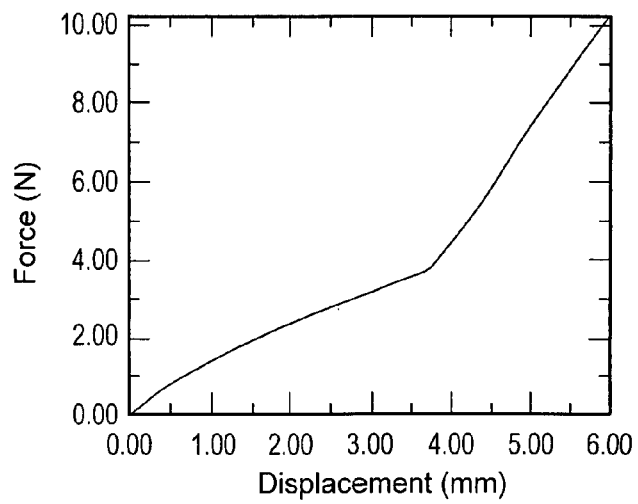
FIG. 37B depicts a plot of force versus displacement for simulated compression of the dampener set depicted in FIG. 37A.

Computer simulations may be used to model compression behavior of materials. FIG. 36B depicts a plot of force versus displacement for simulated compression of concentric dampener set 276 depicted in cross section in FIG. 36A. FIG. 37B depicts a plot of force versus displacement for simulated compression of concentric dampener set 276 depicted in cross section in FIG. 37A.

Figure 38:
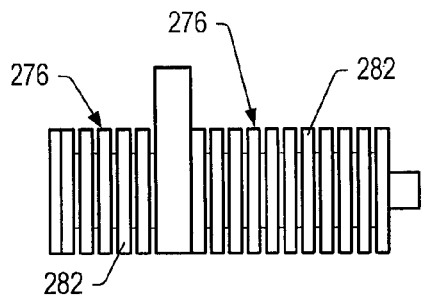
FIG. 38 depicts a side view representation of a portion of an embodiment of a dynamic posterior stabilization system.
Figure 39:
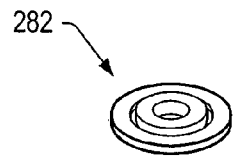
FIG. 39 depicts a perspective view of an embodiment of a single small dampener used to form dampener sets depicted in FIG. 38.

In some embodiments, non-linear dampener set behavior may be obtained by changing the shape of the dampener set. FIG. 38 depicts a side view representation of dampener set 276 that is formed of a stack of small dampeners 282. FIG. 39 depicts a perspective view of one dampener 282. Dampener 282 may be shaped so that the initial area of contact between two dampeners is relatively small. When dampeners 282 are compressed, additional contact area between two dampeners develops.

In some embodiments, a modified single piece dampener set may be used instead of a stack of small dampeners. FIG.

Figure 40A:
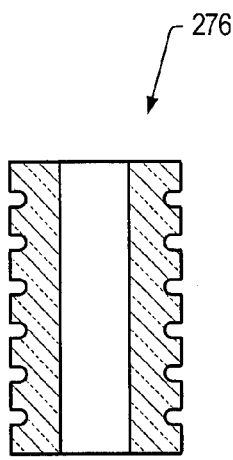
FIG. 40A depicts a cross section of a dampener set embodiment formed of large and small diameter sections.
Figure 40B:
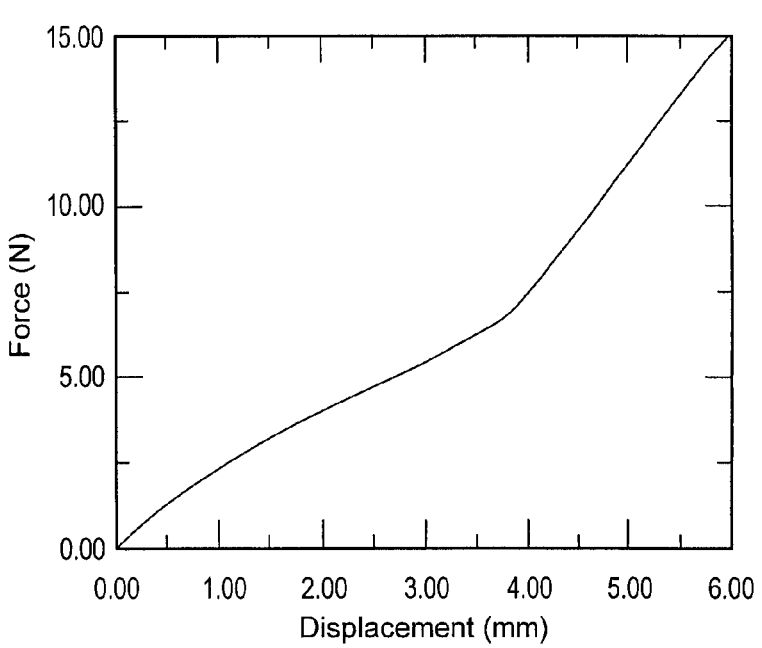
FIG. 40B depicts a plot of force versus displacement for simulated compression of the dampener set depicted in FIG. 40A.

40A depicts a cross section of an embodiment of dampener set 276 with alternating segments of large and small diameter. Dampener set 276 may be molded as a single piece. FIG. 40B depicts a plot of force versus displacement for the simulated compression of the dampener set depicted in FIG. 40A.

Figure 41:
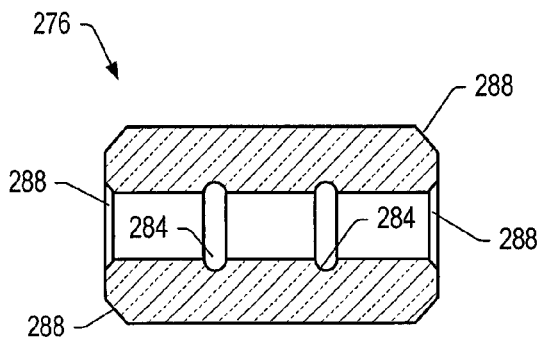
FIG. 41 depicts a cross-sectional representation of a dampener set embodiment with fillets and chamfered ends.
Figure 42:
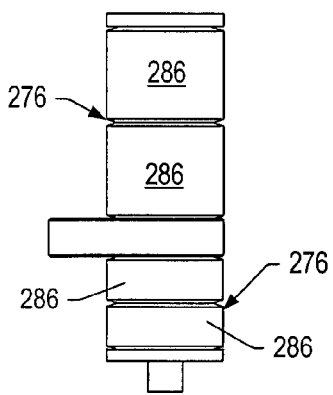
FIG. 42 depicts a side view representation of a portion of an embodiment of a dynamic posterior stabilization system where the dampener sets are formed of a number of segments.

Dampener sets may be subjected to significant fatigue and wear requirements. Dampener set geometry and/or arrangement may be altered to increase the operating life of the dampener set. A common location for cracks to form is the center of the inside diameter of the dampener set. As shown in FIG. 41, fillets 284 may be formed at other locations in dampener set 276 to relieve the stress applied at the center of the inside diameter of dampener set 276. In other embodiments, the dampener set may be formed of two or more segments so that the maximum stress is located at two or more locations in the dampener set. FIG. 42 depicts dampener set 276 formed of a number of segments 286.

Figure 43:
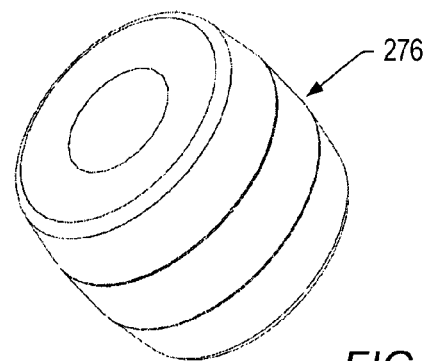
FIG. 43 depicts a perspective view of an embodiment of a barrel shaped dampener set.

In some embodiments, dampener set may have a barrel shape. FIG. 43 depicts dampener set 276 with a barrel shape. A barrel shaped dampener set may delay the onset of buckling and inhibit fatigue damage to the dampener set.

Wear of the dampener sets may occur at the upper and lower outer edges and/or at the upper and lower inner edges of the dampener sets. In some embodiments, the outer edges of the dampener sets may be rounded or chamfered to inhibit wear of the dampener sets. In some embodiments, the inner edges of the dampeners may be rounded or chamfered to inhibit wear of the dampeners. FIG. 41 depicts a cross-sectional embodiment of dampener set 276 with chamfered ends 288.

Figure 44:
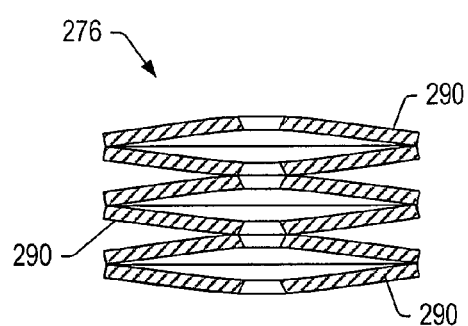
FIG. 44 depicts a cross-sectional representation of a plurality of stacked conical washers that may be used as a dampener set of a dynamic posterior stabilization system.

In some embodiments, a conical washer design may be used to form the dampener set. Using conical washers may allow for large deformations while limiting the strain on the dampener material. FIG. 44 depicts a cross-sectional representation of stacked conical washers 290 that may be used to form dampener set 276.

FIG. 28 depicts an embodiment of dynamic posterior stabilization system 214. Dampener system 220 is an isolated dual dampener system. In an isolated dual dampener system, a first dampener set positioned between the bone fasteners is compressed during extension, and little or no force is applied to a second dampener set. The second dampener set is compressed during flexion, and little or no force is applied to the first dampener set during flexion. The second dampener set may be longer than the first dampener set if the allowable amount of flexion is greater than the allowable amount of extension.

Dynamic posterior stabilization system may be coupled to a pair of vertebra on a first side of the spine. When the patient laterally bends towards the side on which dynamic posterior stabilization system is coupled, the first dampener set is compressed. When the patient laterally bends away from the side on which dynamic posterior stabilization system is coupled, the second dampener set is compressed.

When the dampener system is secured to the first bone fastener, a shaft of the dampener system is fixed relative to the first bone fastener to inhibit rotational movement of the shaft. In some embodiments, the shaft is able to rotate relative to the second bone fastener to accommodate axial rotation of vertebrae coupled to the dynamic posterior stabilization system. In some embodiments, the vertical position of the shaft relative to the collar of the second bone fastener is variable so that the dynamic posterior stabilization system is able to accommodate axial rotation of vertebrae coupled to the dynamic posterior stabilization system.

Figure 45:
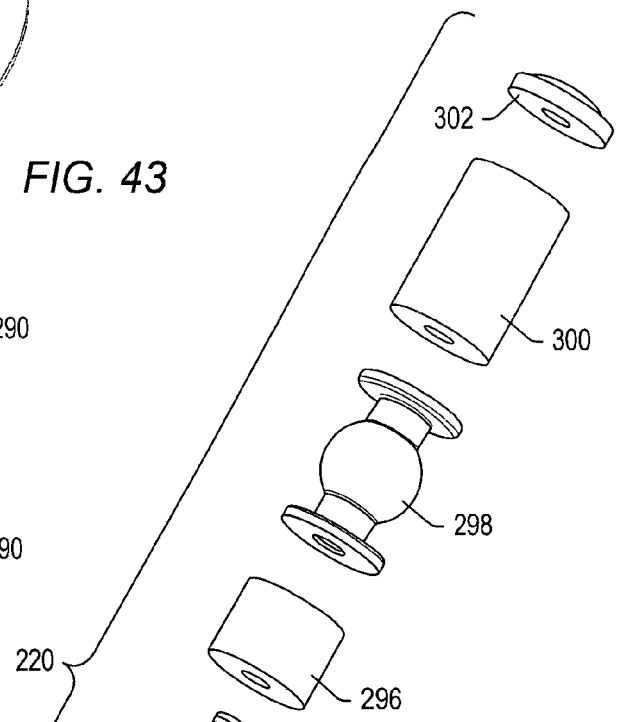
FIG. 45 depicts an exploded view of an embodiment of an in-line, isolated dual dampener system.
Figure 45:
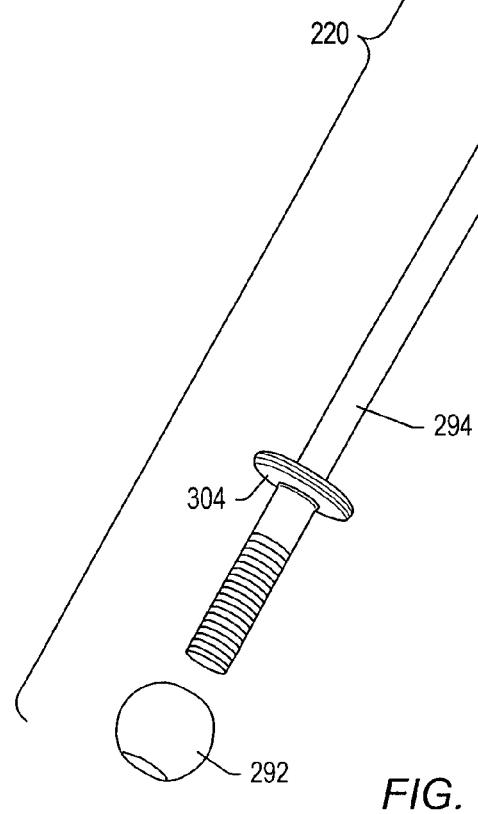

FIG. 45 depicts an exploded view of an embodiment of dampener system 220 that is an isolated dual dampener system. Dampener system 220 is an in-line system. Dampener system 220 may include ball 292, elongated member 294, first dampener set 296, sleeve 298, second dampener set 300, and stop 302. Ball 292 may be positioned on a first threaded portion of elongated member 294. In some embodiments, the threaded portion of elongated member 294 may be less than 15 mm, less than 10 mm, less than 7.5 mm or less than 5 mm in length.

Elongated member 294 may include stop 304. First dampener set 296 may be positioned on elongated member 294 against stop 304. Sleeve 298 may be placed on elongated member 294 against first dampener set 296. Elongated member 294 may be able to rotate relative to sleeve 298. Elongated member 294 may also be able to move axially relative to sleeve 298 to compress first dampener set 296 or second dampener set 300 and allow for flexion/extension and/or lateral bending. Second dampener set 300 may be positioned on elongated member 294 against sleeve 298. In some embodiments, the portions of dampener system 220 that contact dampener sets 296, 300 have spherical contours. Stop 302 may be secured to elongated member 294 against second dampener set 300. Stop 302 may include threading that couples to a second threaded portion of elongated member 294. In some embodiments, stop 302 is permanently fixed to elongated member 294 by staking the threading.

When the assembled dampener system is attached to the bone fasteners of the dynamic posterior stabilization system, the patient may be positioned in a neutral position with substantially no flexion, extension, or lateral bending. The position of ball 292 on the first threaded portion of elongated member 294 may be adjusted by rotating the ball so that sleeve 298 fits in the collar of the second bone fastener and the ball fits in the collar of the first bone fastener with little no compression of first dampener set 296 or second dampener set 300. When the position of ball 292 is at the desired position, excess length of the shaft beyond the ball may be cut off and/or the further rotation of the ball on the shaft may be inhibited. The dampener system may be coupled to the bone fasteners (e.g., by closure members).

When elongated member 294 is coupled to the first bone fastener, translational and rotational movement of the elongated member relative to the first bone fastener may be inhibited. When elongated member 294 is coupled to the second bone fastener, translational and/or rotational movement of the elongated member relative to the second bone fastener may be possible. The ability to have translational movement of elongated member 294 relative to the second bone fastener may allow isolated dual dampener system 220 to accommodate flexion, extension and lateral bending of a first vertebra coupled to the dynamic posterior stabilization system relative to a second vertebra coupled to the dynamic posterior stabilization system. The ability to have rotational movement of elongated member 294 relative to the second bone fastener may allow isolated dual dampener system 220 to accommodate axial rotation of vertebrae coupled to the dynamic posterior stabilization system.

Elongated member 294 may be a rod, bar, plate, combination thereof, or other type of member coupled to the first bone fastener and the second bone fastener. In some embodiments where the isolated dual dampener system is to be used with a dynamic interbody device, elongated member 294 may be bent so that the elongated member has a curvature that facilitates the use of the isolated dual dampener system in conjunction with the dynamic interbody device. Elongated members with appropriate curvature may be included in the instrument kit for the spinal stabilization procedure. In some embodiments, elongated members may be bent in the operating room. The instrument kit for the surgical procedure may include a bender.

Figure 46:
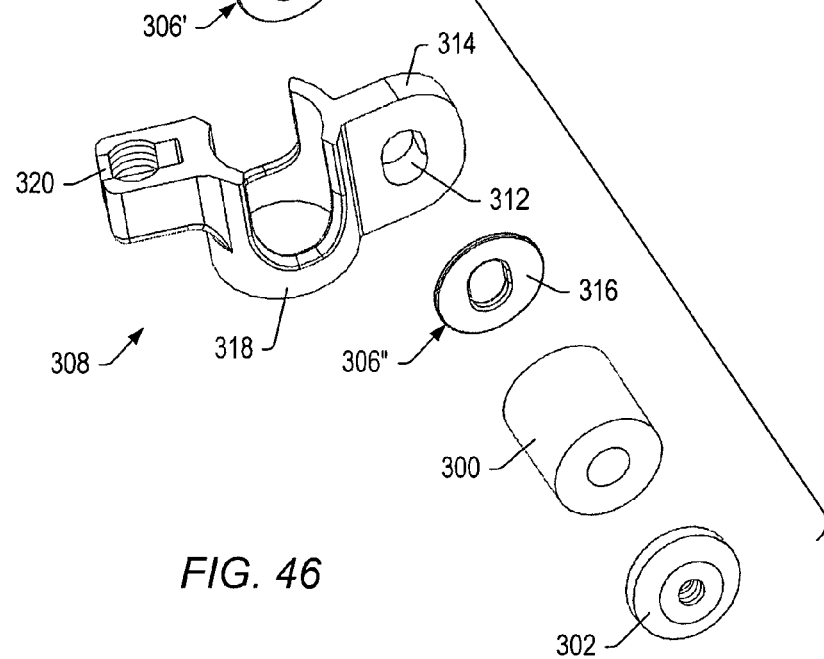
FIG. 46 depicts an exploded view of an embodiment of a lateral offset, isolated dual dampener system.

FIG. 46 depicts an exploded view of an embodiment of dampener system 220. Dampener system 220 is an isolated dual dampener system that may be offset laterally from the second bone fastener. Dampener system 220 may include ball 292, elongated member 294, first dampener set 296, washers 306, offset member 308, second dampener set 300, and stop 302. Ball 292 may be positioned on a first threaded portion of elongated member 294.

Elongated member 294 may include one or more flats 310. Flats 310 may interact with the walls that define elongated opening 312 in offset member arm 314 to inhibit rotation of elongated member 294 relative to offset member 308. Elongated opening 312 may allow elongated member 294 to move up or down when the elongated member is positioned through arm 314 so that the dampener system is able to accommodate axial rotation of vertebrae coupled to the dynamic posterior stabilization system. In some embodiments, a dampener may be positioned in the elongated member to provide resistance to axial rotation.

Elongated member 294 may include stop 304. First dampener set 296 may be positioned on elongated member 294 against stop 304. First washer 306' may be positioned against first dampener set 296. Offset member 308 may be positioned against first washer 306' and second washer 306" may be positioned against the offset member. Second dampener set 300 may be positioned against second washer 306" and stop 302 may be threaded on a second threaded portion of elongated member 294 against the second dampener set.

Surfaces 316 of washers 306', 306" that contact dampeners may be spherically contoured. Surfaces 316 may provide a large contact area between dampener sets 296, 300 and the washers. Other portions of dampener systems that contact the dampeners may also have spherically contoured surfaces. The large contact area provided by the spherical surfaces may smooth out the contact stresses and reduce irregular compression of the dampener sets. Washers 306 may inhibit extrusion of dampener sets 296, 300 into opening 312 of offset member 308 when the dampener sets are compressed.

Offset member 308 may include collar connector 318 and cross link holder 320. Collar connector 318 may be positioned over a collar of a bone fastener. A ball of a second dynamic posterior stabilization system may be positioned in collar connector 318 to form a multi-level construct. In some embodiments, an offset member may be used when stabilizing a single level. A closure member may be used to secure offset member 308 to the bone fastener. If another stabilization system is needed for the adjacent level at a future date, the closure member positioned on the bone fastener may be removed and a ball of a dampener system for the adjacent level may be positioned in collar connector 318.

An end of a rod may be positioned in cross link holder 320. A set screw may be threaded into the top portion of cross link holder 320 to secure the rod to offset member 308. A second end of the rod may be positioned in and secured to a cross link holder of a dynamic posterior stabilization system positioned on an opposite side of the spine. The cross link counteracts moments applied to the bone fastener because the dampener system is offset from the bone fastener.

Figure 47:
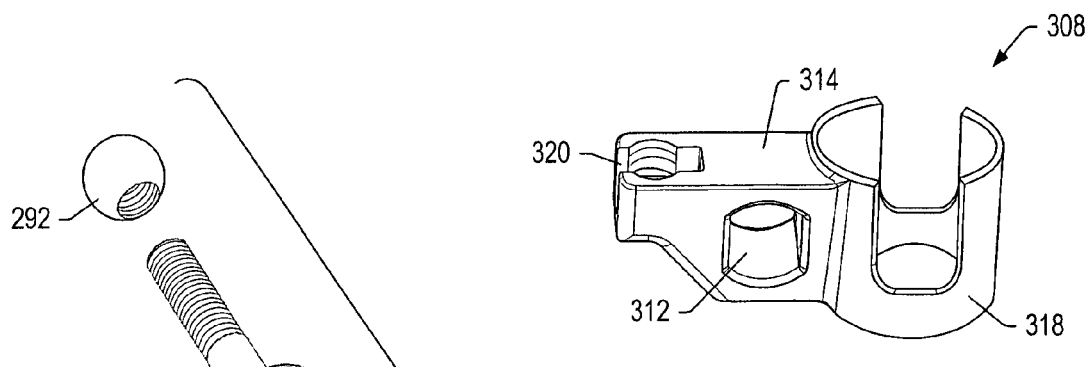
FIG. 47 depicts a perspective view of an embodiment of a medial offset member that may be used to form a dampener system that is positioned medial to a second bone fastener of a dynamic posterior stabilization system.

Offset member 308 depicted in FIG. 46 may be used to form a dynamic posterior stabilization system that is offset laterally relative to the spine. The offset member of the dynamic posterior stabilization system positioned on an opposite side of the spine may be a mirror image of offset member 308. FIG. 47 depicts offset member 308 that may be used in a dampener system to form a dynamic posterior stabilization system that is offset medially relative to the second bone fastener. Cross link holder 320 may be coupled to arm 314.

Figure 48:
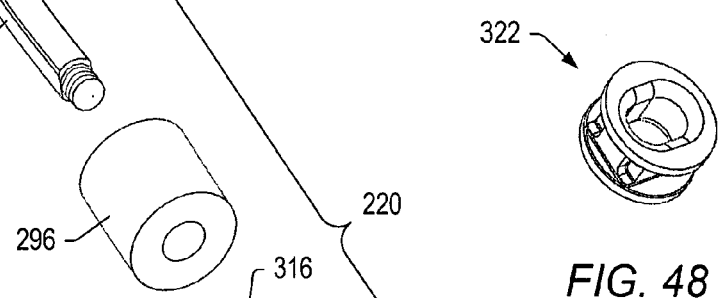
FIG. 48 depicts a perspective view of an embodiment of a sleeve that may be used to form an in-line dampener system.

In some embodiments, offset member 308 in FIG. 46 is replaced with a sleeve, such as sleeve 322 depicted in FIG. 48. Sleeve 322 allows for the formation of an in-line dampener system. Sleeve 322 may be coupled to a second bone fastener, such as second bone fastener 218 depicted in FIG. 30. In other embodiments, an in-line dampener system is formed using a sleeve shaped to fit in a collar such as the collar depicted in FIG. 29.

Figure 49:
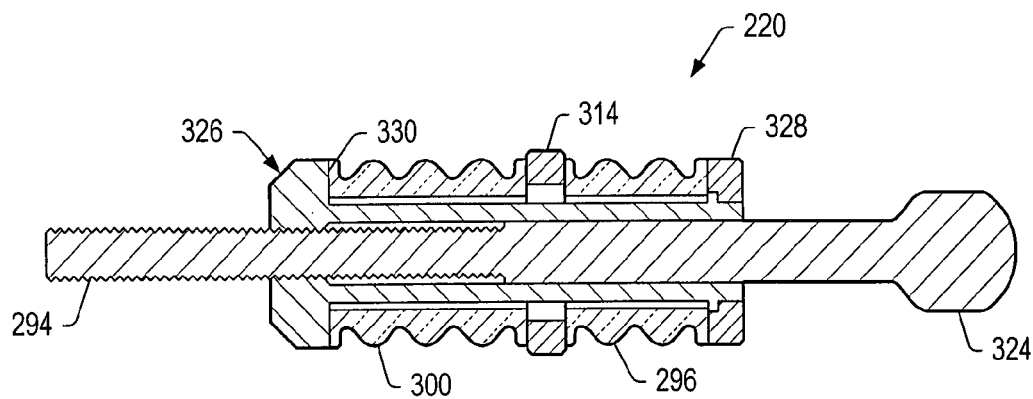
FIG. 49 depicts a cross-sectional representation of an embodiment of a dampener system.

In some embodiments, the length of the dampener system is adjusted by setting the position of a ball on a threaded portion of an elongated member. The ball is secured to the first bone fastener. In some embodiments, the portion of the dampener system that couples to the first bone fastener may be non-adjustable, and the portion of the dampener system that attaches to the second bone fastener may be adjustable. FIG. 49 depicts a cross-sectional representation of dampener system 220 wherein end 324 that attaches to the first bone fastener is not adjustable. Dampener system 220 includes elongated member 294, sleeve 326, first dampener set 296, offset arm 314, second dampener set 300, and stop 328.

Second dampener set 300 may be positioned against end 330 of sleeve 326. Offset arm 314 may be positioned against second dampener set 300. First dampener set 296 may be positioned against offset arm 314 and stop 328 may be secured to sleeve 326 to inhibit removal of the first dampener set, offset arm and second dampener set from the sleeve. In some embodiments, stop 328 may be welded to sleeve 326. A threaded portion of sleeve 326 located in end 330 may be threaded on elongated member 294 so that first dampener set 296 is positioned closest to end 324 of the elongated member. In some embodiments, offset arm 314 is a sleeve that couples to the second bone fastener to form an in-line dampener system.

A first bone fastener and a second bone fastener may be coupled to vertebrae. The length of the dampener system 220 may be adjusted by rotating sleeve 326. When the desired length is obtained, further rotation of the sleeve may be inhibited and excess portion of elongated member 294 may be removed before dampener system 220 is coupled to the bone fasteners.

Figure 50:
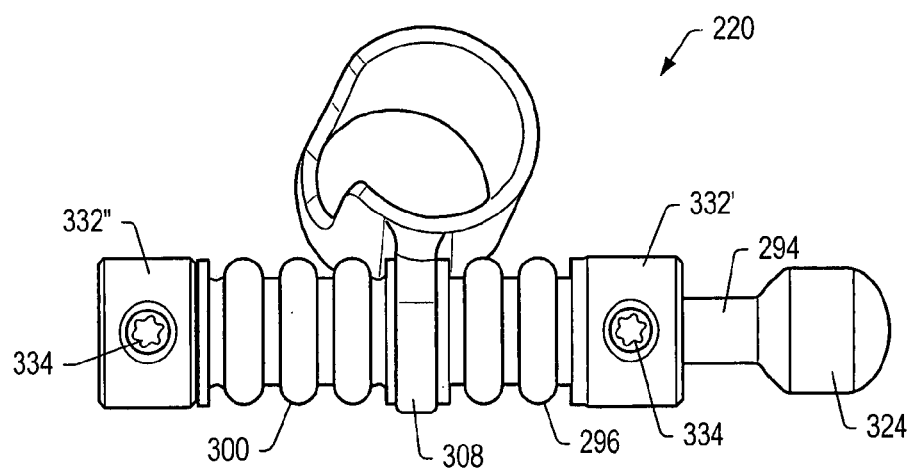
FIG. 50 depicts a top view of a dampener system embodiment.

FIG. 50 depicts an embodiment of dampener system 220 that uses set screws to fix the position of dampener sets 296, 300 on elongated member 294. Dampener sets 296, 300 and offset member 308 may be positioned on elongated member 294 between stops 332. In some embodiments, first dampener set 296 may be adhered to offset member 308 or to first stop 332' to facilitate positioning the first dampener set. In some embodiments, second dampener set 300 may be adhered to offset member 308 or to second stop 332" to facilitate positioning the second dampener set. The length of dampener system 220 may be set by moving stops 332 along elongated member 294 so that offset member 308 is at a desired position relative to end 324. When the desired position is obtained, set screws 334 may be threaded into stops 332 against elongated member 294 to set the length of dampener system 220. If a portion of elongated member 294 extends beyond stop 332", the portion may be removed. In some embodiments, a sleeve is substituted for offset member 308 to form an in-line dampener system.

Figure 51:
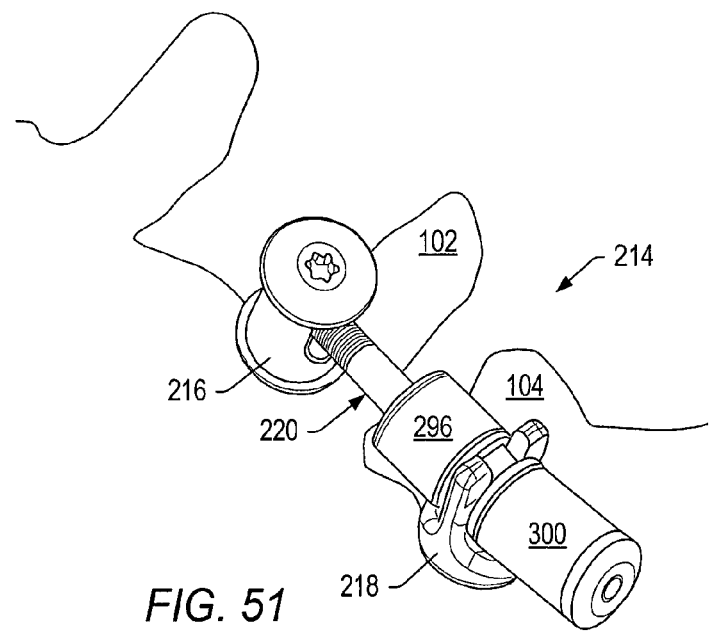
FIG. 51 depicts an embodiment of a dynamic posterior stabilization system coupled to vertebrae with the dampener sets positioned in a non-inverted orientation.

When the dampener system of a dynamic posterior stabilization system is coupled to the bone fasteners, the first bone fastener may be positioned in the lower vertebra of the vertebrae being stabilized, or in the upper vertebra of the vertebrae being stabilized. FIG. 51 depicts an in-line version of dynamic posterior stabilization system 214 at the S1-L5 level such that first bone fastener 216 is positioned in upper vertebra 102 (L5) and second bone fastener 218 is positioned in the lower vertebra 104 (S1). A dynamic posterior stabilization system positioned so that second dampener set 300 is the more caudal of dampener sets 296, 300 is in a non-inverted orientation.

Figure 52:
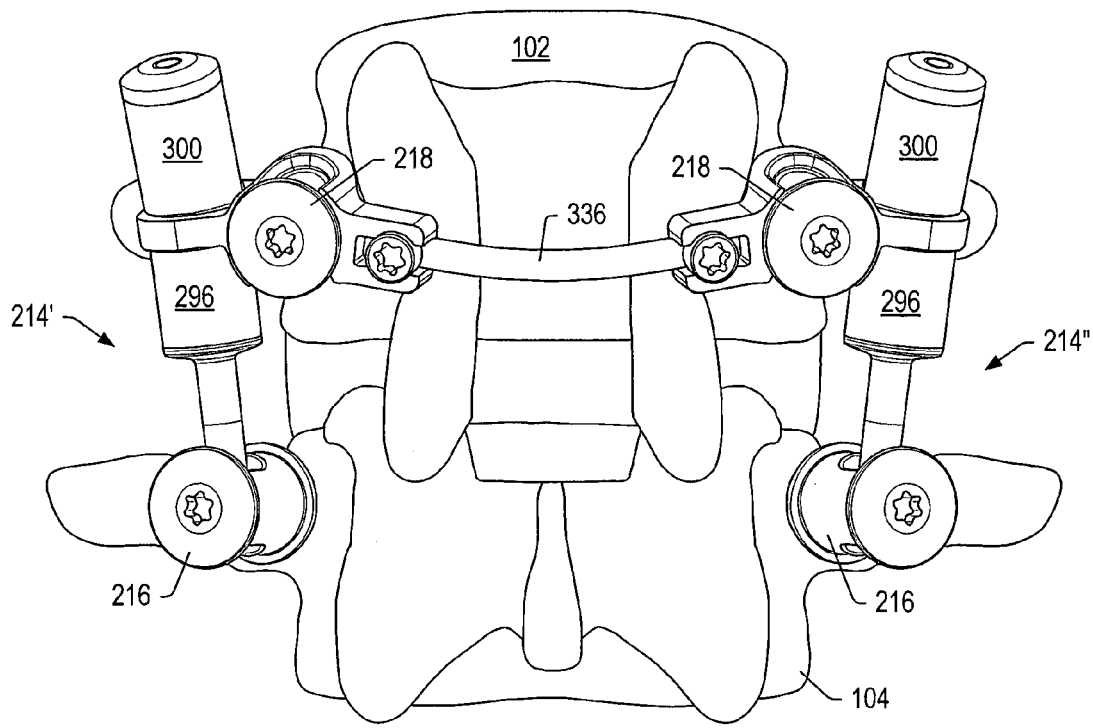
FIG. 52 depicts embodiments of dynamic posterior stabilization systems coupled to vertebrae with the dampener sets positioned in an inverted orientation.

FIG. 52 depicts laterally offset version of dynamic posterior stabilization systems 214 coupled to vertebrae such that first bone fasteners 216 is positioned in lower vertebra 104 (L5) and second bone fasteners 218 are positioned in upper vertebra 102 (e.g., L4). Cross link 336 secures first dynamic posterior stabilization system 214' to second dynamic posterior stabilization system 214". A dynamic posterior stabilization system positioned so that first dampener set 296 is the more caudal of dampener sets 296, 300 is in an inverted orientation.

Figure 53:
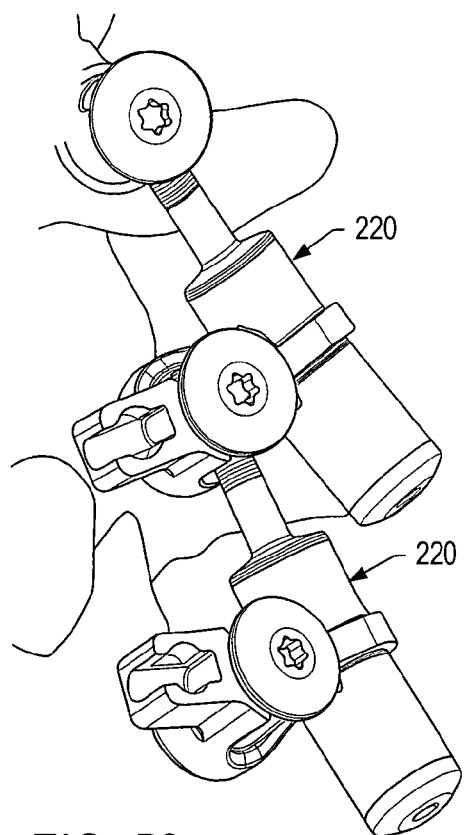
FIG. 53 depicts an embodiment of a two level dynamic posterior stabilization system.

For some stabilization procedures, a two level stabilization system may be installed. FIG. 53 depicts a two level stabilization system installed on one side of the spine. Dampener systems 220 are offset laterally, and the dampener systems are in non-inverted orientations. Other dampener system embodiments allow for medial offset. Multi-level stabilization systems may be formed in inverted or non-inverted orientations.

In the embodiment of dynamic posterior stabilization system depicted in FIG. 28, dampener system 220 includes washers on each side of the collar of second bone fasteners 218. Convex contours of the washers may be positioned in complementary concave recesses of the collar of the bone fastener. The convex contours may position dampener system 220 in the collar of second bone fastener 218 and eliminate the need for the dampener system to include a sleeve positioned in the collar of the second bone fastener. The washers may be used to compress the dampener when dampener system 220 is coupled to bone fasteners 216, 218.

Figure 54:
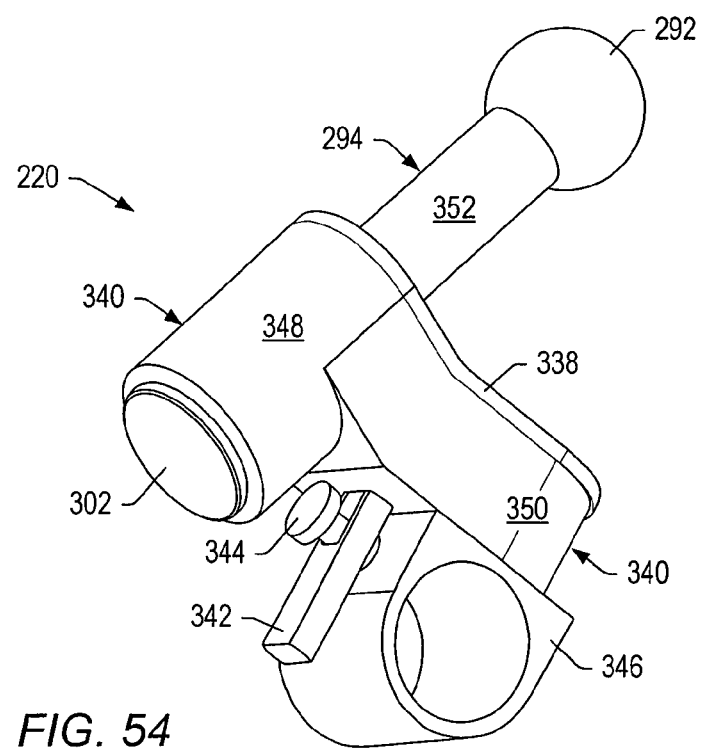
FIG. 54 depicts an embodiment of a side by side dampener system.

FIG. 54 shows an embodiment of dampener system 220. Dampener system 220 may include ball 292, elongated member 294, plate 338, dampener set 340, guide 342, pin 344, collar 346, and stop 302. Dampener set 340 may be a single irregularly shaped dampener, or a separate flexion dampener and a separate extension dampener positioned side by side. Plate 338 may be positioned against a first end of dampener set 340. Flexion dampener 348 of dampener set 340 may be coupled to elongated member 294. A first portion of guide 342 may be secured to plate 338. Pin 344 may be positioned through a slot in guide 342 and into collar 346. In some embodiments, pin 344 threads into collar 346.

Extension dampener 350 of dampener set 340 may be coupled to collar 346. A portion of elongated member 294 may pass through plate 338 and flexion dampener 348. Elongated member 294 may have first portion 352 with a diameter larger than the opening through the plate. A smaller diameter portion of elongated member 294 may pass through flexion dampener 348. Stop 302 may be secured to the end of elongated member 294 against flexion dampener 348.

Ball 292 may be coupled to a threaded portion of elongated member 294. Ball 292 may be rotated to change the length of dampener system 220. When the desired length of dampener system 220 is set, rotation of ball 292 may be inhibited and the ball may be positioned in the collar of a first bone fastener positioned in a first vertebra. Collar 346 may be secured to a second bone fastener positioned in a second vertebra. During extension or lateral bending towards the side of the spine that the bone fasteners are coupled to, compression of extension dampener 350 provides resistance to bending. First portion 352 of elongated member 294 pushes against plate 338. Extension dampener 350 is compressed between plate 338 and collar 346. Interaction between pin 344 and guide 342 accommodates reducing height of extension dampener 350. Stop 302 remains the same distance away from plate 338 so that there is no compression of flexion dampener 348.

During flexion and or lateral bending away from the side of the spine that the bone fastener are coupled to, compression of flexion dampener 348 provides resistance to bending. The first bone fastener moves away from the second bone fastener. Stop 302 is drawn towards plate 338. Flexion dampener 348 is compressed between stop 302 and plate 338. Extension dampener 350 does not compress.

Figure 55:
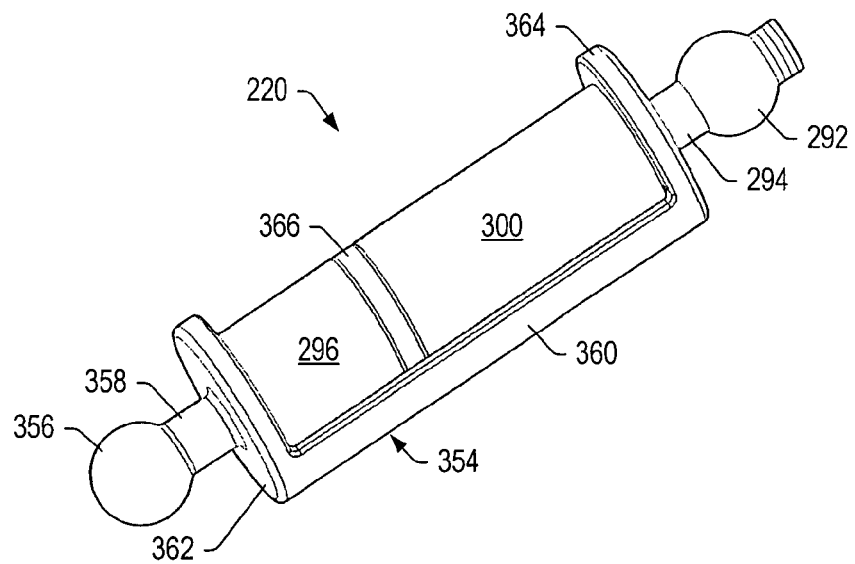
FIG. 55 depicts a perspective view of an embodiment of a dampener system that spans across a vertebra.

In some two level stabilization systems, positioning a bone fastener in the middle vertebra may not be possible. Size considerations may make extending the second dampener set beyond the second bone fastener problematic. An isolated dual dampener system with the dampener sets located between the bone fasteners may be used for two level stabilization system without a bone fastener positioned in the middle vertebra. FIG. 55 depicts an embodiment of dampener system 220. Dampener system 220 may include frame 354, first dampener set 296, second dampener set 300, elongated member 294, and ball 292. Ball 292 may be coupled to a threaded portion of elongated member 294. The length of dampener system 220 may be adjusted by rotating ball 292 to advance the ball on the threaded portion of elongated member 294. When the desired length of dampener system 220 is set, further rotation of ball 292 may be inhibited and excess length of elongated member 294 may be removed.

Frame 354 may include ball 356, shaft 358, support 360, first end 362, and second end 364. Ball 356 may be positioned in a bone fastener of the dynamic posterior stabilization system. Shaft 358 may be fixed to ball 356 and first end 362. In some embodiments, a portion of shaft 358 may extend through first end 362. The portion of shaft 358 that extends through first end 362 may be positioned in an opening in first dampener set 296 to position the first dampener set relative to support 360. In some embodiments, first dampener set 296 is adhered to first end 362.

Support 360 connects first end 362 to second end 364. In some embodiments, support 360 is a wall that partially surrounds dampener sets 296, 300. In some embodiments, support 360 is formed of one or more braces that support first end 362 and second end 364.

Elongated member 294 may include slide 366. Second dampener set 300 may be placed against slide 366. The other end of elongated member may be positioned through an opening in second end 364 of frame 354.

Ball 292 and ball 356 may be secured to bone fasteners positioned in vertebrae (e.g., S1 and L4). During extension and/or lateral bending towards the side of the spine that the dynamic posterior stabilization system is coupled to, the first bone fastener moves towards second bone fastener and slide 366 compresses first dampener set 296 against first end 362. During flexion and/or lateral bending away from the side of the spine that the dynamic posterior stabilization system is coupled to, the first bone fastener moves away from the second bone fastener and 366 compress second dampener set 300 against second end 364. Frame 354 may rotate relative to elongated member 294.

For isolated dual dampener systems, the first dampener set is compressed during extension while the second dampener set is not compressed. Also, the second dampener set is compressed during flexion while the first dampener is not compressed. The length of the second dampener set may be reduced if both dampener sets are compressed during flexion and only the first dampener set is compressed during extension. Such a dampener system is a partially shared dual dampener system. In some embodiments, partially shared dual dampener systems are used to stabilize two level systems without a bone fastener positioned in the middle vertebra (e.g., an L4-S1 stabilization system without a bone fastener secured to L5).

Figure 56:
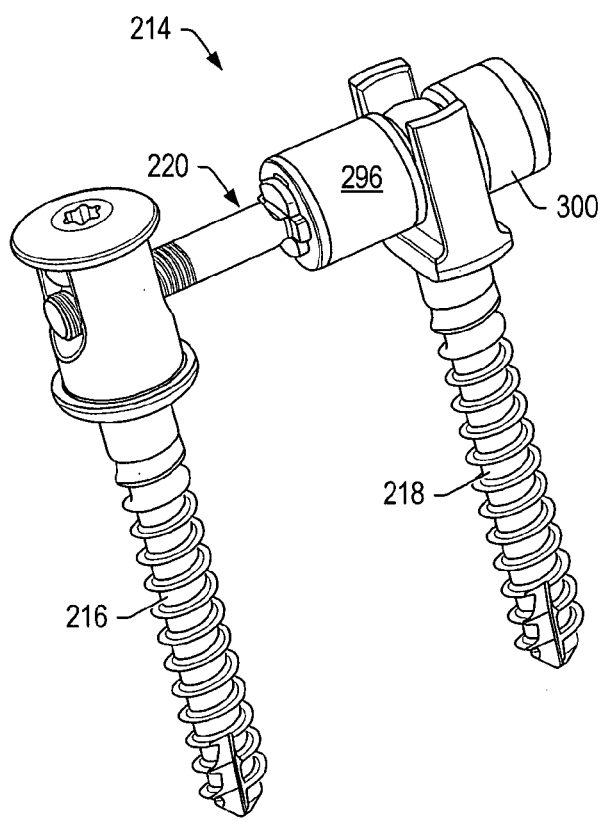
FIG. 56 depicts a perspective view of an embodiment of a dynamic posterior stabilization system with an in-line, partially shared dual dampener system in a neutral position.

A dynamic posterior stabilization system with a partially shared dual dampener system is depicted in FIG. 56. Dynamic posterior stabilization system 214 is an in-line, partially shared dual dampener system that includes bone fasteners 216, 218 and dampener system 220. Dynamic posterior stabilization system 214 is shown in a neutral position (i.e., no added compression of dampener sets 296, 300). Dynamic posterior stabilization system 214 may be installed in a non-inverted orientation (i.e., where bone fastener 216 is in an upper vertebra of the vertebrae to be stabilized) or in an inverted orientation (i.e., where bone fastener 216 is in a lower vertebra of the vertebrae to be stabilized). In some embodiments, the dampener system includes an offset member that allows the dampener system to be offset laterally from the second bone fastener. In some embodiments, the dampener system includes an offset member that allows the dampener system to be offset medially from the second bone fastener. The use of dampener systems with offset members may allow for the formation of multi-level constructs.

Figure 57:
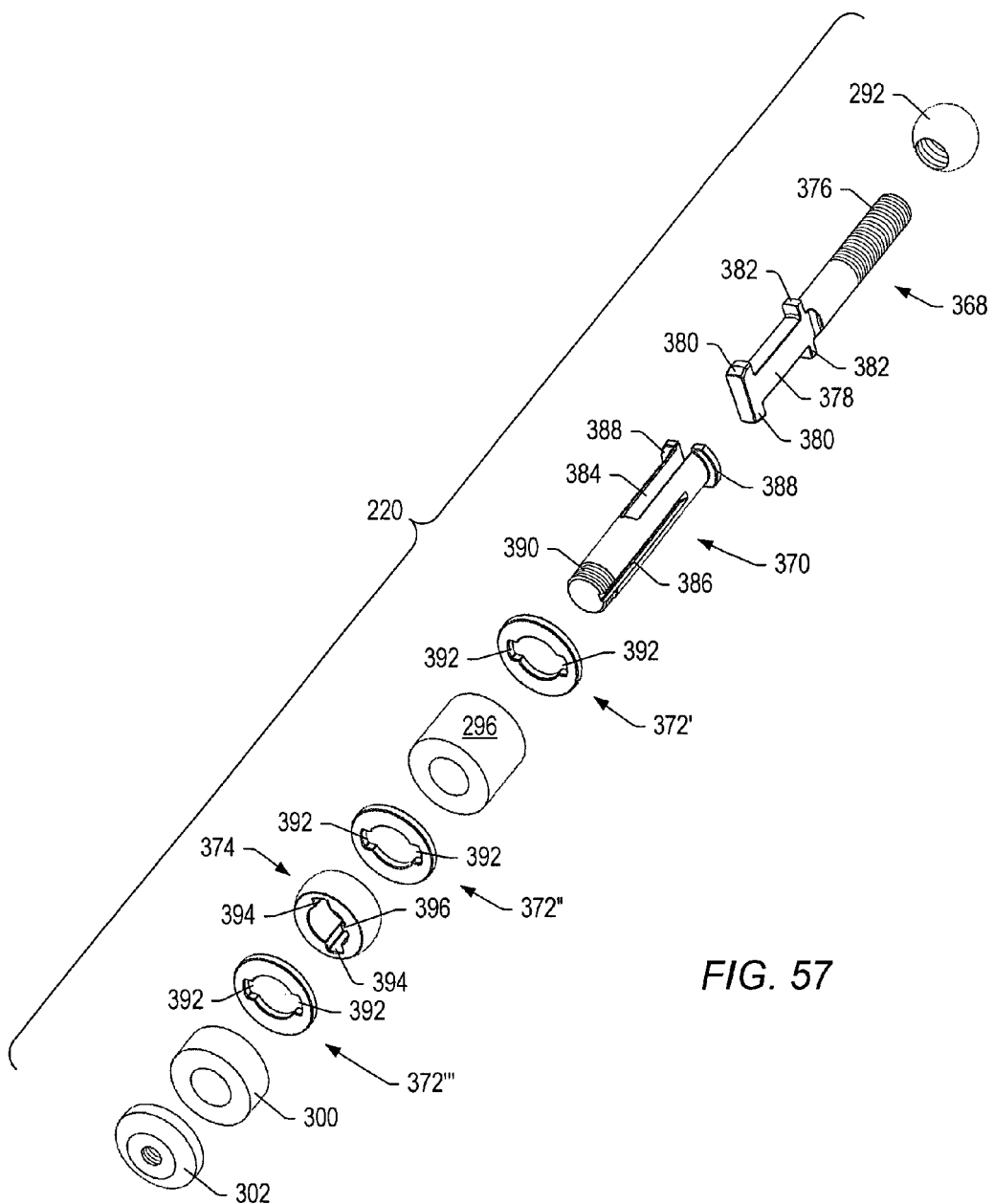
FIG. 57 depicts an exploded view of an embodiment of an in-line, partially shared dual dampener system.

FIG. 57 depicts the components of an in-line embodiment of dampener system 220. Dampener system 220 may include ball 292, first elongated member 368, second elongated member 370, washers 372, first dampener set 296, second dampener set 300, sleeve 374, and stop 302. In some embodiments, the surfaces of washers 372 that contact dampener sets 296, 300 are curved (e.g., spherically contoured).

First elongated member 368 may include threading 376, flat portion 378, first shoulder 380 and second shoulder 382. Threading 376 may complement threading on the inside of ball 292. Second elongated member 370 may include slot 384, groove 386, retainers 388, and threading 390. Flat portion 378 of first elongated member 368 may be placed in slot 384 of second elongated member 370 to form a variable length elongated member. A protrusion in sleeve 374 may be positioned in groove 386. Retainers 388 may provide a stop beyond which washer 372' cannot pass on second elongated member 370. Threading 390 may complement threading on the inside of stop 302.

Flat portion 378 may be placed in slot 384. First washer 372' may be placed on second elongated member 370 against retainers 388. Initially, slots 392 of first washer 372' are aligned with first shoulder 380 of first elongated member 368 to allow placement of the first washer on second elongated member 370. After slots 392 pass first shoulder 380, first washer 372' may be rotated so that slots 392 do not align with first shoulder 380. First dampener set 296 may be positioned on second elongated member 370 against first washer 372'. In some embodiments, the central passage of first dampener set 296 is shaped so that the first dampener passes past second shoulder 382 of first elongated member 368. In other embodiments, first dampener is forced past first shoulder 380 of first elongated member 368.

After first dampener set 296 is positioned against first washer 372', second washer 372" may be placed on second elongated member 370 against the first dampener set. Initially, slots 392 of second washer 372" are aligned with first shoulder 380 of first elongated member 368 to allow placement of the second washer on second elongated member 370.

After second washer 372" passes first shoulder 380, the second washer may be rotated so that slots 392 do not align with the first shoulder.

Slots 394 in sleeve 374 may be aligned with first shoulder 380 of first elongated member 368, and protrusion 396 may be oriented so that the protrusion will fit in groove 386 of second elongated member 370. Sleeve 374 may be placed on second elongated member 370 against second washer 372". Placement of protrusion 396 in groove 386 ensures that first shoulder 380 is always aligned with slots 394 in sleeve 374.

Third washer 372'" may be placed on second elongated member 370 against sleeve 374. Third washer 372'" may include slots 392 so that only one type of washer is used to form dampener system 220. In some embodiments, third washer does not include slots. After third washer 372'" is positioned on second elongated member 370, second dampener set 300 may be placed on the second elongated member against third washer 372'". Stop may be rotated on threading 390 of second elongated member 370. When stop 302 is in a desired position, the stop may be welded or otherwise secured to second elongated member 370.

To insert the dynamic posterior stabilization system in a patient, the patient is placed in a neutral position with substantially no flexion, extension, lateral bending or axial rotation. The first bone fastener is secured to the first vertebra of the vertebra to be stabilized. The second bone fastener is secured to the second vertebra of the vertebra to be stabilized. The ball of the dampener system is adjusted so that the ball fits in the collar of the first bone fastener and the sleeve fits in the collar of the second bone fastener with substantially no additional compression of the dampener sets. After the ball is set to the desired position on the elongated member, rotation of the ball may be inhibited and any excess length of the elongated member may be removed. The ball may be positioned in the collar of the first bone fastener, and sleeve may be positioned in the collar of the second bone fastener. A closure member may be secured to the collar of the first bone fastener. The closure member attached to the collar of the first member may secure the ball in the collar and inhibit axial movement of the ball relative to the first bone fastener. In some embodiments, a closure member is secured to the collar of the second bone fastener. The closure member secured to the second bone fastener may inhibit removal of the sleeve from the second bone fastener.

Figure 58:
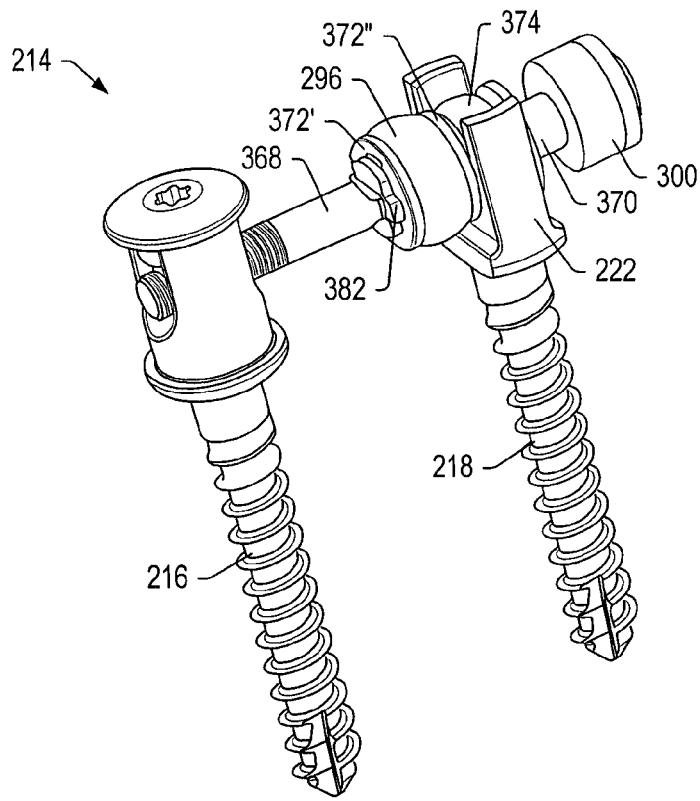
FIG. 58 depicts a perspective view of an embodiment of a dynamic posterior stabilization system with a first dampener set of an in-line, partially shared dual dampener system in compression.

FIG. 58 depicts dynamic posterior stabilization system 214 with first dampener 296 set compressed. During extension and/or during lateral bending towards the side of the spine to which the dynamic posterior stabilization system is attached, first bone fastener 216 and second bone fastener 218 move relatively closer together and compression of first dampener set 296 resists relative movement of the bone fasteners. To compress first dampener set 296, sleeve 374 slides along second elongated member 370 towards the first dampener set. Collar 222 of second bone fastener 218 engages second washer 372" and moves towards first bone fastener 216. Movement of first washer 372' is inhibited by second shoulder 382 of first elongated member 368. First dampener set 296 is compressed between first washer 372' and second washer 372". Second dampener set 300 is uncompressed.

Figure 59:
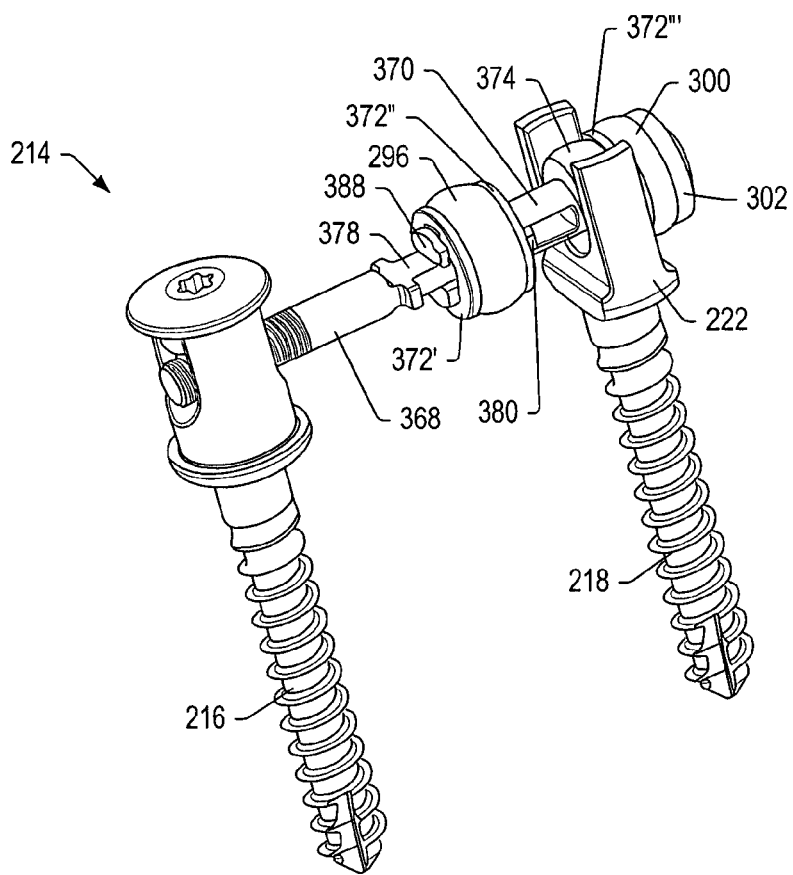
FIG. 59 depicts a perspective view of an embodiment of a dynamic posterior stabilization system with a first dampener set and a second dampener set of an in-line, partially shared dual dampener system in compression.

FIG. 59 depicts dynamic posterior stabilization system 214 with first dampener 296 and second dampener set 300 compressed. During flexion and/or during lateral bending away from the side of the spine to which dynamic posterior stabilization system 214 is attached, first bone fastener 216 and second bone fastener 218 move relatively away from each other and compression of first dampener set 296 and second dampener set 300 resists relative movement of the bone fasteners. To compress second dampener set 300, sleeve 374 slides along second elongated member 370 towards stop 302. Collar 222 of second bone fastener 218 engages third washer 372''' and compresses second dampener set 300 against stop 302. To compress first dampener set 296, second elongated member 370 slides along flat portion 378 of first elongated member 368 away from first bone fastener 216. Retainers 388 engage first washer 372' and draw first washer and first dampener set 296 towards second washer 372". First shoulders 380 of first elongated member 368 inhibit movement of second washer 372". First dampener set 296 is compressed between first washer 372' and second washer 372".

Figure 60:
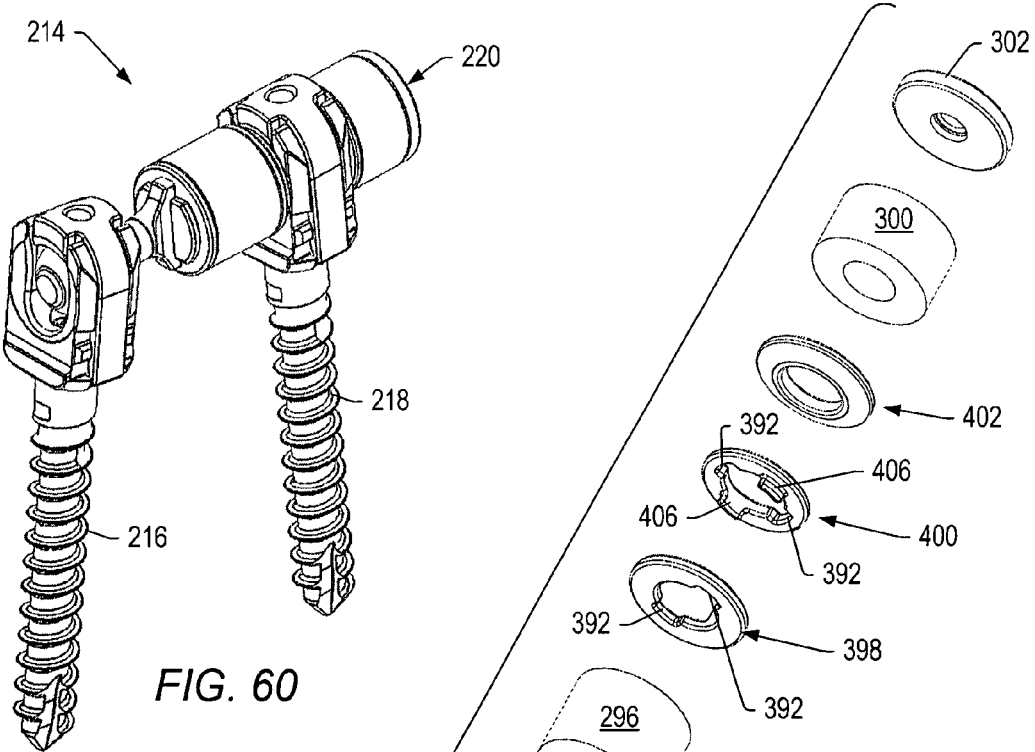
FIG. 60 depicts a perspective view of an embodiment of an in-line, partially shared dual dampener system.
Figure 61:
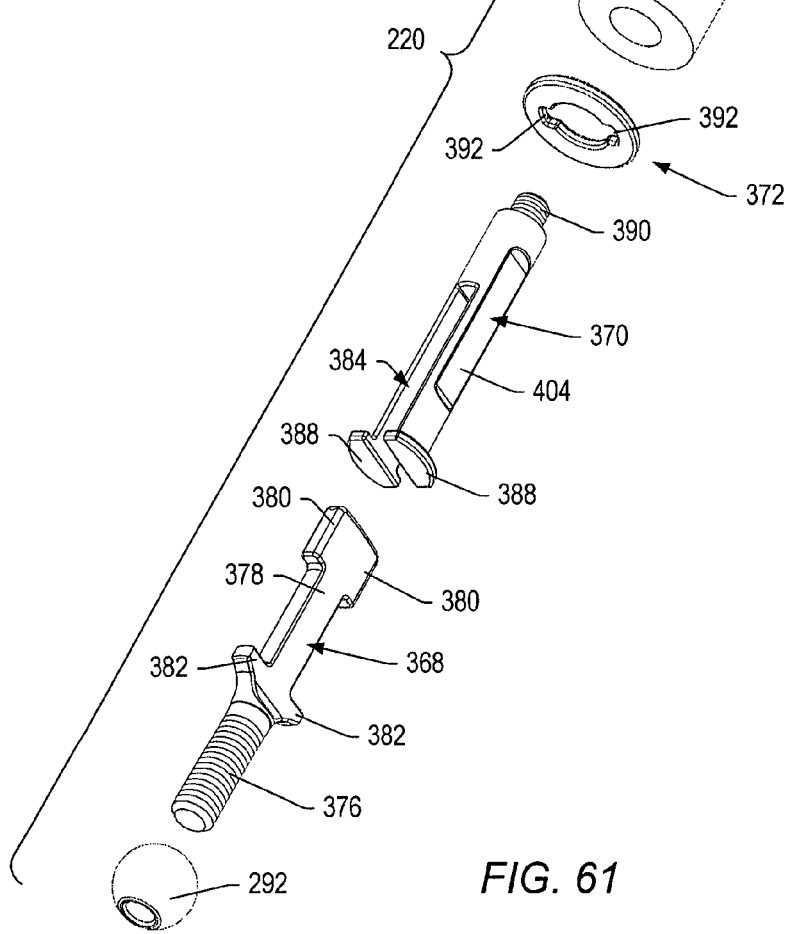
FIG. 61 depicts an exploded view of the in-line, partially shared dual dampener system depicted in FIG. 60.

FIG. 60 depicts an embodiment of dynamic posterior stabilization system 214 with identical bone fasteners 216, 218 and in-line, partially shared dual dampener system 220 in a neutral position. FIG. 61 depicts an exploded view of dampener system 220 depicted in FIG. 60. Dampener system 220 may include ball 292, first elongated member 368, second elongated member 370, keyed washer 372, first dampener set 296, first keyed linking washer 398, second keyed linking washer 400, washer 402, second dampener set 300, and stop 302.

First elongated member 368 may include threading 376, flat portion 378, first shoulder 380 and second shoulder 382. Threading 376 may complement threading on the inside of ball 292. Second shoulder may provide a stop for washer 372 on first elongated member 368.

Second elongated member 370 may include slot 384, retainers 388, flats 404, and threading 390. Flat portion 378 of first elongated member 368 may be placed in slot 384 of second elongated member 370 to form a variable length elongated member. Flats 404 may limit axial rotation of second elongated member 368 when the elongated member is positioned in a collar of a bone fastener. Retainers 388 may provide a stop beyond which washer 372 cannot pass on second elongated member 370. Threading 390 may complement threading on the inside of stop 302.

Flat portion 378 may be placed in slot 384. Washer 372 may be placed on second elongated member 370 against retainers 388. Initially, slots 392 of washer 372 are aligned with first shoulder 380 of first elongated member 368 to allow placement of the washer on second elongated member 370. After slots 392 pass first shoulder 380, washer 372 may be rotated so that slots 392 do not align with the first shoulder. First dampener 296 may be positioned on second elongated member 370 against washer 372. In some embodiments, the central passage of first dampener set 296 is shaped so that the first dampener passes past first shoulder 380 of first elongated member 368. In other embodiments, first dampener is forced past first shoulder 380 of first elongated member 368.

After first dampener set 296 is positioned against washer 372, first keyed linking washer 398 may be placed on second elongated member 370 against the first dampener set. Initially, slots 392 of first keyed linking washer 398 are aligned with first shoulder 380 of first elongated member 368 to allow placement of the first keyed linking washer on second elongated member 370. First key linking washer 398 may include tabs that are positioned to fit in slots 392 of second keyed linking washer 400. Second keyed linking washer 400 may be placed on second elongated member 370 against first keyed linking washer 398. Initially, slots 392 of second keyed linking washer 400 are aligned with first shoulder 380. After second keyed linking washer 400 passes first shoulder 380, first keyed linking washer 398 may be linked to the second keyed linking washer by rotating the second keyed linking washer and/or the first keyed linking washer and placing tabs 406 of the second keyed washer in slots 392 of the first keyed washer, and the tabs of the first keyed washer in slots 392 of the second keyed washer. Linking first keyed linking washer 398 to second keyed linking washer 400 inhibits movement of the linked washers past first shoulder 380.

Washer 402 may be placed on second elongated member 370. Second dampener set 300 may be placed on second elongated member 370. Stop 302 may be threaded on second elongated member 370. Stop 302 may be spiked, welded or otherwise secured to second elongated member 370.

The surface of second keyed linking washer 400 that faces away from first dampener set 296 may have a spherical contour. The spherical contour may complement a concave recess in the collar of the bone fastener that the dampener system is to be coupled to (e.g., concave recess 244 depicted in FIG. 31). Similarly, the surface of washer 402 that faces away from second dampener set 300 may have a spherical contour. The spherical contour may complement the concave surface in the collar of the bone fastener that the dampener system is to be coupled to.

During insertion in a patient, the bone fasteners are positioned in the vertebrae to be stabilized. The appropriately sized dampener system is selected. The ball of the dampener system may be rotated to adjust the length of the dampener system so that the ball fits in the collar of a first bone fastener and the spherically contoured surface of the second keyed linking washer is positioned in the concave recess of the collar of the second bone fastener. The washer with the spherical contour positioned next to the second dampener set may be used to compress the second dampener set against the stop so that the dampener system can be positioned in the collar of the second bone fastener. Once the dampener system is positioned in the collar of the second bone fastener, the washer may be released and closure members may be coupled to the bone fasteners to secure the dampener system to the bone fasteners.

During extension and/or lateral bending towards the side of the spine to which the dynamic posterior stabilization system is attached, the first bone fastener and second bone fastener move relatively closer together. Compression of the first dampener set resists relative movement of the bone fasteners towards each other. During flexion and/or lateral bending away from the side of the spine to which the dynamic posterior stabilization system is attached, the first bone fastener and second bone fastener move relatively farther apart. Compression of the first dampener set and the second dampener set resist relative movement of the bone fasteners away from each other.

Figure 62:
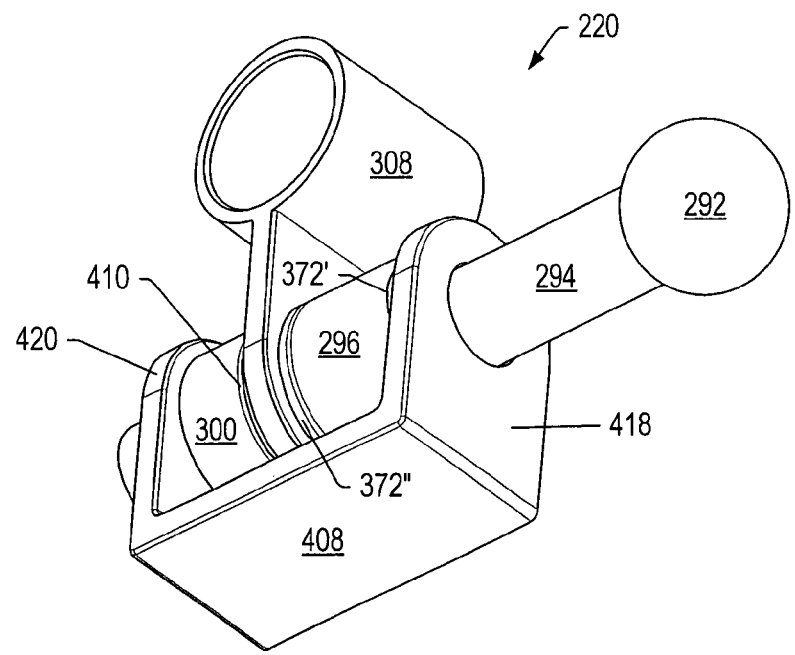
FIG. 62 depicts a perspective view of an embodiment of an offset, partially shared dual dampener system with an external frame.

FIG. 62 depicts an embodiment of offset, partially shared dual dampener system 220 in a neutral position. Dampener system 220 may include ball 292, elongated member 294, frame 408, first washer 372', first dampener set 296, second washer 372", offset member 308, third washer 410, and second dampener set 300.

Figure 63:
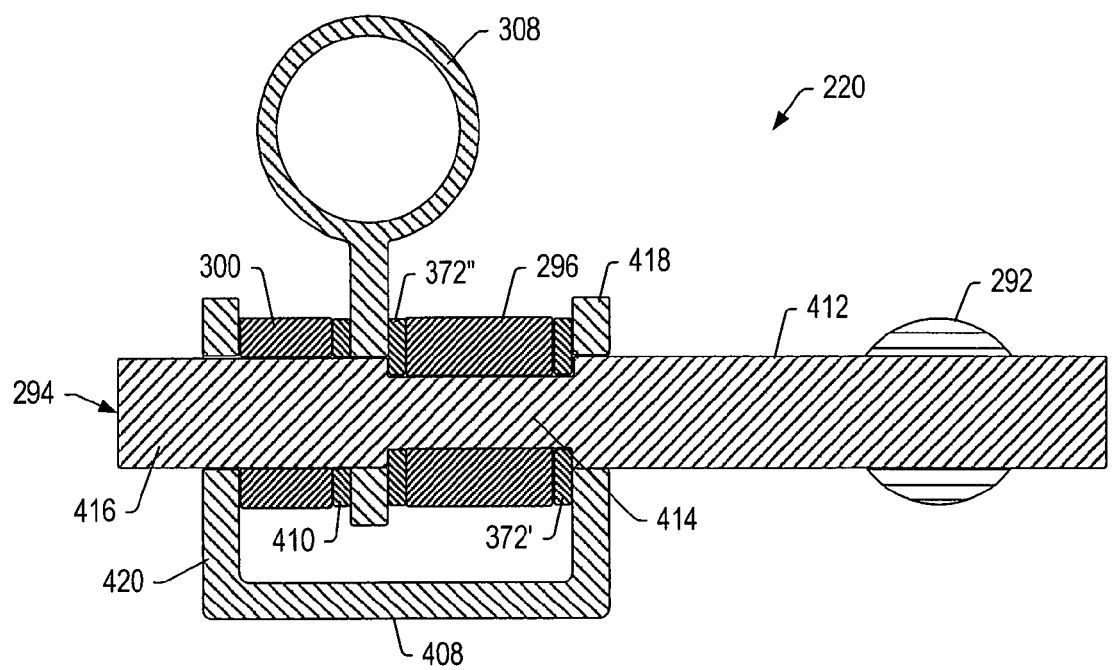
FIG. 63 depicts a cross-sectional representation of an embodiment of an offset, partially shared dual dampener system with an external frame.

FIG. 63 depicts a cross-sectional representation of dampener system 220. Elongated member 294 may include first portion 412, second portion 414, and third portion 416. The diameter of second portion 414 is less than the diameter of first portion 412 and third portion 416. The diameter of first portion 412 is smaller than the diameter of the opening through first arm 418 of frame 408. The diameter of first portion 412 is greater than a diameter of the opening through first washer 372' so that the first portion provides a stop for the first washer on elongated member 294. The diameter of the opening through first washer 372' is greater than the diameter of second portion 414. The length of second portion 414 may be substantially the same length as the sum of the lengths of first washer 372', first dampener set 296 in the neutral position, and second washer 372". The diameter of third portion 416 is greater than a diameter of the opening through second washer 372" and less than a diameter of the opening through offset member 308. Third portion 416 passes through third washer 410, second dampener set 300 and second arm 420 of frame 408.

In the neutral position shown in FIG. 62, first arm 418 of the frame is adjacent to first washer 372', and second arm 420 of frame 408 is positioned on elongated member 294 adjacent to second dampener set 300. Ball 292 may be secured to a first bone fastener positioned in a first vertebra. Offset member 308 may be secured to a second bone fastener positioned in a second vertebra.

The first bone fastener may move towards the second bone fastener when the vertebrae are subjected to extension and/or to lateral bending towards the side that dampener system 220 is coupled to. Compression of first dampener set 296 provides resistance to such extension and/or lateral bending. First portion 412 of elongated member 294 engages first washer 372' and moves the first washer towards second washer 372". Second washer 372" moves against offset member 308. First dampener set 296 is compressed between first washer 372" and second washer 372". Third portion 416 of elongated member 294 slides outwards through second arm 420 of frame 408 and does not compress second dampener set 300.

The first bone fastener may move away from the second bone fastener when the vertebrae are subjected to flexion and/or to lateral bending away from the side that dampener system 220 is coupled to. Compression of first dampener set 296 and second dampener set 300 provides resistance to such flexion and/or lateral bending. When the first bone fastener moves away from the second bone fastener, third portion 416 of elongated member 294 engages second washer 372" and draws the second washer towards first washer 372'. Movement of first washer 372' is stopped by first arm 418 of frame 408. First dampener set 296 is compressed between first washer 372' and second washer 372". Force applied to first arm 418 by first washer 372' moves frame 408 towards ball 292 and the first bone fastener and compresses second dampener set 300 between second arm 420 and third washer 410. Third washer 410 pushes against offset member 308.

Figure 64:
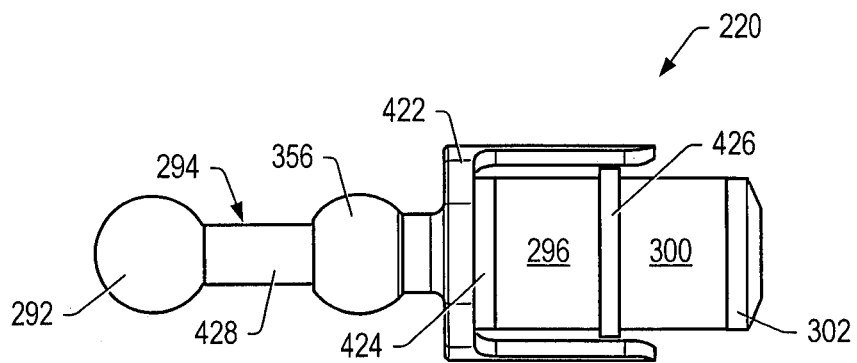
FIG. 64 depicts a front view of an embodiment of an in-line partially shared dual dampener system in a neutral position.

For some patients, space limitation or other considerations may require that the dampener sets of the dampener system not be located between the bone fasteners. FIG. 64 depicts an embodiment of dampener system 220 in a neutral position. Dampener system 220 is an in-line, partially shared dual dampener system. Dampener system 220 may include ball 292, elongated member 294, frame 422, washer 424, first dampener set 296, slide 426, second dampener set 300, and stop 302. Frame 422 may include second ball 356. Dampener sets 296, 300 of dampener system 220 are external to balls 292, 356 that couple to bone fasteners of the dynamic posterior stabilization system. In some embodiments, the surfaces of washers 424, slide 426 and other portions that contact dampener sets 296, 300 are curved (e.g., spherically contoured).

Ball 292 may be positioned on a threaded portion of elongated member 294. Rotation of ball 292 relative to elongated member 294 allows for adjustment of the distance between balls 292, 356. Ball 292 may be rotated on elongated member 294 until the distance between balls 292, 356 allows the balls to be positioned in collars of bone fasteners that are secured to vertebrae. In some embodiments, further rotation of ball 292 is inhibited once the desired distance between balls 292, 356 is established.

Figure 65:
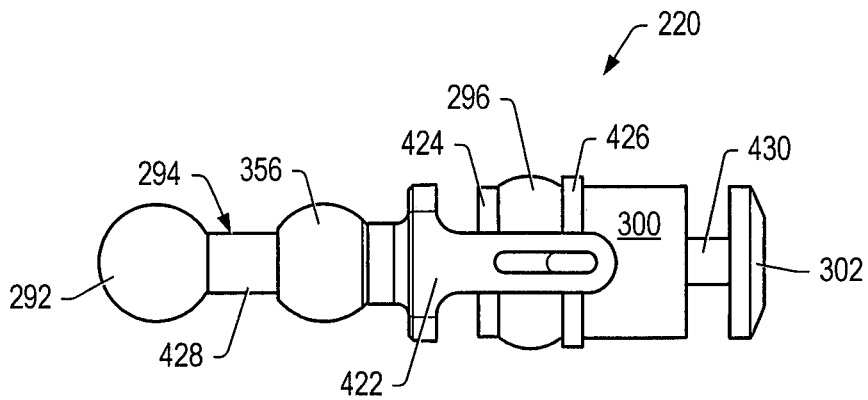
FIG. 65 depicts a side view of an embodiment of an in-line partially shared dual dampener system with the first dampener set compressed.

Elongated member 294 may have first portion 428 and a second portion (second portion 430 depicted in FIG. 65). The diameter of first portion 428 is larger than the diameter of the second portion. A shoulder is present at the transition between first portion and the second portion. First portion 428 is sized slightly smaller than a passage in second ball 356 of frame 422. Openings through washer 424 and slide 426 are sized slightly larger than second portion 430, but smaller than first portion 428. Washer 424 is positioned on elongated member 294 against the bottom of frame 422. First dampener set 296 is positioned against washer 424. Slide 426 is positioned against first dampener set 296 with protrusions of the slide extending into slots in the arms of frame 422 (shown in FIG. 65 and FIG. 66). Second dampener set 300 is positioned against slide 426, and stop 302 is secured to elongated member 294 against the second dampener set.

FIG. 65 depicts dampener system 220 when first dampener set 296 is compressed. Second ball 356 of frame 422 is moved towards ball 292. Washer 424 is positioned against the shoulder formed at the transition between first portion 428 and second portion 430 of elongated member 294. First dampener set 296 is compressed between washer 424 and slide 426. Second dampener set 300 is uncompressed. First dampener set 296 may be compressed as shown when dampener system 220 is coupled to bone fastener secured to vertebrae, and when the vertebrae are subjected to extension and/or to lateral bending towards the side of the spine that the dampener system is secured to.

Figure 66:
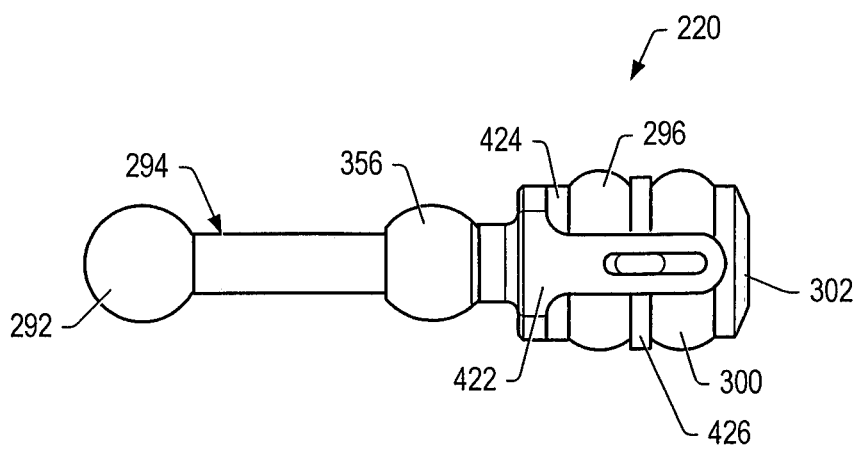
FIG. 66 depicts a side view of an embodiment of an in-line partially shared dual dampener system with the first dampener set and the second dampener set compressed.

FIG. 66 depicts dampener system 220 when first dampener set 296 and second dampener set 300 are compressed. Second ball 356 of frame 422 is moved away from ball 292 along elongated member 294. Washer 424 is positioned in the bottom of frame 422. Frame 422 moves toward stop 302 and first dampener set is compressed between washer 424 and slide 426 while second dampener set 300 is compressed between the slide and the stop. Dampener set 296, 300 may be compressed as shown when dampener system 220 is coupled to bone fastener secured to vertebrae, and when the vertebrae are subjected to flexion and/or to lateral bending away from the side of the spine that the dampener system is secured to.

Partially shared dual dampener systems may be positioned on bone fastener so that the dampener sets are below the lower vertebra of the vertebrae to be stabilized (i.e., in a non-inverted orientation), or so that the dampener sets are above the upper vertebra of the vertebrae to be stabilized (i.e., in an inverted orientation). In some embodiments, the partially shared dual dampener system may include an offset member that allows the dampener system to be positioned medially or laterally to the one or both of the bone fasteners. For example, a second ball may be coupled to the side of the frame. An offset dual dampener system may require a cross link to a dynamic posterior stabilization system positioned on the opposite side of the spine.

Figure 67:
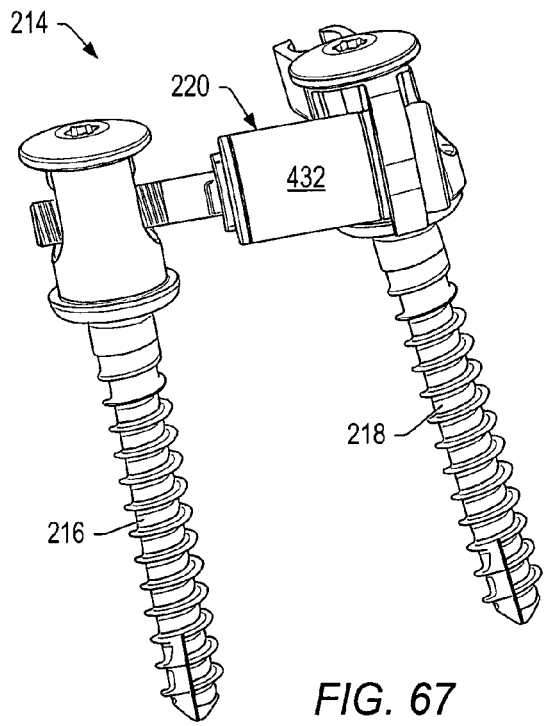
FIG. 67 depicts a perspective view of a dynamic posterior stabilization system with an offset, single dampener system in a neutral position.

For some patients, space limitations or other considerations may require a single dampener set that is positioned between the bone fastener fasteners of the dynamic posterior stabilization system. FIG. 67 depicts an embodiment of dynamic posterior stabilization system 214 with dampener system 220 in a neutral position. Dampener system 220 is a single dampener system. While dual dampener systems allow for different maximum amounts of flexion and extension, single dampener system 220 may allow for the same maximum amount of flexion and extension. Dual dampener systems and single dampener systems may provide for increasing resistance to flexion/extension and/or lateral bending with increased bending. In some embodiments, the dynamic interbody device or devices used in conjunction with the dynamic posterior stabilization system or systems set the maximum amount of flexion/extension and/or lateral bending of stabilized vertebrae. In some embodiments, the dynamic posterior stabilization systems set the maximum amount of flexion/extension and/or lateral bending of stabilized vertebrae. In some embodiments, single dampener systems are used to stabilize two level systems without a bone fastener positioned in the middle vertebra (e.g., an L4-S1 stabilization system without a bone fastener secured to L5).

Figure 68:
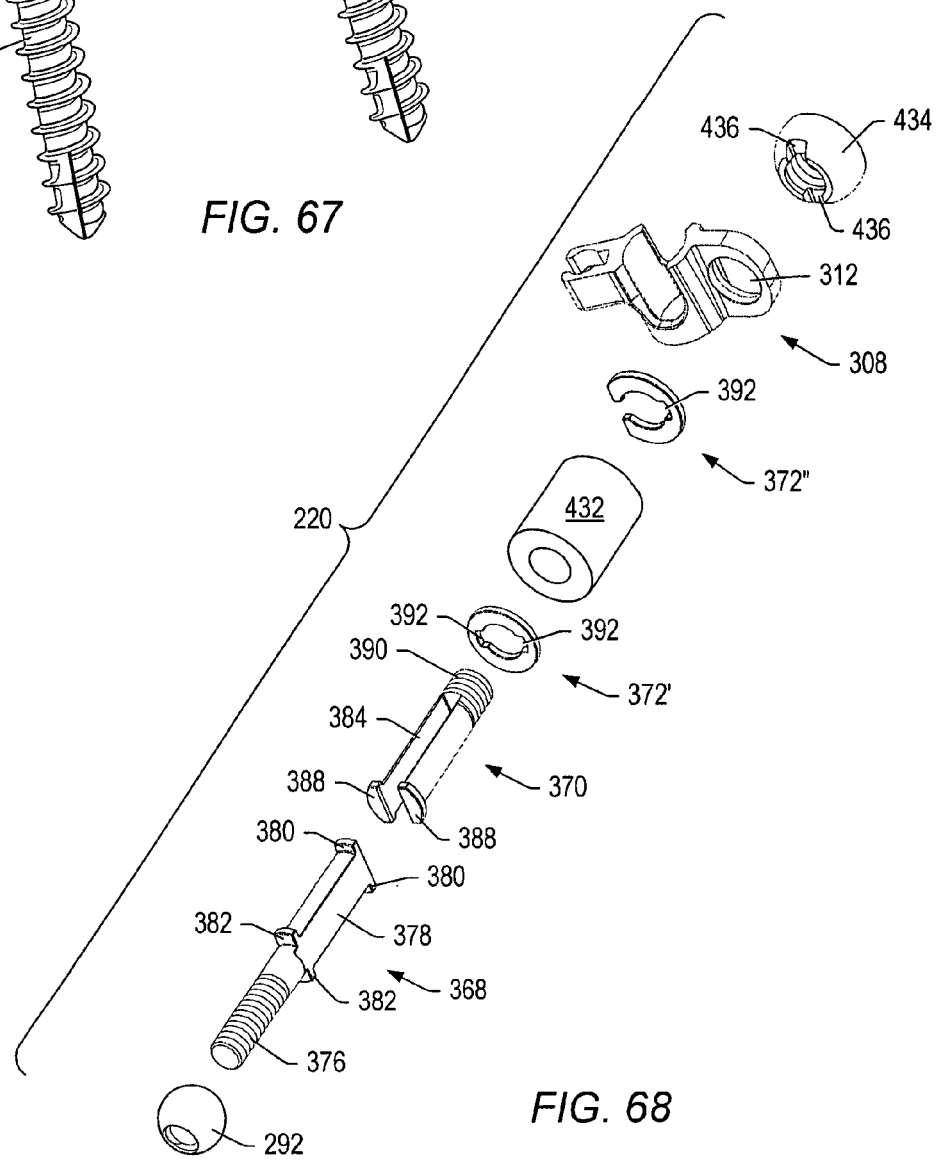
FIG. 68 depicts an exploded view of an offset, single dampener system.

FIG. 68 depicts the components of an offset embodiment of single dampener system 220. Single dampener system 220 may include ball 292, first elongated member 368, second elongated member 370, washers 372, dampener set 432, offset member 308, and end piece 434. Dampener set 432 may be compressed during flexion, extension and lateral bending. To accommodate compression of dampener set 432, the length of the elongated member formed by first elongated member 368 and second elongated member 370 changes. In some embodiments, the surfaces of washers 372 that contact dampener set 432 are curved (e.g., spherically contoured).

First elongated member 368 may include threading 376, flat portion 378, first shoulder 380 and second shoulder 382. Threading 376 may complement threading on the inside of ball 292. Second elongated member 370 may include slot 384, retainers 388, and threading 390. Flat portion 378 may be placed in slot 384 to form a variable length elongated member. Retainers 388 may provide a stop beyond which washer 372' cannot pass on second elongated member 370. Threading 390 may complement threading on the inside of end piece 434.

First washer 372' may be placed on second elongated member 370. Initially, slots 392 of first washer 372' are aligned with first shoulder 380 of first elongated member 368 to allow placement of the first washer on second elongated member 370. After slots 392 pass first shoulder 380, first washer 372' may be rotated so that slots 392 do not align with first shoulder 380. First washer 372' may be placed against retainer 388. Retainer 388 is sized larger than the central opening in first washer 372'. After first washer 372' is positioned on second elongated member 370, dampener set 432 may be positioned on the second elongated member against the first washer. In some embodiments, the central passage of dampener set 432 is shaped so that the dampener set passes past first shoulder 380 of first elongated member 368. In other embodiments, dampener set 432 is forced past first shoulder 380 of first elongated member 368.

After dampener set 432 is positioned, second washer 372" may be placed on second elongated member 370 against the dampener set. In some embodiments, second washer 372" may be truncated or cut to accommodate spatial limitations due to offset member 308. In other embodiments, (e.g., for in-line embodiments of single dampener systems) truncated or cut second washers may not be required. Initially, slot 392 of second washer 372" is aligned with first shoulder 380 of first elongated member 368 to allow placement of the second washer on second elongated member 370. After slot 392 passes first shoulder 380, second washer 372" may be rotated so that the slot does not align with the first shoulder.

The end of second elongated member 370 may be positioned through opening 312 of offset member 308. End piece 434 may be threaded onto threading 390 of second elongated member 370. The outer surface of end piece 434 may be spherically contoured and the surface of offset member 308 that the outer surface contacts may also be spherically contoured. Slots 436 of end piece 434 extend through opening in offset member 308. Slots 436 of endpiece 434 may be oriented so that first shoulder 380 of first elongated member 368 align with the slots.

To insert the assembled dynamic posterior stabilization system in a patient, the patient is placed in a neutral position with substantially no flexion, extension, lateral bending or axial rotation. The first bone fastener is secured to the first vertebra of the vertebra to be stabilized. The second bone fastener is secured to the second vertebra of the vertebra to be stabilized. The ball of the dampener system is adjusted so that the ball fits in the collar of the first bone fastener and offset member fits on the second bone fastener with substantially no compression of dampener set. The ball may be positioned in the collar of the first bone fastener, and the sleeve may be positioned in the collar of the second bone fastener. Closure members may be secured to the collars of the first bone fastener and the second bone fastener.

Figure 69:
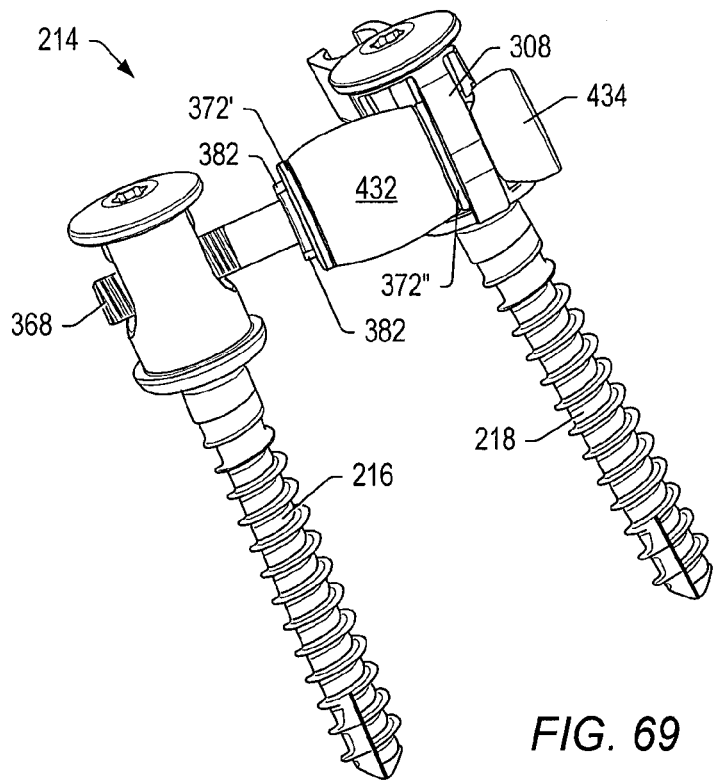

FIG. 69 depicts dynamic posterior stabilization system 214 compressed as if vertebrae coupled to first bone fastener 216 and second bone fastener 218 were subjected to extension and/or lateral bending towards the side that the dynamic posterior stabilization system is coupled to. In some embodiments, second washer 372" is positioned against offset member 308 and second shoulder 382 of first elongated member 368 contact first washer 372' and move the first washer towards second bone fastener 218 to compress dampener set 432. In some embodiments, an end of first elongated member 368 contacts the bottom of the slot in the second elongated member and pushes the second elongated member towards second bone fastener 218 such that end piece 434 moves away from offset member 308.

Figure 70:
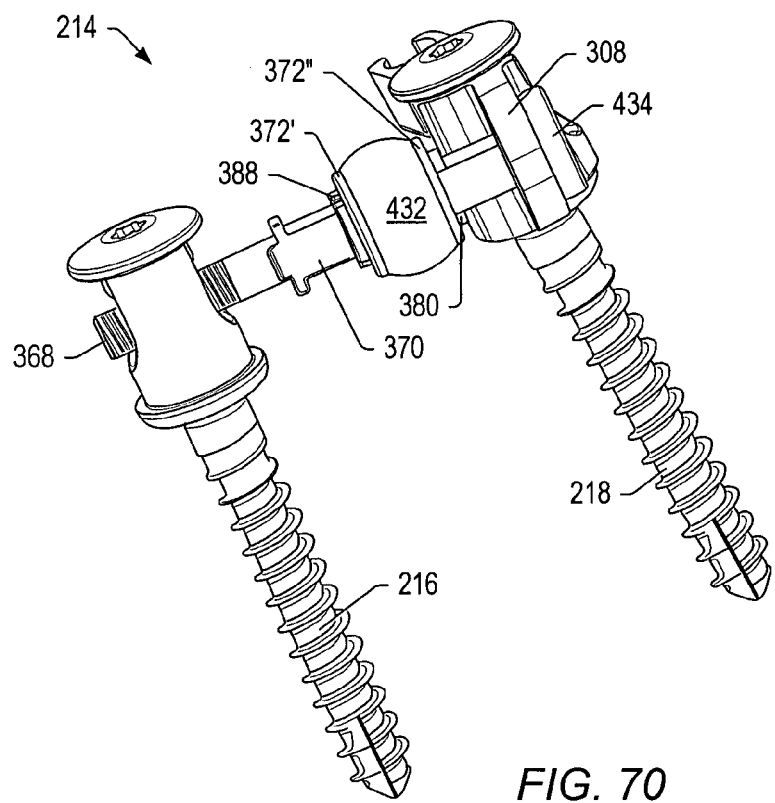

FIG. 70 depicts dynamic posterior stabilization system 214 extended as if vertebrae coupled to first bone fastener 216 and second bone fastener 218 were subjected to flexion and/or lateral bending away from the side the dynamic posterior stabilization system is coupled to. First elongated member 368 moves away from second elongated member 370. End piece 434 contacts offset member 308 and first shoulder 380 of first elongated member 368 contacts and draws second washer 372" towards retainers 388 to compress dampener set 432 between first washer 372' and second washer 372". Movement of first washer 372' is stopped by retainers 388.

For in-line dampener system embodiments, the end piece may be a sleeve that is coupled to the second elongated member. The second elongated member may include a stop (e.g., a flared end) that inhibits removal of the sleeve from the second elongated member. The sleeve allows a portion of the second elongated member to move through the collar when the first bone fastener moves closer to the second bone fastener. Movement of the second elongated member through the sleeve is resisted by compression of the dampener set. The stop allows the first elongated member to move away from the second elongated member when the first bone fastener moves away from the second bone fastener. Movement of the first elongated member away from the second elongated member is resisted by compression of the dampener set.

Figure 71:
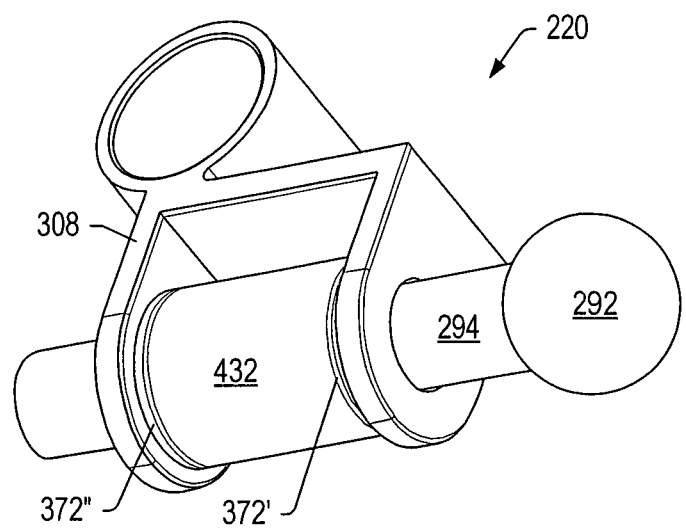
FIG. 71 depicts a perspective view of an embodiment of an offset, single dampener system with an external frame.

FIG. 71 depicts an embodiment of dampener system 220 in a neutral position. Dampener system 220 has a single dampener and an external frame. Dampener system 220 may include ball 292, elongated member 294, offset member 308, first washer 372', dampener set 432, and second washer 372". In some embodiments, the surfaces of washers 372 that contact dampener set 432 are curved (e.g., spherically contoured).

Figure 72:
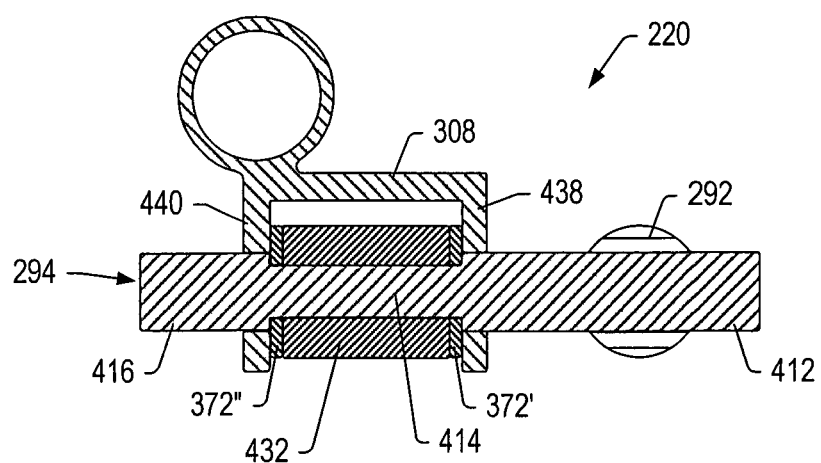
FIG. 72 depicts a cross-sectional representation of an embodiment of an offset, single dampener system with an external frame.

FIG. 72 depicts a cross-sectional representation of dampener system 220. Elongated member 294 may include first portion 412, second portion 414, and third portion 416. The diameter of second portion 414 is less than the diameter of first portion 412 and third portion 416. The diameter of first portion 412 is smaller than the diameter of the opening through first arm 438 of offset member 308. The diameter of first portion 412 is greater than a diameter of the opening through first washer 372' so that the first portion provides a stop for the first washer on elongated member 294. The diameter of the opening through first washer 372' is greater than the diameter of second portion 414. The length of second portion 414 may be substantially the same length as the sum of the lengths of first washer 372', dampener set 432 in a neutral position, and second washer 372". The diameter of third portion 416 is greater than a diameter of the opening through second washer 372" and less than a diameter of the opening through second arm 440 of offset member 308. The diameter of the opening through second washer 372" is greater than the diameter of second portion 414.

Ball 292 may be secured to a first bone fastener positioned in a first vertebra. Offset member 308 may be secured to a second bone fastener positioned in a second vertebra. The first bone fastener may move towards the second bone fastener when the vertebrae are subjected to extension and/or to lateral bending towards the side that dampener system 220 is coupled to. Compression of dampener set 432 provides resistance to such extension and/or lateral bending. First portion 412 of elongated member 294 engages first washer 372' and moves the first washer towards second washer 372". Dampener set 432 is compressed between first washer 372" and second washer 372". Third portion 416 of elongated member 294 slides outwards through second arm 440 of offset member 308.

The first bone fastener may move away from the second bone fastener when the vertebrae are subjected to flexion and/or to lateral bending away from the side that dampener system 220 is coupled to. Compression of dampener set 432 provides resistance to such flexion and/or lateral bending. When first bone fastener moves away from second bone fastener, third portion 416 of elongated member 294 engages second washer 372" and draws the second washer towards first washer 372' to compress dampener set 432 between the first washer and the second washer.

Figure 73:
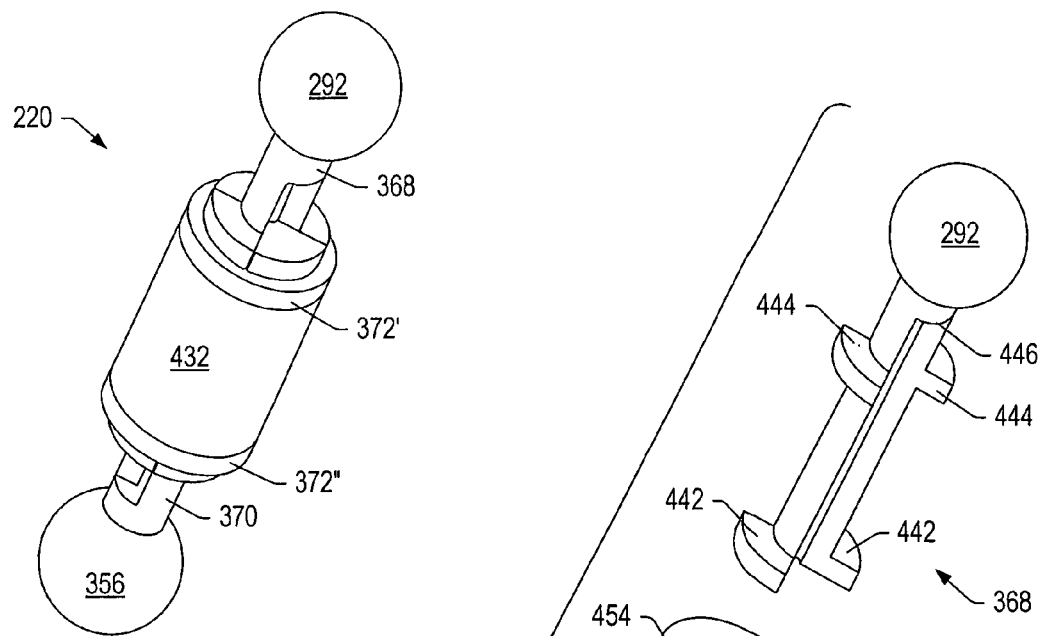
FIG. 73 depicts a perspective view of an embodiment of a single dampener system in a neutral position.

FIG. 73 depicts an embodiment of dampener system 220 in a neutral position. Dampener system 220 is an in-line, single dampener system with two elongated members. Dampener system 220 may include first elongated member 368, first ball 292, second elongated member 370, second ball 356, first washer first washer 372', dampener set 432, and second washer 372". First ball 292 may be placed on a threaded portion of first elongated member 368. First ball 292 may be rotated to adjust the length of dampener system 220. In other embodiments, second ball 356 or both balls may allow for adjustment of the length of the dampener system. In some embodiments, the surfaces of washers 372 that contact dampener set 432 are curved (e.g., spherically contoured).

Figure 74:
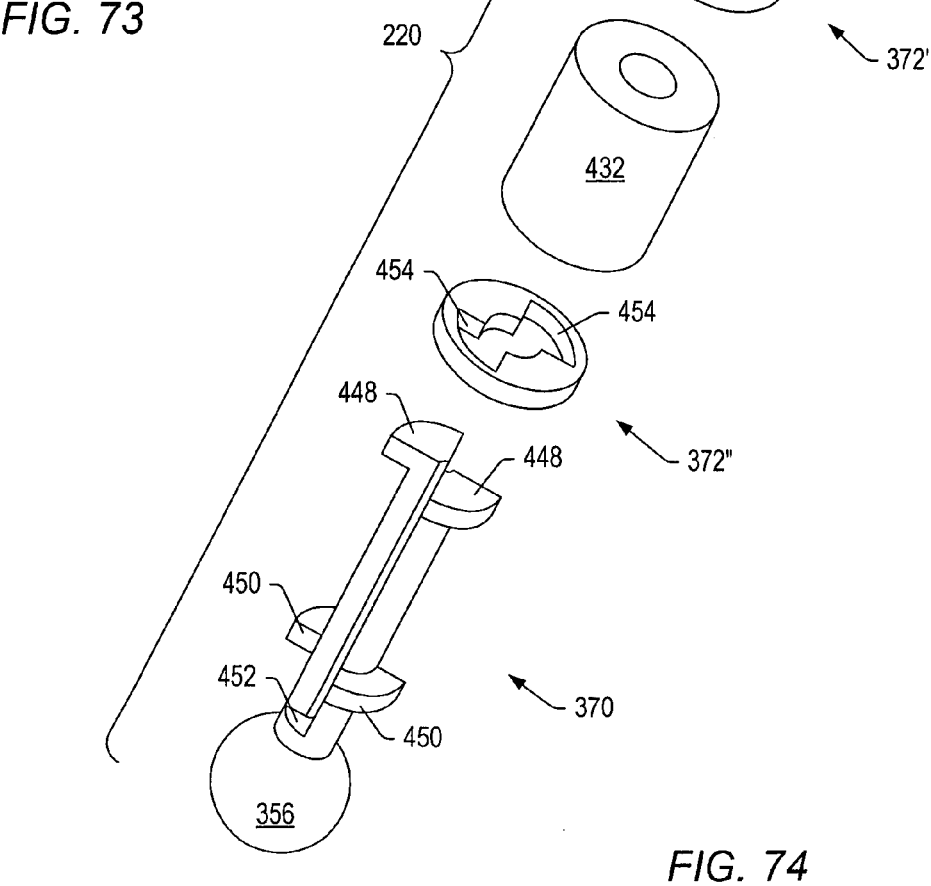
FIG. 74 depicts an exploded view of the single dampener system depicted in FIG. 73.

FIG. 74 depicts the components of single dampener system 220 depicted in FIG. 73. Elongated member 368 may include first shoulder 442, second shoulder 444, and stop 446. Second elongated member 370 may include first shoulder 448, second shoulder 450 and stop 452. Washers 372', 372" may include slots 454 that allow for passage of the shoulders of elongated members 368, 370.

First washer 372' may be oriented so that slots 454 allow the first washer to pass beyond first shoulder 442 of elongated member 368. First washer 372' may be moved past first shoulder 442, rotated 90°, and positioned against second shoulder 444. Dampener set 432 may be positioned on first elongated member 368 against first washer 372'. Second washer 372" may be placed on first elongated member 368 against dampener set 432 and the second washer may be rotated 90°. Second shaft 370 may be oriented so that first shoulder 448 passes through slots 454 of second washer 372" and first washer 372'. First shoulder 448 may be pushed through second washer 372", dampener set 432, and first washer 372'. When first shoulder 448 passes through first washer 372', the first washer and second washer 372" may be rotated (e.g., about 45°) so that removal of elongated members 368, 370 from the washers is inhibited.

Balls 292, 356 of assembled dampener system 220 shown in FIG. 73 may be secured to bone fasteners positioned in vertebrae. During extension and/or lateral bending towards the side of the vertebrae the dampener system is coupled to, the bone fasteners move closer together and compression of dampener set 432 provides resistance to the movement. Second shoulder 444 of first elongated member 368 moves first washer 372' towards second washer 372" and second shoulder 450 of second elongated member 370 moves the second washer towards the first washer to compress dampener set 432. In some embodiments, the range of motion of first elongated member 368 relative to second elongated member 370 is limited by contact of first shoulder 442 with stop 452. In some embodiments, the range of motion of second elongated member 370 relative to first elongated member 368 is limited by contact of first shoulder 448 with stop 446. In some embodiments, the range of motion of first elongated member 368 relative to second elongated member 370 is limited by the maximum amount of compression allowed by dampener set 432.

During flexion and/or lateral bending away from the side of the vertebrae the dampener system is coupled to, the bone fasteners move farther apart and compression of dampener set 432 provides resistance to the movement. First shoulder 442 of first elongated member 368 moves second washer 372" towards first washer 372', and first shoulder 448 of second elongated member 370 moves the second washer towards the first washer to compress dampener set 432.

Figure 75:
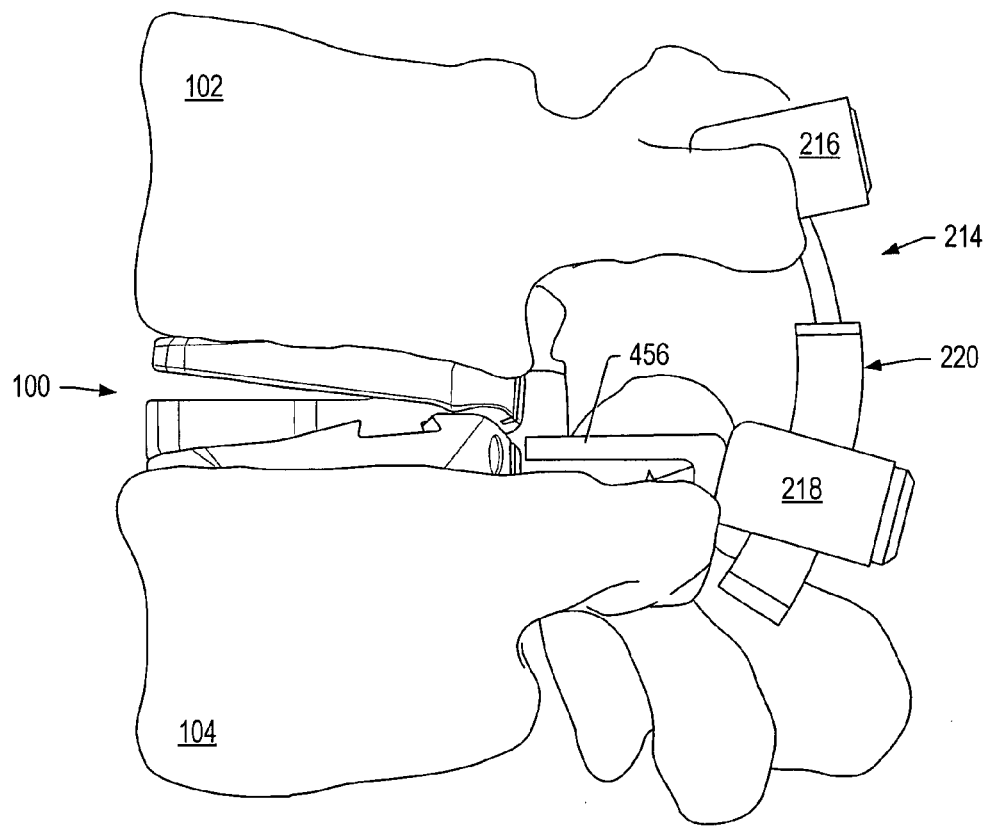
FIG. 75 depicts a representation of a dynamic interbody device and a posterior stabilization system coupled to vertebrae.

FIG. 75 depicts a representation of dynamic interbody device 100 and posterior stabilization system 214 positioned between vertebrae 102, 104. Bridge 456 may be coupled to second bone fastener 218 of dynamic posterior stabilization system 214. Bridge 456 may inhibit undesired migration of dynamic interbody device 100 relative to vertebrae 102, 104 while still allowing for flexion, extension, lateral bending, and/or axial rotation of the vertebrae.

In some embodiments, the center of curvature of the elongated member of dampener system 220 of dynamic posterior stabilization system 214 may align or substantially align with the center of curvature of dynamic interbody device 100 that allows for flexion/extension and/or lateral bending. Aligning or substantially aligning the center of curvature of the elongated member with the center or centers of curvature of dynamic interbody device 100 allows the elongated member to move relative to second bone fastener 218 during flexion/extension and/or lateral bending so that dynamic posterior stabilization system 214 works in conjunction with the dynamic interbody device. In some embodiments, the curvature of the elongated member of dampener system 220 of dynamic posterior stabilization system 214 may substantially follow the desired curvature of the spine.

Dynamic posterior stabilization system 214 may share a portion of the load applied to the vertebrae 102, 104 while providing guidance and resistance to flexion/extension and/or lateral bending that is, or is approximate to, the resistance provided by a normal functional spinal unit. Allowing for movement of the dynamic interbody device and for movement of the dynamic posterior stabilization system may inhibit deterioration of adjacent functional spinal units.

Bridge 456 may couple dynamic interbody device 100 to dynamic posterior stabilization system 214. Bridge 456 may be coupled to dynamic posterior stabilization system 214 at or near to second bone fastener 218. Coupling bridge 456 to dynamic posterior stabilization system 214 at or near to second bone fastener 218 may inhibit or eliminate contact of the bridge with neural structure exiting from between the vertebrae.

In some embodiments, a posterior approach may be used to install a stabilization system for a patient. The stabilization system may replace one or more parts of a functional spinal unit of the patient. The stabilization system may include one or more dynamic interbody devices, and one or more dynamic posterior stabilization systems.

Figure 76:
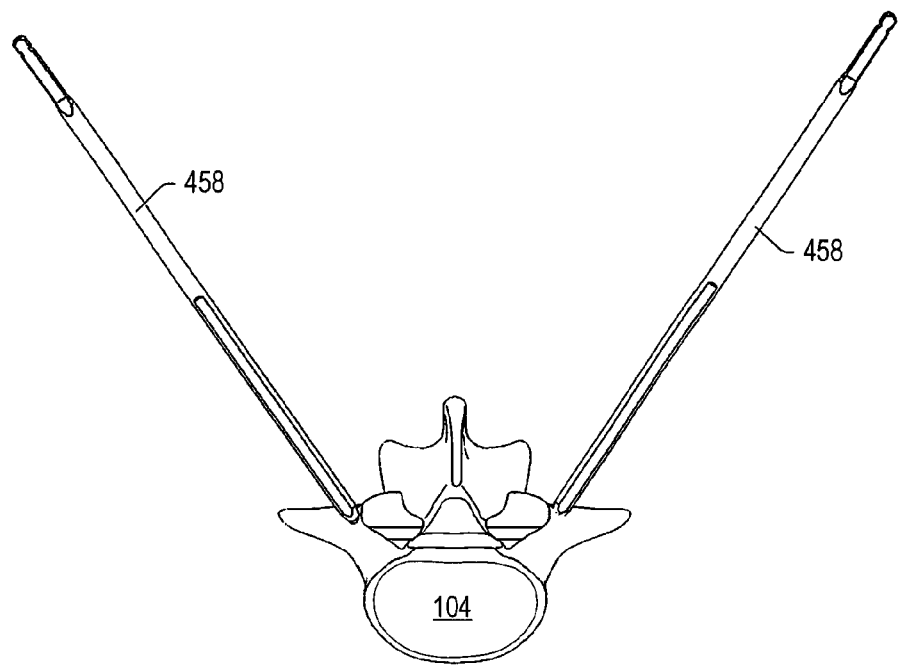
FIG. 76 depicts a representation of taps positioned in a lower vertebra during a spinal stabilization procedure.

During some posterior insertion procedures, the facet joints at the operative level may be removed (e.g., the superior facets from lower vertebra and the inferior facets from the upper vertebra). In some embodiments, the spinous process of the upper vertebra may also be removed. A bone awl may be used to mark each of the pedicles where the bone fasteners are to be positioned. A pedicle probe may be used to widen the initial holes made by the bone awl and set a desired trajectory. A tap may be attached to a handle and inserted into one of the pedicles. After insertion, the handle may be removed leaving the tap extending from the pedicle. The handle and the tap may have an AO connection or other type of low profile connection system. A tap may be inserted in each of the four pedicles. The taps may remain in the pedicles. Initially, the taps may be used to maintain distraction during a discectomy to provide disc space for the dynamic interbody devices. FIG. 76 depicts taps 458 positioned in lower vertebra 104, with the handle removed from the taps. Taps 458 may be positioned at any desired angle into lower vertebra 104 and the upper vertebra.

Figure 77:
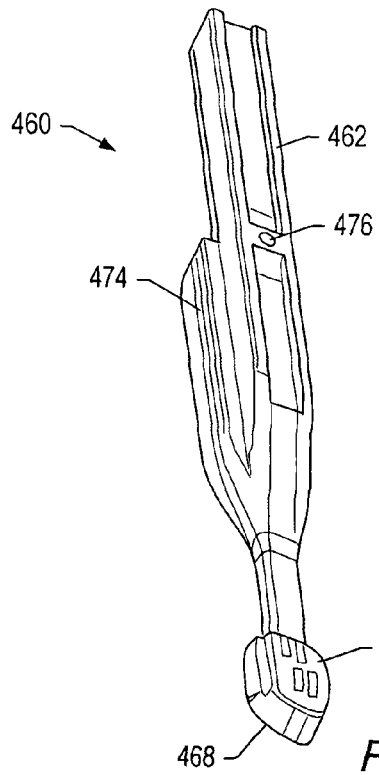
FIG. 77 depicts a perspective view of an embodiment of an expandable trial.
Figure 78:
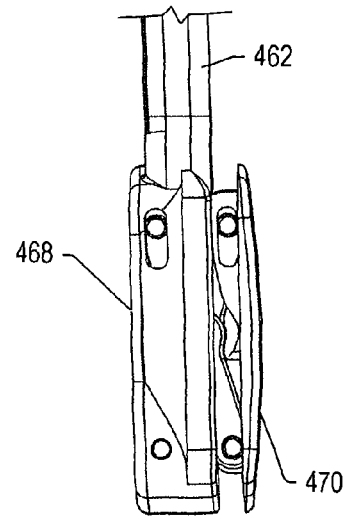
FIG. 78 depicts a perspective view of an end portion of the expandable trial with the movable plate lifted from the base plate.
Figure 79:
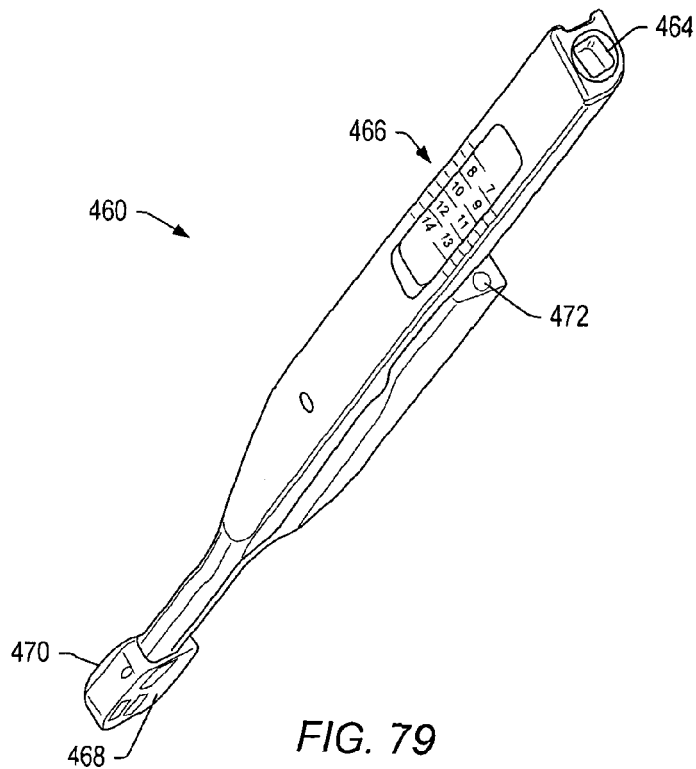
FIG. 79 depicts a perspective view of the expandable trial that emphasizes the top of the expandable trial.

After a discectomy, two expandable trials may be inserted in the disc space between the vertebrae. The expandable trial used on the left side of the patient may be a mirror image of the expandable trial used on the right side of the patient. FIGS. 77-79 depict an embodiment of expandable trial 460 that may be positioned on a first side of the vertebrae. Each expandable trial may include body 462, rotator 464, scale 466, base plate 468 and movable plate 470. Rotator 464 may be located at an end of body 462. Scale 466 may be located in an upper portion of body 462.

A rotatable handle may be coupled to rotator 464. When rotator 464 is turned, movable plate 470 moves in or out relative to base plate 468. FIG. 78 depicts movable plate 470 extended away from base plate 468. The amount of movement of movable plate 470 relative to base plate 468 may be indicated by the change in position of a movable portion of scale 466 relative to a stationary portion of the scale. The movable portion may include numbers and markings that indicate the height of a corresponding dynamic interbody device. The marking and corresponding number that aligns with a marking of the stationary portion of the scale indicates the current separation height of movable plate 470 relative to base plate 468.

A middle portion of body 462 may include passage 472, keyway 474, and guide recess 476. A drill or other type of cutter may be positioned through passage 472 to form a groove in the lower vertebra to accommodate a keel of the dynamic interbody device to be positioned in the disc space between the vertebrae. Keyway 474 may ensure that only the proper instrument guide can be used in association with the particular expandable trial. Guide recess 476 may accept an end of a guide release of the proper guide.

Base plate 468 may have an inferior surface with a shape that is substantially the same as the shape of the inferior surface of the dynamic interbody device to be positioned between the vertebrae without a keel. Base plate 468 may be positioned against the lower vertebra of the vertebrae being stabilized. Movable plate 470 may have a superior surface with a shape that is substantially the same as the shape of the superior surface of the dynamic interbody device to be positioned between the vertebrae. When the expandable trial is in an initial position, the movable plate and the base plate have a height that allows for insertion in the disc space between the vertebrae. After insertion, the rotator may be turned to separate the movable plate from the base plate to position the base plate against the lower vertebra and the movable plate against the upper vertebra.

The base plate and movable plate of the expandable trials may be positioned in the disc space between the vertebrae. An engaging end of a handle may be inserted in the rotator of a first expandable trial. The handle may be turned to cause the movable plate to move away from the base plate so that the movable plate and the base plate contact the vertebrae. The handle may be used to rotate the rotator of the second expandable trial so that the movable plate and the base plate of the second expandable trial contact the vertebrae. The separation height between the base plate and the movable plate is indicated by the scale of the expandable trial.

Figure 80:
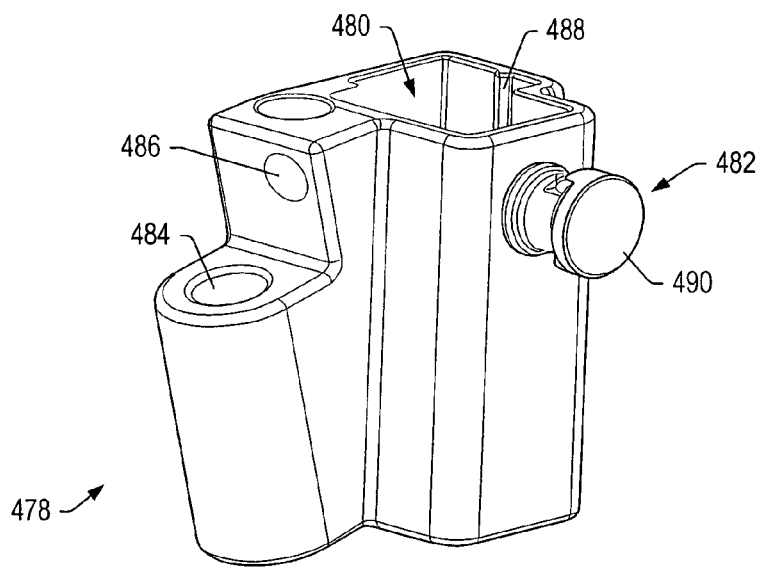
FIG. 80 depicts a perspective view of an embodiment of a guide.
Figures 81, 82:
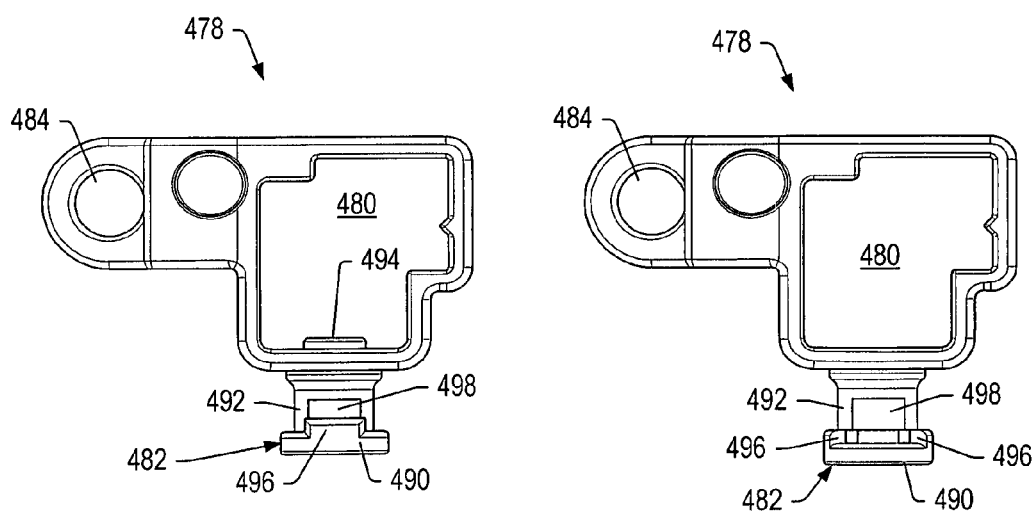
FIG. 81 depicts a top view of the guide with the guide release in a first position.
FIG. 82 depicts a top view of the guide with the guide release in a second position.

Guides may be coupled to each expandable trial. FIGS. 80-82 depict an embodiment of guide 478. Guide 478 may include passageway 480, guide release 482, passage 484, and recess 486. Passageway 480 may include key 488. Passageway 480 is shaped to fit over the body of the proper expandable trial. The key of the proper expandable trial fits in keyway 488. Passage 484 accepts posts of a bridge that couples the first expandable trial to the second expandable trial. Recess 486 accommodates a stabilizer of the bridge.

Guide release 482 may include grip 490, body 492, and end 494. When grip 490 is pulled outward from the guide 478, the grip may be rotated relative to body 492. In a first position (depicted in FIG. 81), end 494 of guide release extends into passageway 480. Arms 496 of grip 490 are next to flats 498 of body 492. A spring or other bias member in guide release 482 drives end 494 into passageway 480. In a second position (depicted in FIG. 82), end 494 does not extend into passageway 480. Grip 490 is pulled away from passageway 480 and rotated so that arms 496 of the grip reside on the top of body 492. The second position may be used to facilitate removal of an expandable trial or insertion instrument from guide 478.

A first guide may be placed over the appropriate expandable trial and lowered until the key of the guide is in the keyway of the expandable trial and the end of the guide release inhibits further movement of the guide. The grip may be pulled outwards to withdraw the end of the guide release from the passageway. The guide may be lowered and the grip may be released so that the spring in the guide release forces the end of the guide release against the body of the expandable trial. The guide may be lowered until the end of the guide release extends into the guide recess of the expandable trial. A second guide may be placed over the other expandable trial. Attaching the guides to the expandable trials after insertion of the base plates and movable plates between the vertebrae may allow more visibility of the position of the base plates and movable plates of the expandable trials during insertion. During some dynamic interbody device insertion procedures, the guide for the first expandable trial and/or the guide for the second expandable trial is placed on the appropriate expandable trial before the base plate and movable plate of the expandable trial is positioned between the vertebrae.

The position of the expandable trials may be adjusted so that the passages of the guides are oriented vertically. Also, an end of the base plate of the first expandable trial may touch or be close to touching an end of the base plate of the second expandable trial. In some embodiments, the base plates of the expandable trials may be coupled together with male and female portions when the base plates are positioned between the vertebrae.

Figure 83:
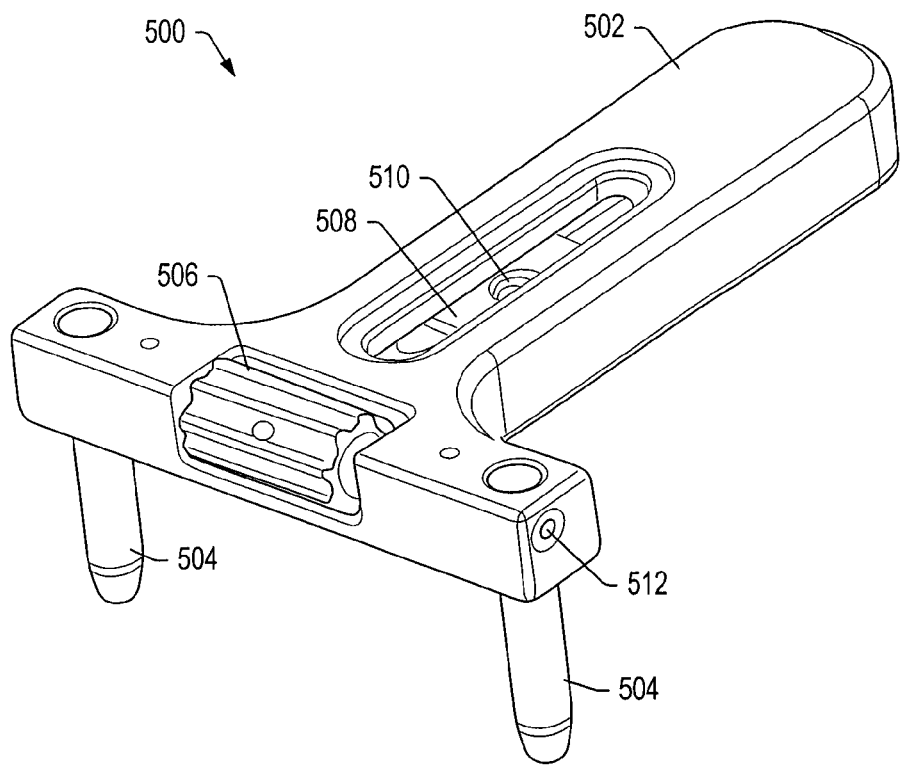
FIG. 83 depicts a perspective view of an embodiment of an insertion bridge.
Figure 84:
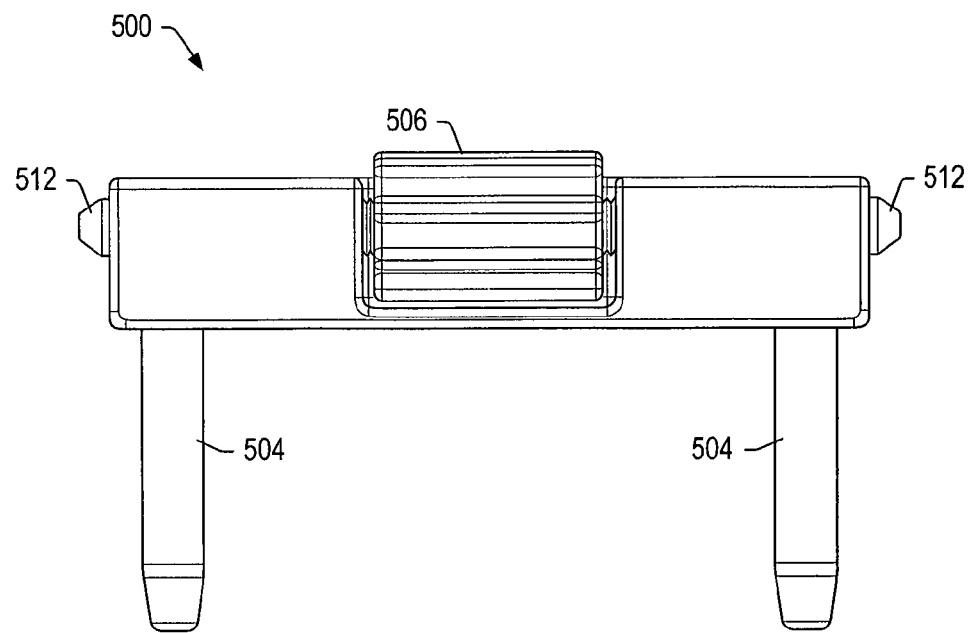
FIG. 84 depicts a front view of the insertion bridge.

Posts of the bridge may be inserted in the passages of the guides. FIG. 83 depicts an embodiment of insertion bridge 500. Insertion bridge 500 may include handle 502, posts 504, and wheel 506. Handle 502 facilitates positioning and moving insertion bridge 500. Handle 502 may include slide 508 with threaded opening 510. Slide 508 may move forward and backward in handle 502. Posts 504 may fit within passages of the guides. Wheel 506 may extend or retract stabilizers 512. Stabilizers 512 may extend from the body of insertion bridge 500 into the recesses of the guides. FIG. 84 depicts stabilizers 512 extended from the body of insertion bridge 500. When the stabilizers 512 are extended against the recesses of the guides, the outward force applied by the stabilizers to the guides generates torque applied by the guide to posts 504. The outward force and the torque couple the guides to insertion bridge 500 so that the guides remain coupled to the bridge when the expandable trials are removed from the guides.

Figure 85:
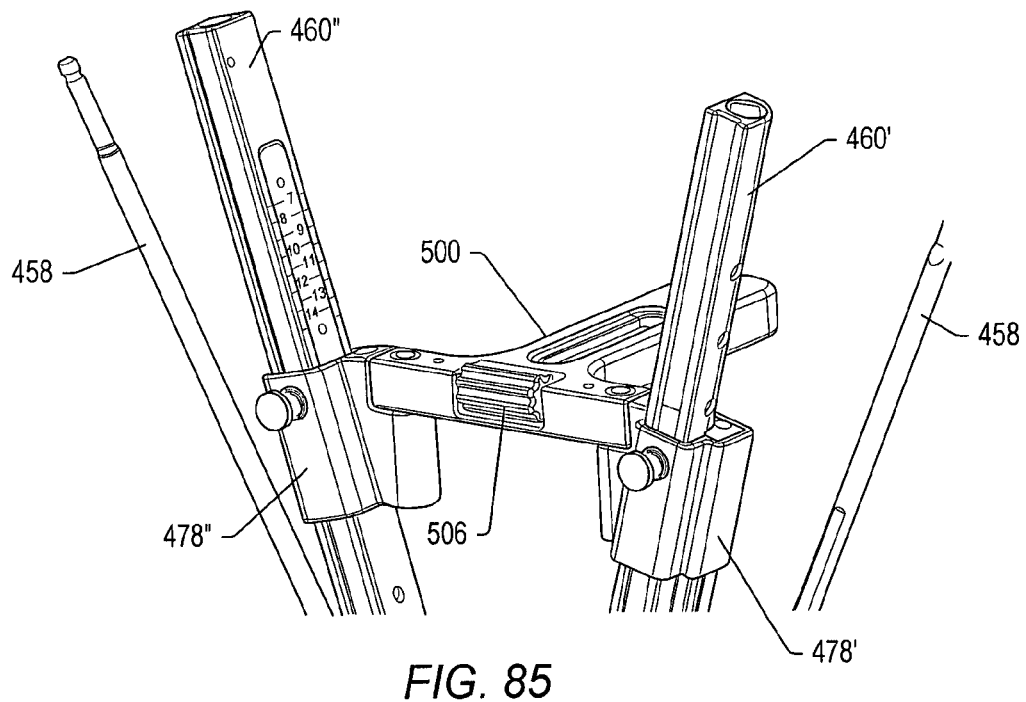
FIG. 85 depicts a perspective view of the insertion bridge coupled to guides and expandable trials.

FIG. 85 depicts insertion bridge 500 coupled to guides 478', 478". Wheel 506 has been turned to extend the stabilizers into the recesses of the guides and couple guides 478', 478" to insertion bridge 500.

Figure 86:
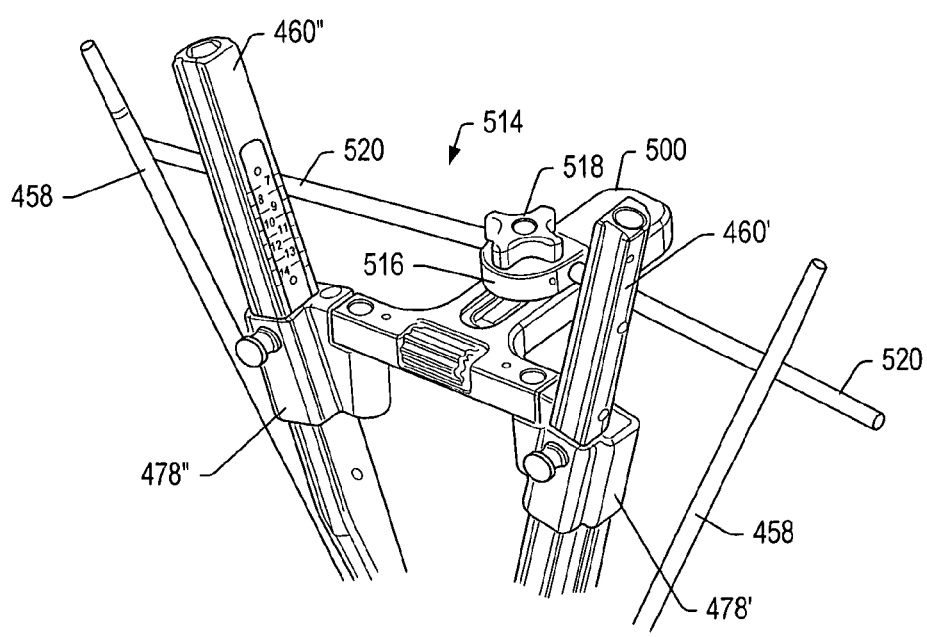
FIG. 86 depicts a perspective view of a bar assembly coupled to the insertion bridge, guides, and expandable trials.

A bar assembly may be coupled to the slide of the insertion bridge. FIG. 86 depicts bar assembly 514 coupled to insertion bridge 500. Bar assembly 514 may include base 516, knob 518, and rods 520. A shaft coupled to knob 518 may extend through base 516. A threaded end of the shaft may be threaded into the threaded opening in the slide of insertion bridge 500. Rods 520 may be coupled to the base 516. Rods 520 may be positioned near taps 458 by sliding the slide relative to handle 502 and/or by rotating rods 520 relative to the taps. When rods 520 are positioned near taps 458, knob 518 may be tightened against base 516 to inhibit movement of the slide relative to handle 502 and to inhibit rotation of the rods relative to the taps.

Figure 87:
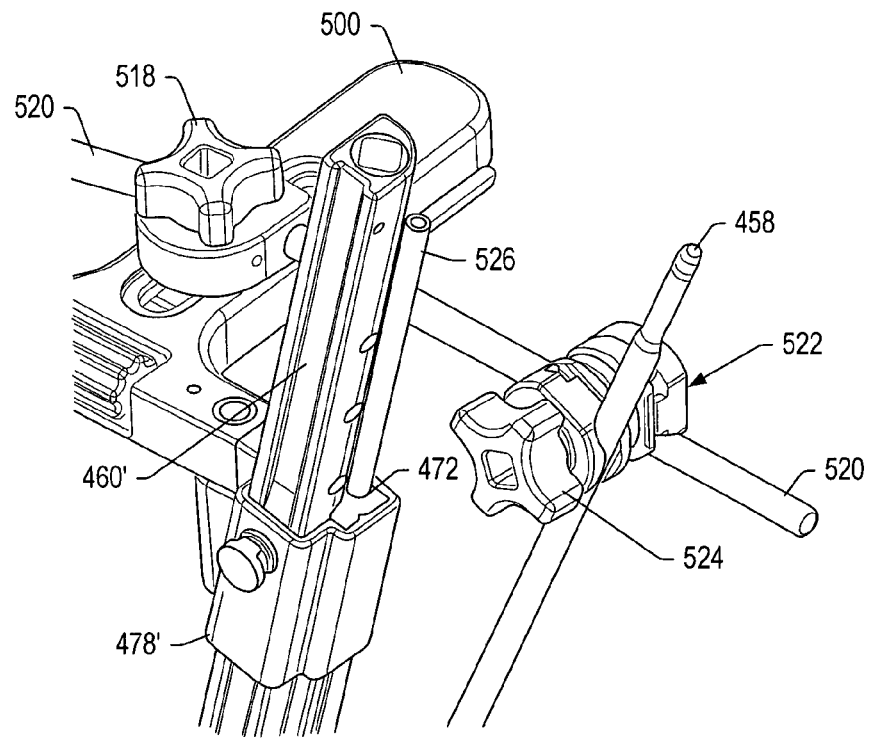
FIG. 87 depicts a perspective view of a rod connector attached to the tap and the rod of the bar assembly.

Rod connectors may be attached to the taps and to the rods of the bar assembly to anchor the insertion bridge to the spine. FIG. 87 depicts rod connector 522 attached to tap 458 and rod 520. When tap 458 and rod 520 are snapped into the openings of rod connector 522, knob 524 of the rod connector may be tightened to secure the taps and rods together. A second rod connector may be used to secure the second tap to the second rod.

Figure 88:
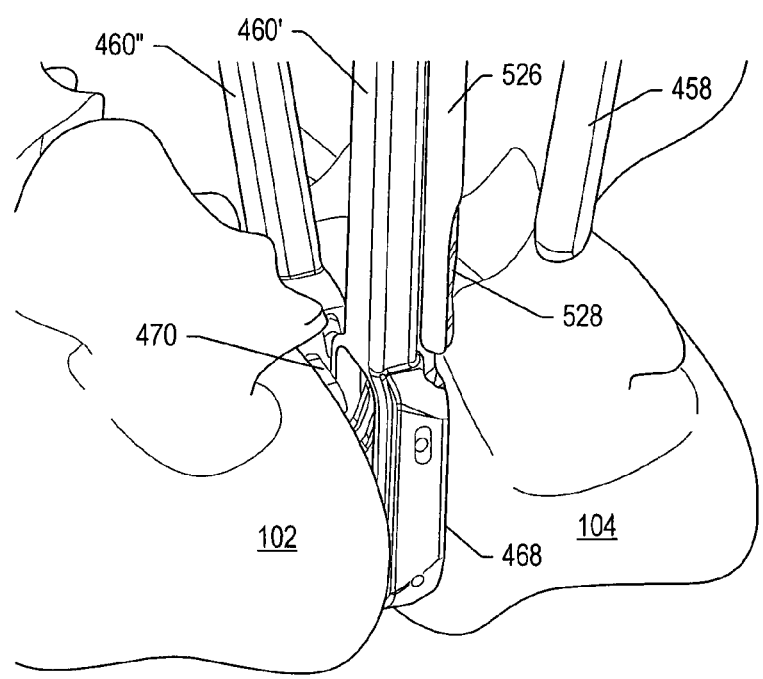
FIG. 88 depicts a perspective view of a keel guide and drill during formation of a keel opening in a vertebra.

The rotatable handle may be inserted into the rotators of the expandable trials and turned to set the expandable trials to the height of the dynamic interbody devices to be placed in the disc space. A keel guide may be inserted in the passage of the first expandable trial. FIG. 87 also depicts keel guide 526 positioned in passage 472 of expandable trial 460'. FIG. 88 depicts a distal portion of keel guide 526 with drill bit 528 forming a groove in lower vertebra 104. Base plate 468 of expandable trial includes a concave groove that accommodates drill bit 528. After the formation of the first keel groove, drill bit 528 and keel guide 526 may be removed from the first expandable trial. The keel guide may be placed in the passage of the second expandable trial. The drill bit may be used to form a second keel groove in the lower vertebra.

Figure 89:
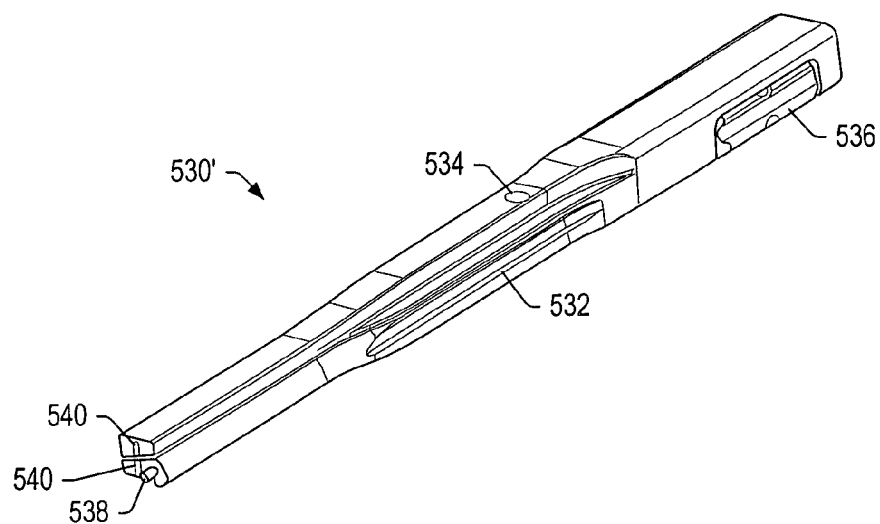
FIG. 89 depicts a perspective view of an embodiment of an insertion instrument.

The dynamic interbody devices to be inserted between the vertebrae may be attached to the appropriate insertion instruments. FIG. 89 depicts insertion instrument 530' for the first dynamic interbody device. The insertion instrument for the second dynamic interbody device may be a mirror image of the insertion instrument for the first dynamic interbody device. Insertion instrument 530 may include key 532, guide recess 534, wheel 536, shaft 538, and ridges 540. Key 532 and the shape of the body of insertion instrument 530 correspond to the shape of the passageway through the appropriate guide. Guide recess 534 accepts the end of the guide release of the guide to fix the position of insertion instrument 530 relative to the guide.

Wheel 536 may be rotated to rotate shaft 538. Rotating shaft 538 may advance or retract the shaft relative to the body of insertion instrument 530. The end of shaft 538 may be threaded. The threaded end may mate with the threaded opening in the appropriate dynamic interbody device. When shaft 538 is threaded to the appropriate dynamic interbody device, ridges 540 reside in the slots of the dynamic interbody device to place the dynamic interbody device in the desired position for insertion (i.e., neutral axial rotation, neutral lateral bending, and full flexion).

The rotation handle may be attached to the rotator of the first expandable trial. The rotator may be turned to decrease the separation height between the base plate and the movable plate of the expandable trial. The grip of the guide release may be pulled outwards, rotated and released so that the end of the guide release is withdrawn from the passageway of the guide. The first expandable trial may be removed from the guide. The first dynamic interbody device may be placed through the passageway and between the vertebrae. The grip of the guide release may be pulled outwards, rotated and released so that the spring of the guide release tries to force the end of the guide release into the passageway of the guide. The insertion instrument may be driven downwards until the end of the guide release snaps into the guide recess of the insertion instrument. If needed, a mallet or other impact instrument may be used against the insertion instrument to drive the dynamic interbody device between the vertebrae.

Figure 90:
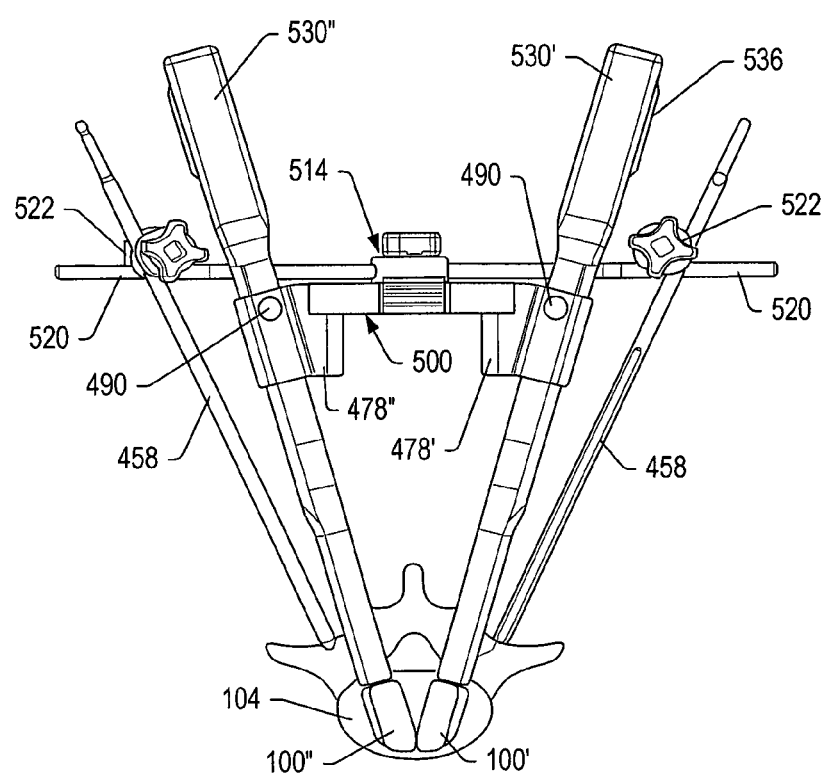
FIG. 90 depicts a perspective view of the lower vertebra with insertion instruments placing the dynamic interbody devices at a desired position.

The second expandable trial may be removed from the guide. The second dynamic interbody device may be inserted between the vertebrae. FIG. 90 depicts insertion instruments 530', 530" and dynamic interbody devices 100', 100" positioned against lower vertebrae 104. Imaging techniques may be used to determine that the dynamic interbody devices are properly interconnected and positioned in the disc space. When the dynamic interbody devices are properly interconnected and positioned, wheels 536 of insertion instruments 530', 530" may be rotated to disconnect the insertion instruments from dynamic interbody devices 100', 100". Grips 490 of guides 478', 478" may be pulled outwards to retract the ends of the guide releases from the passageways of the guides, and insertion instruments 530', 530" may be removed from the guides. Rod connectors 522 may be removed from taps 458 and bars 520. Insertion bridge 500, with bar assembly 514 and guides 478, may be removed.

Taps 458 may be removed from the vertebrae and bone fasteners of dynamic posterior stabilization systems may be inserted in the openings where the taps where positioned. A length of a dampener system of a first dynamic posterior stabilization system may be adjusted so that the dampener system can be coupled to the bone fasteners. The dampener system may be secured to the bone fasteners to form the first dynamic posterior stabilization system. A length of a dampener system of a second dynamic posterior stabilization system may be adjusted so that the dampener system can be coupled to the bone fasteners. The dampener system may be coupled to the bone fasteners to form the second dynamic posterior stabilization system. If needed, a cross link may be coupled to the first dynamic posterior stabilization system and the second dynamic posterior stabilization system.

In some embodiments, another technique may be used to insert dynamic interbody devices between vertebrae. An insertion structure may be formed before positioning an expandable trial or expandable trials between the vertebrae. Taps may be inserted in each of the pedicles. FIG. 76 depicts taps 458 positioned in lower vertebra 104, with the handle removed from the taps. Taps 458 may be positioned at any desired angle into lower vertebra 104 and the upper vertebra.

After a discectomy, one or more trials may be positioned in and removed from the disc space on a first side and a second side of the vertebrae. The trials may have the same length and width profile as the first member of the dynamic interbody device to be placed in the disc space or the same length and width profile as the third member of the dynamic interbody device to be placed in the disc space. The lengths and widths of the dynamic interbody devices to be placed in the disc space may be determined based on the trials.

Figure 91:
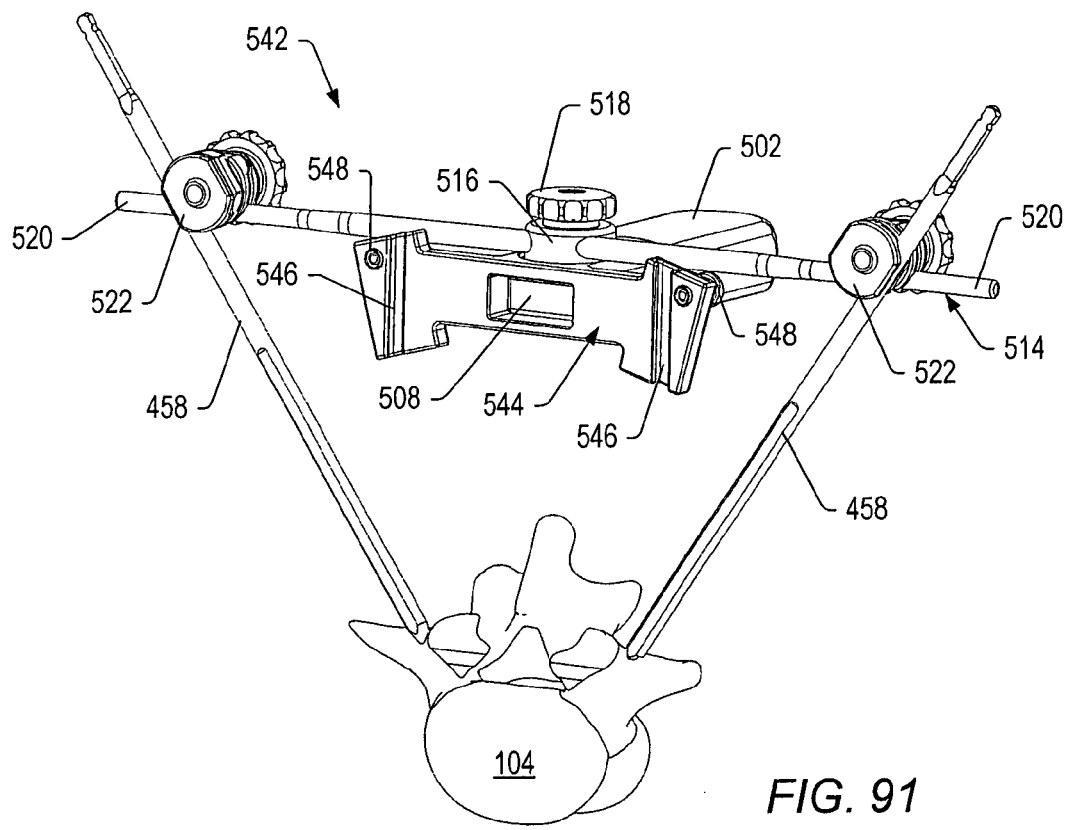
FIG. 91 depicts a perspective representation of an embodiment of a support frame coupled to taps positioned in the lower vertebra.

During some insertion procedures, the position of lower vertebra 104 is used as the basis for establishing the insertion angles for the dynamic interbody devices. A support frame may be coupled to taps 458. FIG. 91 depicts support frame 542 coupled to taps 458. Support frame 542 may include rod connectors 522, bar assembly 514, and bridge assembly 544. Bar assembly 514 may include a shaft with a threaded end, hub 516, knob 518, and rods 520. Rods 520 may be directly connected to hub 516 so that rotation of the rods independent of the hub is inhibited.

Rod connectors 522 may be used to couple bar assembly 514 to taps 458. Tap connectors 522 have sufficient freedom of movement to allow bar assembly 514 to be positioned at a desired height above the vertebrae with a horizontal orientation and with the vertical center line of the bridge assembly positioned substantially in line with the vertical center line of the end plate of lower vertebra 104. Hub 516 may be rotated in a recess in the handle of bridge assembly 544 to allow the front face of the bridge assembly to be oriented substantially parallel to the end plate of lower vertebra 104. Hub 516 may be moved forward or backward in the recess to adjust the offset distance of the front face of bridge assembly 544 from the end plate of lower vertebra 104.

Bridge assembly 544 may include handle 502, slide 508, guide slots 546, and guide releases 548. Handle 502 may be used to move bridge assembly 544. Slide 508 may be positioned in a hollow portion of handle 502. Hub 516 of bar assembly 514 may be positioned in a recess in handle 502. The threaded end of the shaft of bar assembly 514 may be threaded into a threaded opening of slide 508. When knob 518 of bar assembly 514 is loose, the bar assembly may be adjusted back and forth in the recess of handle to change the offset position of the front face of bridge assembly 544 relative to lower vertebra 104. Also, the orientation of the front face of bridge assembly 544 relative to the end plate of the lower vertebra may be changed by rotating handle 502 relative to hub 516. Knob 518 may be tightened to fix the position of bar assembly 514 relative to the handle 502. When bridge assembly 544 is properly positioned, the front face of the bridge assembly may be substantially parallel to the endplate of bottom vertebra 104, and guide slots 546 are substantially vertical and equidistant from the vertical centerline of lower vertebra 104.

Protrusions of instrument guides may be positioned in guide slots 546. Guide releases 548 may include a spring or other bias member that extends an end of the guide release beyond the front face of the bridge assembly. The end of the guide release may extend into an opening of an instrument guide to couple bridge assembly 544 to the instrument guide. A grip may be pulled away from bridge assembly 544 to retract the end of guide release 546 and allow the instrument guide to be removed from the bridge assembly.

A first guide and a second guide may be placed in guide slots 546 of bridge assembly 544. The first guide may be a mirror image of the second guide. When the guides are fully inserted in the guide slots of bridge assembly 544, guide releases 548 inhibit movement of the guides. During some procedures, guides are positioned in guide slots 546 before the support frame is coupled to the taps.

Figure 92:
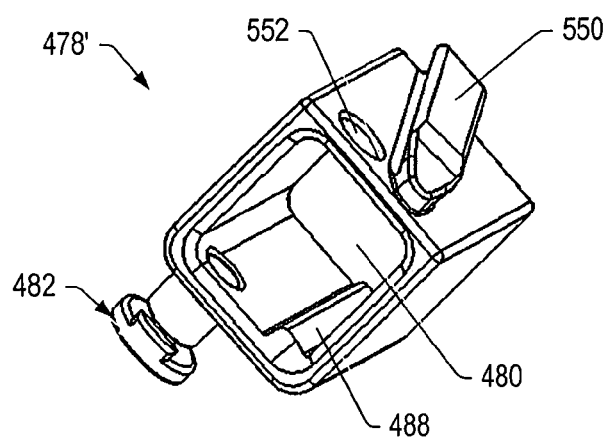
FIG. 92 depicts a perspective view of an embodiment of a first guide for a bridge assembly.

FIG. 92 depicts a perspective view of first instrument guide 478' used on a first side of the bridge assembly. First instrument guide 478' may include protrusion 550, opening 552, passageway 480, key 488, and guide release 482. Protrusion 550 may be placed in a guide slot guide slot of the bridge assembly. Protrusion 550 may be angled relative to passageway 480 so that the passageway is at a desired angle relative to vertical (and the lower vertebra) when the protrusion is positioned in the guide slot of the bridge assembly. In some embodiments, the angle of passageway 480 of the first guide 478' and the angle of the passageway of the second guide are directed inwards toward the vertical center line of the lower vertebra at about 15° relative to vertical. In some embodiments, the angle of passageway 480 of the first guide 478' and the angle of the passageway of the second guide are directed inwards toward the vertical center line of the lower vertebra at about 12° relative to vertical. When protrusion 550 is inserted in the guide slot of the bridge assembly, the end of the bridge assembly guide release extends into opening 552 to inhibit undesired movement of first guide 478'.

A trial or inserter may be placed through passageway 480 of first guide 478' that is positioned in the bridge assembly. Passageway 480 may include key 488. Key 488 may fit in a keyway of an appropriate trial or inserter used with the first guide 478'. When the appropriate trial or inserter is positioned in first guide 478', a spring or other bias member of guide release 482 may extend an end of the trial release into an opening in the trial or inserter to inhibit movement and allow a user to know that the trial or inserter is fully inserted.

Figure 93:
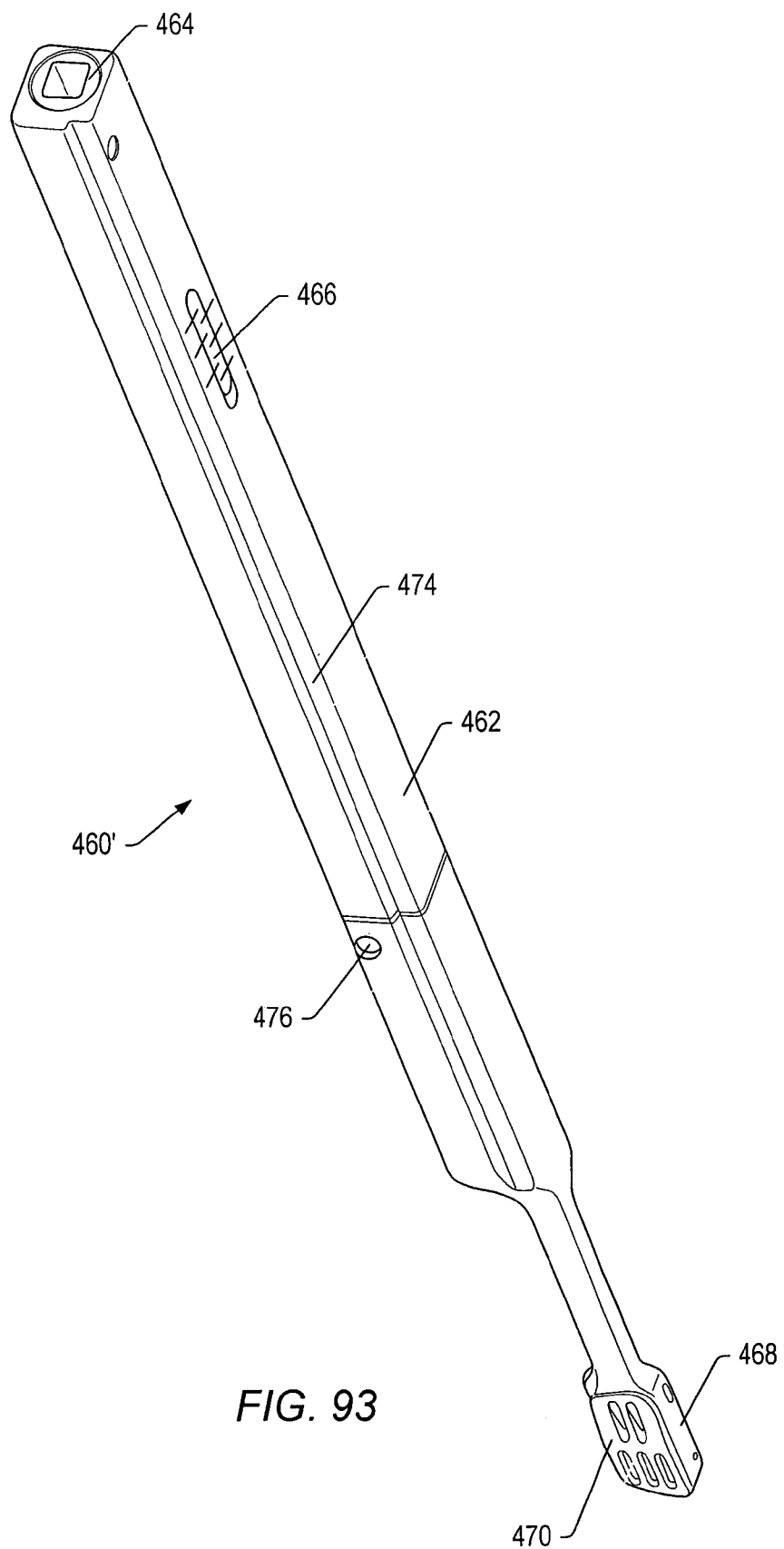
FIG. 93 depicts a perspective view of an embodiment of an expandable trial.

FIG. 93 depicts an embodiment of first expandable trial 460' that may be used to determine the appropriate height of a dynamic interbody device to be positioned between vertebrae. First expandable trial 460' may be used in conjunction with the first guide. A second expandable trial, which may be a mirror image of first expandable trial 460', may be used in conjunction with the second instrument guide. Expandable trial 460' may include body 462, keyway 474, guide recess 476, rotator 464, scale 466, base plate 468 and movable plate 470. Keyway 474 may extend along a portion of body 462. When expandable trial 460' is inserted into the first guide, the key of the guide is positioned in keyway 474. Keyway 474 only allows the use of expandable trial 460' with the appropriate guide. When expandable trial 460' is fully inserted in the first guide, an end of the guide release of the guide may extend into guide opening 476 to inhibit further insertion of the expandable trial.

Rotator 464 may be located near a first end of expandable trial 460'. A tool may be positioned in rotator 464. Turning the tool may advance a shaft in the upper part of body 462. Torque needed to turn the tool and advance the shaft may be offset by counter-torque applied to the handle of the bridge assembly. The amount of advancement of the shaft may be indicated on scale 466. Scale 466 may indicate height corresponding to height between the upper portion of movable plate 470 and the lower portion of base plate 468.

Turning rotator 464 extends the shaft against an actuator located in the lower part of body 462. The actuator may engage a linkage mechanism coupled to base plate 468 and movable plate 470. The actuator may push and move a linkage pin. The linkage pin is coupled to lifting arms. When the linkage pin is moved, the linkage arms raise movable plate 470 from base plate 468. FIG. 78 depicts an end portion of expandable trial with movable plate 470 lifted above base plate 468.

Before insertion through passages of the guides, the movable plates of the expandable trials may be adjusted relative to the base plates so that the movable plates and base plates can be inserted into the disc space between the vertebrae. The expandable trials may be inserted in the appropriate insertion guides so that the movable plates and base plates of the expandable trials extend into the disc space between the vertebrae. The base plates may be abutted against the end plate of the lower vertebra by loosening the knob of the bridge assembly and moving the base plates against the lower vertebra. The knob may be tightened to inhibit additional movement of the expandable trials relative to the lower vertebrae.

Figure 94:
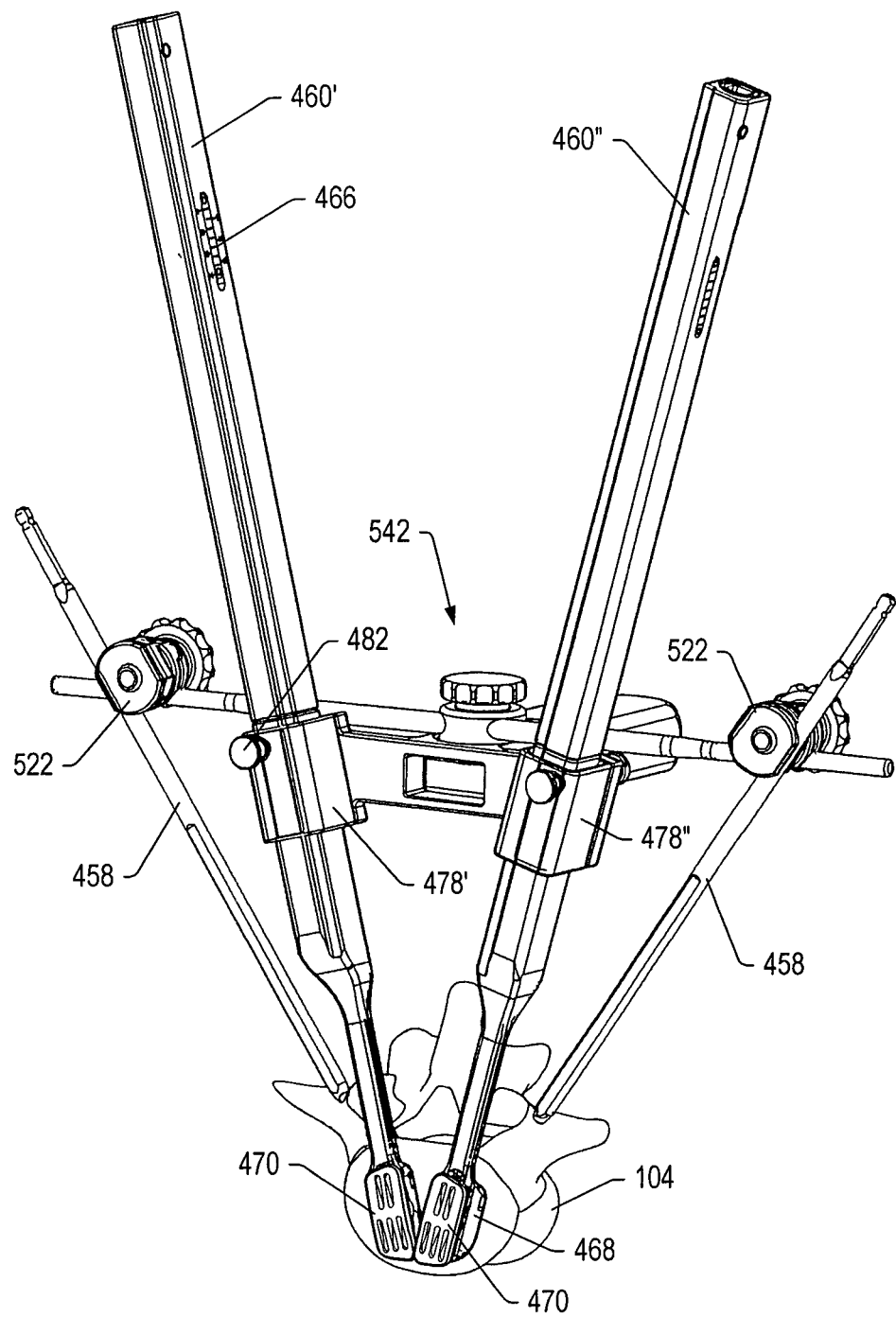
FIG. 94 depicts a representation of expandable trials positioned against the lower vertebra during the dynamic interbody device insertion procedure.

FIG. 94 depicts expandable trials 460', 460" positioned in guides 478', 478". The rotators of expandable trials 460', 460" may be turned in a first direction to lift movable plates 470 above the base plates 468. The tool used to turn the rotators may include a torque gauge. The rotators may be turned until a desired amount of torque is applied. When the desired amount of torque is applied, the height indicated on scales 466 of expandable trials may correspond to the heights of dynamic interbody devices to be implanted between the vertebrae.

The appropriate dynamic interbody devices may be selected from the instrument kit. Each dynamic interbody device may be coupled to an appropriate inserter. The rotator of first expandable trial 460' may be turned in the direction opposite to the direction that lifts movable plate 470 from base plate 468. The grip of guide release 482 of first guide 478' may be pulled and expandable trial 460' may be removed from the first guide. The vertebrae may be prepared to receive the first dynamic interbody device. For example, a channel may be formed in a vertebra to accept a keel of the dynamic interbody device. The first dynamic interbody device may be inserted through first guide 478' and into the disc space. The same procedure may be followed to insert the second dynamic interbody device into the disc space.

The portions of the inserters that fit in the inserter openings of the dynamic interbody devices may be retracted from the inserter openings. The portions of the inserter that reside in the curved slots of the second members and third members of the dynamic interbody devices may be rotated to remove the portions from the curved slots. The inserters may be removed from the guides 478', 478". Tap connectors 522 may be released and removed from taps 458. Support frame 542 and instrument guides 478', 478" may be removed from the patient.

Taps 458 may be removed from the vertebrae and bone fasteners of dynamic posterior stabilization systems may be inserted in the openings where the taps where positioned. A length of a dampener system of a first dynamic posterior stabilization system may be adjusted so that the dampener system can be coupled to the bone fasteners. The dampener system may be secured to the bone fasteners to form the first dynamic posterior stabilization system. A length of a dampener system of a second dynamic posterior stabilization system may be adjusted so that the dampener system can be coupled to the bone fasteners. The dampener system may be coupled to the bone fasteners to form the second dynamic posterior stabilization system. If needed, a cross link may be coupled to the first dynamic posterior stabilization system and the second dynamic posterior stabilization system.

In this patent, certain U.S. patents, and U.S. patent applications have been incorporated by reference. The text of such U.S. patents and U.S. patent applications is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A dynamic stabilization system, comprising:
 a first bone fastener configured to couple to a first vertebra;
 a second bone fastener configured to couple to a second vertebra;
 a dampener system comprising:
   a first elastic dampener member; and
   a second elastic dampener member,
 wherein movement of the first bone fastener towards the second bone fastener is configured to result in compression of the first elastic dampener member to resist movement of the first bone fastener toward the second bone fastener and is not configured to result in compression of the second elastic dampener member, and
 wherein movement of the first bone fastener away from the second bone fastener is configured to result in compression of the first elastic dampener member and compression of the second elastic dampener member to resist movement of the first bone fastener away from the second bone fastener,
 such that the first dampener member provides resistance to movement of the first bone fastener towards and away from the second bone fastener during use and the second dampener member provides resistance to movement of the first bone fastener away from the second bone fastener and does not provide substantial resistance to movement of the first bone fastener towards the second bone fastener during use.

2. The dynamic stabilization system of claim 1, wherein the first elastic dampener is concentrically positioned relative to the second elastic dampener member.

3. The dynamic stabilization system of claim 1, further comprising at least one dynamic interbody device configured to be positioned between the first vertebra and the second vertebra.

4. The dynamic stabilization system of claim 1, wherein each of the first and second elastic dampener members comprises a first rigid member configured to be disposed on a first side of the elastic dampener member and a second rigid member configured to be disposed on a second side of the elastic dampener member that is opposite from the first side during use such that the first and second rigid members sandwich the respective elastic dampener members.

5. A dynamic stabilization system, comprising:
a first bone fastener configured to couple to a first vertebra;
a second bone fastener configured to couple to a second vertebra; and
a dampener system comprising:
a first portion configured to couple to the first bone fastener;
a first dampener set;
a second dampener set; and
a second portion configured to couple to the second bone fastener,
wherein compression of the first dampener set is configured to provide resistance to movement of the first bone fastener towards the second bone fastener during use,
wherein compression of the first dampener set is configured to provide resistance to movement of first bone fastener away from the second bone fastener during use,
wherein compression of the second dampener set is configured to provide resistance to movement of first bone fastener away from the second bone fastener during use, and
wherein the dampener system comprises an elongated member, wherein the elongated member comprises the first portion and the second portion, and wherein the first portion is configured to move relative to the second portion.

6. The dynamic stabilization system of claim 5, wherein the first dampener set comprises an elastic dampener member and wherein the second dampener set comprises an elastic dampener member.

7. The dynamic stabilization system of claim 6, wherein each of the first and second dampener sets comprises a first rigid member configured to be disposed on a first side of the elastic dampener member and a second rigid member configured to be disposed on a second side of the elastic dampener member that is opposite from the first side during use such that the first and second rigid members sandwich the respective elastic dampener members.

8. The dynamic stabilization system of claim 7, wherein movement of the first bone fastener towards the second bone fastener is configured to result in movement of the first and second rigid members of the first dampener set to toward one another to compress the elastic dampener of the first dampener set during use, and wherein movement of the first bone fastener away from the second bone fastener is configured to result in movement of the first and second rigid members of the first dampener set toward one another and movement of the first and second rigid members of the second dampener set toward one another to compress the respective elastic dampeners of the first and second dampener sets during use.

9. The dynamic stabilization system of claim 5, wherein the first dampener set comprises a plurality of dampeners.

10. The dynamic stabilization system of claim 5, wherein the first dampener set comprises a first dampener concentrically positioned relative to a second dampener.

11. The dynamic stabilization system of claim 5, wherein the first dampener set comprises a dampener with large and small diameter sections.

12. The dynamic stabilization system of claim 5, further comprising at least one dynamic interbody device configured to be positioned between the first vertebra and the second vertebra.

13. A dynamic stabilization system, comprising:
a first bone fastener configured to couple to a first vertebra;
a second bone fastener configured to couple to a second vertebra; and
a dampener system comprising:
a first portion configured to couple to the first bone fastener;
a first dampener set;
a second dampener set;
a second portion configured to couple to the second bone fastener; and
a sleeve configured to couple the second portion to the second bone fastener;
wherein compression of the first dampener set is configured to provide resistance to movement of the first bone fastener towards the second bone fastener during use,
wherein compression of the first dampener set is configured to provide resistance to movement of first bone fastener away from the second bone fastener during use, and
wherein compression of the second dampener set is configured to provide resistance to movement of first bone fastener away from the second bone fastener during use.

14. A dynamic stabilization system, comprising:
a first bone fastener configured to couple to a first vertebra;
a second bone fastener configured to couple to a second vertebra; and
a dampener system comprising:
a first portion configured to couple to the first bone fastener;
a first dampener set;
a second dampener set;
a second portion configured to couple to the second bone fastener; and
an offset member configured to couple the second portion to the second bone fastener;
wherein compression of the first dampener set is configured to provide resistance to movement of the first bone fastener towards the second bone fastener during use,
wherein compression of the first dampener set is configured to provide resistance to movement of first bone fastener away from the second bone fastener during use, and
wherein compression of the second dampener set is configured to provide resistance to movement of first bone fastener away from the second bone fastener during use.

15. A dynamic stabilization system, comprising:
a first bone fastener configured to couple to a first vertebra;
a second bone fastener configured to couple to a second vertebra;
a first washer having a convex surface;
a second washer having a convex surface, wherein the convex surface of the first washer and the convex surface of the second washer are configured to engage recesses in a collar of the second bone fastener; and
a dampener system comprising:
a first portion configured to couple to the first bone fastener;
a first dampener set;
a second dampener set; and
a second portion configured to couple to the second bone fastener;
wherein compression of the first dampener set is configured to provide resistance to movement of the first bone fastener towards the second bone fastener during use, wherein compression of the first dampener set is configured to provide resistance to movement of first bone fastener away from the second bone fastener during use, and wherein compression of the second dampener set is configured to provide resistance to movement of first bone fastener away from the second bone fastener during use.

16. A dynamic stabilization system, comprising:
a first bone fastener configured to couple to a first vertebra;
a second bone fastener configured to couple to a second vertebra; and
a dampener system, comprising:
   a variable length elongated member configured to couple to the first bone fastener and the second bone fastener;
   a first dampener set coupled to the variable length elongated member on a first side of the member;
   a second dampener set coupled to the variable length elongated member on a second side of the member; and
   a sleeve configured to couple the variable elongated member to the second bone fastener,
wherein the first dampener set is configured to compress to provide resistance to movement of the first bone fastener towards the second bone fastener during use,
wherein the first dampener set is configured to compress to provide resistance to movement of the first bone fastener away from the second bone fastener during use, and
wherein the second dampener set is configured to compress to provide resistance to movement of the first bone fastener away from the second bone fastener during use.

17. A dynamic stabilization system, comprising:
a first bone fastener configured to couple to a first vertebra;
a second bone fastener configured to couple to a second vertebra; and
a dampener system, comprising:
   a variable length elongated member configured to couple to the first bone fastener and the second bone fastener;
   a first dampener set coupled to the variable length elongated member on a first side of the member;
   a second dampener set coupled to the variable length elongated member on a second side of the member; and
   an offset member configured to couple the variable elongated member to the second bone fastener,
wherein the first dampener set is configured to compress to provide resistance to movement of the first bone fastener towards the second bone fastener during use,
wherein the first dampener set is configured to compress to provide resistance to movement of the first bone fastener away from the second bone fastener during use, and
wherein the second dampener set is configured to compress to provide resistance to movement of the first bone fastener away from the second bone fastener during use.

18. A dynamic stabilization system, comprising:
a first bone fastener configured to couple to a first vertebra;
a second bone fastener configured to couple to a second vertebra;
at least one washer having a convex surface configured to engage a recess in a collar of the second bone fastener; and
a dampener system, comprising:
   a variable length elongated member configured to couple to the first bone fastener and the second bone fastener;
   a first dampener set coupled to the variable length elongated member on a first side of the member; and
   a second dampener set coupled to the variable length elongated member on a second side of the member;
wherein the first dampener set is configured to compress to provide resistance to movement of the first bone fastener towards the second bone fastener during use,
wherein the first dampener set is configured to compress to provide resistance to movement of the first bone fastener away from the second bone fastener during use, and
wherein the second dampener set is configured to compress to provide resistance to movement of the first bone fastener away from the second bone fastener during use.

19. A dynamic stabilization system, comprising:
a first bone fastener configured to couple to a first vertebra;
a second bone fastener configured to couple to a second vertebra; and
a dampener system comprising:
   a first portion configured to couple to the first bone fastener;
   a first dampener set;
   a second dampener set; and
   a second portion configured to couple to the second bone fastener,
wherein the first dampener set is configured to be disposed between a head portion of the first bone fastener and a head portion of the second bone fastener during use, and wherein the second dampener set is configured to be disposed on an opposite side of the head portion of the second bone fastener from the first dampener set during use,
wherein compression of the first dampener set is configured to provide resistance to movement of the first bone fastener towards the second bone fastener during use,
wherein compression of the first dampener set is configured to provide resistance to movement of first bone fastener away from the second bone fastener during use, and
wherein compression of the second dampener set is configured to provide resistance to movement of first bone fastener away from the second bone fastener during use.

20. The dynamic stabilization system of claim 19, wherein the first dampener set comprises an elastic dampener member and wherein the second dampener set comprises an elastic dampener member.

21. The dynamic stabilization system of claim 20, wherein each of the first and second dampener sets comprises a first rigid member configured to be disposed on a first side of the elastic dampener member and a second rigid member configured to be disposed on a second side of the elastic dampener member that is opposite from the first side during use such that the first and second rigid members sandwich the respective elastic dampener members.

22. The dynamic stabilization system of claim 21, wherein movement of the first bone fastener towards the second bone fastener is configured to result in movement of the first and second rigid members of the first dampener set to toward one another to compress the elastic dampener of the first dampener set during use, and wherein movement of the first bone fastener away from the second bone fastener is configured to result in movement of the first and second rigid members of the first dampener set toward one another and movement of the first and second rigid members of the second dampener set toward one another to compress the respective elastic dampeners of the first and second dampener sets during use.

23. The dynamic stabilization system of claim 19, wherein the first dampener set comprises a plurality of dampeners.

24. The dynamic stabilization system of claim 19, wherein the first dampener set comprises a first dampener concentrically positioned relative to a second dampener.

25. The dynamic stabilization system of claim 19, wherein the first dampener set comprises a dampener with large and small diameter sections.

26. The dynamic stabilization system of claim 19, further comprising at least one dynamic interbody device configured to be positioned between the first vertebra and the second vertebra.

27. A dynamic stabilization system, comprising:
a first bone fastener configured to couple to a first vertebra;
a second bone fastener configured to couple to a second vertebra; and
a dampener system comprising:
  a first portion configured to couple to the first bone fastener;
  a first dampener set;
  a second dampener set; and
  a second portion configured to couple to the second bone fastener,
wherein movement of the first bone fastener towards the second bone fastener is configured to result in compression of the first dampener set and is not configured to result in compression of the second dampener set during use, and
wherein movement of the first bone fastener away from the second bone fastener is configured to result in compression of the first dampener set and compression of the second dampener set during use,
wherein compression of the first dampener set is configured to provide resistance to movement of the first bone fastener towards the second bone fastener during use,
wherein compression of the first dampener set is configured to provide resistance to movement of first bone fastener away from the second bone fastener during use, and
wherein compression of the second dampener set is configured to provide resistance to movement of first bone fastener away from the second bone fastener during use.

28. The dynamic stabilization system of claim 27, wherein the first dampener set comprises an elastic dampener member and wherein the second dampener set comprises an elastic dampener member.

29. The dynamic stabilization system of claim 28, wherein each of the first and second dampener sets comprises a first rigid member configured to be disposed on a first side of the elastic dampener member and a second rigid member configured to be disposed on a second side of the elastic dampener member that is opposite from the first side during use such that the first and second rigid members sandwich the respective elastic dampener members.

30. The dynamic stabilization system of claim 29, wherein movement of the first bone fastener towards the second bone fastener is configured to result in movement of the first and second rigid members of the first dampener set to toward one another to compress the elastic dampener of the first dampener set during use, and wherein movement of the first bone fastener away from the second bone fastener is configured to result in movement of the first and second rigid members of the first dampener set toward one another and movement of the first and second rigid members of the second dampener set toward one another to compress the respective elastic dampeners of the first and second dampener sets during use.

31. The dynamic stabilization system of claim 27, wherein the first dampener set comprises a plurality of dampeners.

32. The dynamic stabilization system of claim 27, wherein the first dampener set comprises a first dampener concentrically positioned relative to a second dampener.

33. The dynamic stabilization system of claim 27, wherein the first dampener set comprises a dampener with large and small diameter sections.

34. The dynamic stabilization system of claim 27, further comprising at least one dynamic interbody device configured to be positioned between the first vertebra and the second vertebra.

35. A dynamic stabilization system, comprising:
a first bone fastener configured to couple to a first vertebra;
a second bone fastener configured to couple to a second vertebra; and
a dampener system, comprising:
  a variable length elongated member configured to couple to the first bone fastener and the second bone fastener;
  a first dampener set coupled to the variable length elongated member on a first side of the member; and
  a second dampener set coupled to the variable length elongated member on a second side of the member,
wherein the first dampener set is configured to be disposed between a head portion of the first bone fastener and a head portion of the second bone fastener during use, and wherein the second dampener set is configured to be disposed on an opposite side of the head portion of the second bone fastener from the first dampener set during use,
wherein the first dampener set is configured to compress to provide resistance to movement of the first bone fastener towards the second bone fastener during use,
wherein the first dampener set is configured to compress to provide resistance to movement of the first bone fastener away from the second bone fastener during use, and
wherein the second dampener set is configured to compress to provide resistance to movement of the first bone fastener away from the second bone fastener during use.

36. The dynamic stabilization system of claim 35, wherein the first dampener set comprises a plurality of dampeners.

37. The dynamic stabilization system of claim 35, wherein the first dampener set comprises a first dampener concentrically positioned relative to a second dampener.

38. The dynamic stabilization system of claim 35, wherein the first dampener set comprises a dampener with large and small diameter sections.

39. The dynamic stabilization system of claim 35, further comprising at least one washer coupled to the variable length elongated member.

40. The dynamic stabilization system of claim 35, further comprising at least one dynamic interbody device configured to be positioned between the first vertebra and the second vertebra.

41. A dynamic stabilization system, comprising:
a first bone fastener configured to couple to a first vertebra;
a second bone fastener configured to couple to a second vertebra; and
a dampener system, comprising:
  a variable length elongated member configured to couple to the first bone fastener and the second bone fastener;
  a first dampener set coupled to the variable length elongated member on a first side of the member; and
  a second dampener set coupled to the variable length elongated member on a second side of the member,
wherein movement of the first bone fastener towards the second bone fastener is configured to result in compression of the first dampener set and is not configured to result in compression of the second dampener set during use, wherein movement of the first bone fastener away from the second bone fastener is configured to result in compression of the first dampener set and compression of the second dampener set during use, wherein the first dampener set is configured to compress to provide resistance to movement of the first bone fastener towards the second bone fastener during use, wherein the first dampener set is configured to compress to provide resistance to movement of the first bone fastener away from the second bone fastener during use, and wherein the second dampener set is configured to compress to provide resistance to movement of the first bone fastener away from the second bone fastener during use.

42. The dynamic stabilization system of claim 41, wherein the first dampener set comprises a plurality of dampeners.

43. The dynamic stabilization system of claim 41, wherein the first dampener set comprises a first dampener concentrically positioned relative to a second dampener.

44. The dynamic stabilization system of claim 41, wherein the first dampener set comprises a dampener with large and small diameter sections.

45. The dynamic stabilization system of claim 41, further comprising at least one washer coupled to the variable length elongated member.

46. The dynamic stabilization system of claim 41, further comprising at least one dynamic interbody device configured to be positioned between the first vertebra and the second vertebra.

47. A method of stabilizing a portion of a human spine, comprising:
    securing a first bone fastener to a first vertebra;
    securing a second bone fastener to a second vertebra; and
    attaching a dampener system to the first bone fastener and the second bone fastener, wherein the dampener system comprises a first dampener set and a second dampener set positioned on an elongated member,
    wherein the first dampener set is disposed between a head portion of the first bone fastener and a head portion of the second bone fastener during use, and wherein the second dampener set is disposed on an opposite side of the head portion of the second bone fastener from the first dampener set during use,
    wherein compression of the first dampener set is configured to provide resistance to movement of the first bone fastener towards the second bone fastener,
    wherein compression of the first dampener set is configured to provide resistance to movement of the first bone fastener away from the second bone fastener, and
    wherein compression of the second dampener set is configured to provide resistance to movement of the first bone fastener away from the second bone fastener.

48. The method of claim 47, wherein the first dampener set comprises an elastic dampener member and wherein the second dampener set comprises an elastic dampener member.

49. The method of claim 48, wherein each of the first and second dampener sets comprises a first rigid member configured to be disposed on a first side of the elastic dampener member and a second rigid member configured to be disposed on a second side of the elastic dampener member that is opposite from the first side during use such that the first and second rigid members sandwich the respective elastic dampener members.

50. The method of claim 49, wherein movement of the first bone fastener towards the second bone fastener is configured to result in movement of the first and second rigid members of the first dampener set to toward one another to compress the elastic dampener of the first dampener set during use, and wherein movement of the first bone fastener away from the second bone fastener is configured to result in movement of the first and second rigid members of the first dampener set toward one another and movement of the first and second rigid members of the second dampener set toward one another to compress the respective elastic dampeners of the first and second dampener sets during use.

51. The method of claim 47, further comprising securing at least one dynamic interbody device between the first vertebra and the second vertebra.

52. A method of stabilizing a portion of a human spine, comprising:
    securing a first bone fastener to a first vertebra;
    securing a second bone fastener to a second vertebra; and
    attaching a dampener system to the first bone fastener and the second bone fastener, wherein the dampener system comprises a first dampener set and a second dampener set positioned on an elongated member,
    wherein movement of the first bone fastener towards the second bone fastener is configured to result in compression of the first dampener set and is not configured to result in compression of the second dampener set during use,
    wherein movement of the first bone fastener away from the second bone fastener is configured to result in compression of the first dampener set and compression of the second dampener set during use,
    wherein compression of the first dampener set is configured to provide resistance to movement of the first bone fastener towards the second bone fastener,
    wherein compression of the first dampener set is configured to provide resistance to movement of the first bone fastener away from the second bone fastener, and
    wherein compression of the second dampener set is configured to provide resistance to movement of the first bone fastener away from the second bone fastener.

53. The method of claim 52, wherein the first dampener set comprises an elastic dampener member and wherein the second dampener set comprises an elastic dampener member.

54. The method of claim 53, wherein each of the first and second dampener sets comprises a first rigid member configured to be disposed on a first side of the elastic dampener member and a second rigid member configured to be disposed on a second side of the elastic dampener member that is opposite from the first side during use such that the first and second rigid members sandwich the respective elastic dampener members.

55. The method of claim 54, wherein movement of the first bone fastener towards the second bone fastener is configured to result in movement of the first and second rigid members of the first dampener set to toward one another to compress the elastic dampener of the first dampener set during use, and wherein movement of the first bone fastener away from the second bone fastener is configured to result in movement of the first and second rigid members of the first dampener set toward one another and movement of the first and second rigid members of the second dampener set toward one another to compress the respective elastic dampeners of the first and second dampener sets during use.

56. The method of claim 52, further comprising securing at least one dynamic interbody device between the first vertebra and the second vertebra.

* * * * *